(12) United States Patent
Kim et al.

(10) Patent No.: US 11,273,130 B2
(45) Date of Patent: Mar. 15, 2022

(54) METHODS OF DELIVERING A NEUROPROTECTIVE POLYPEPTIDE TO THE CENTRAL NERVOUS SYSTEM

(71) Applicants: Peptron, Inc., Daejeon (KR); The United States of America, as represented by the Secretary, Department of Health & Human Services, Rockville, MD (US)

(72) Inventors: Dong Seok Kim, Columbia, MD (US); Hee Kyung Kim, Daejeon (KR); Nigel H. Greig, Phoenix, MD (US)

(73) Assignees: The United States, as represented by the Secretary Department of Health and Human Services, Rockville, MD (US); Peptron, Inc., Daejeon (KR)

( * ) Notice: Subject to any disclaimer, the term of this patent is extended or adjusted under 35 U.S.C. 154(b) by 0 days.

(21) Appl. No.: 16/342,685

(22) PCT Filed: Oct. 20, 2017

(86) PCT No.: PCT/US2017/057606
§ 371 (c)(1),
(2) Date: Apr. 17, 2019

(87) PCT Pub. No.: WO2018/075901
PCT Pub. Date: Apr. 26, 2018

(65) Prior Publication Data
US 2020/0046645 A1 Feb. 13, 2020

Related U.S. Application Data
(60) Provisional application No. 62/410,748, filed on Oct. 20, 2016.

(51) Int. Cl.
| | | |
|---|---|---|
| A61K 9/50 | (2006.01) | |
| A61P 25/28 | (2006.01) | |
| A61P 25/30 | (2006.01) | |
| A61P 25/16 | (2006.01) | |
| A61K 9/00 | (2006.01) | |
| A61K 9/48 | (2006.01) | |
| A61K 38/26 | (2006.01) | |
| A61M 5/142 | (2006.01) | |

(52) U.S. Cl.
CPC .......... *A61K 9/5031* (2013.01); *A61K 9/0019* (2013.01); *A61K 9/4866* (2013.01); *A61K 38/26* (2013.01); *A61M 5/14228* (2013.01); *A61P 25/16* (2018.01); *A61P 25/28* (2018.01); *A61P 25/30* (2018.01)

(58) Field of Classification Search
CPC .. A61K 9/5031; A61K 9/0019; A61K 9/4866; A61K 38/26; A61K 47/34; A61K 9/16; A61K 9/1641; A61K 9/1647; A61K 9/0021; A61K 38/2278; A61P 25/28; A61P 25/30; A61P 25/16; A61P 25/00; A61M 5/14228; C07K 14/57563
See application file for complete search history.

(56) References Cited

U.S. PATENT DOCUMENTS

| 9,259,432 B1* | 2/2016 | Vig .................... A61K 31/704 |
|---|---|---|
| 2008/0318837 A1* | 12/2008 | Quay ................. A61K 9/0043 |
| | | 514/1.1 |
| 2010/0028292 A1* | 2/2010 | Kabanov ................ A61P 25/00 |
| | | 424/78.37 |

FOREIGN PATENT DOCUMENTS

| EP | 2022505 A2 * | 2/2009 | ............... A61P 3/10 |
|---|---|---|---|
| WO | 2006/014425 A1 | 2/2006 | |
| WO | 2008/117927 A1 | 10/2008 | |
| WO | 2012/177929 A2 | 12/2012 | |
| WO | 2015/158270 A1 | 10/2015 | |

OTHER PUBLICATIONS

Rachmany et al. (Exendin-4 induced glucagon-like peptide-1 receptor activation reverses behavioral impairments of mild traumatic brain injury in mice, American Aging Association (AGE) (2013) 35:1621-1636) (Year: 2012).*

(Continued)

*Primary Examiner* — Quanglong N Truong
(74) *Attorney, Agent, or Firm* — Mintz Levin Cohn Ferris Glovsky and Popeo, P.C.; Peter F. Corless; Joohee Lee

(57) ABSTRACT

The present disclosure provides a method for delivering a neuroprotective polypeptide to at least a portion of a central nervous system (CNS) of a subject. The method includes administering to the systemic blood circulation of the subject a therapeutically effective amount of a neuroprotective polypeptide by a controlled-release formulation or a device providing a sustained release of the neuroprotective polypeptide including at least one neuroprotective polypeptide selected from the group consisting of GLP-1, exendin-4, or a therapeutically effective GLP-1 or exendin-4 analogue; the neuroprotective polypeptide binds to and activates a receptor that binds at least one of GLP-1, exendin-4, or a combination thereof; and the controlled-release neuroprotective formulation or the sustained release of the neuroprotective polypeptide enhances the delivery of the neuroprotective polypeptide across a blood-brain barrier (BBB) of the subject to at least a portion of the CNS relative to a rapid release formulation of the neuroprotective polypeptide. Also disclosed is a method of treating a subject with a CNS-related disease or reducing at least one symptom of a CNS-related disease in a subject in need thereof.

39 Claims, 30 Drawing Sheets
Specification includes a Sequence Listing.

(56) References Cited

OTHER PUBLICATIONS

Gu et al. ("Pharmacokinetic properties and effects of PT302 after repeated oral glucose loading tests in a dose-escalating study". Clin Ther. Jan. 1, 2014;36(1):101-14) (Year: 2014).*

Thomas Foltynie et al: "Exenatide as a potential treatment for patients with Parkinson's disease: First steps into the clinic", Alzheimer's & Dementia: The Journal of the Alzheimer's Association, vol. 10, No. 1, Feb. 1, 2014 (Feb. 1, 2014), pp. S38-S46, XP055442196.

Peptron:"Why Exenatide for Neurodegenerative diseases SR-Exenatide for the Treatment of Neurodegenerative Diseases Profile SR-Exenatide (PT320) for the Treatment of Parkinson's Disease",May 1, 2014 (May 1, 2014), XP055442223, Retrieved from the Internet: URL:http://peptron.com/m/ds_imgs/sub03/SR-Exenatide ND June2014. pdf [retrieved on Jan. 18, 2018] the whole document.

U.S.National Institutes of Health: "NCT01971242 on Mar. 16, 2015: ClinicalTrials.gov Archive", Mar. 16, 2015 (Mar. 16, 2015), XP055442181, Retrieved from the Internet: URL:https://clinicaltrials.govtarchive/NCT01971242/2015_03 16 [retrieved on Jan. 18, 2018] the whole document.

Iciar Aviles-Olmos et al: "Motor and Cognitive Advantages Persist 12 Months After Exenatide Exposure in Parkinson's Disease", Journal of Parkinson's Disease, vol. 4, No. 3, Jul. 28, 2015 (Jul. 28, 2015), pp. 337-344, XP055442141, NL ISSN: 1877-7171, DOI: 10.3233/JPD-140364 abstract.

Iciar Aviles-Olmos et al: "Exenatide and the treatment of patients with Parkinson's disease", Journal of Clinical Investigation, vol. 123, No. 6, Jun. 3, 2013 (Jun. 3, 2013), pp. 2730-2736, XP055442152, US ISSN: 0021-9738,? DOI: 10.1172/JCI68295 the whole document.

Mark Fineman et al: "Pharmacokinetics and Pharmacodynamics of Exenatide Extended-Release After Single and Multiple Dosing:", Clinical Pharmacokinetics., vol. 50, No. 1, Jan. 1, 2011 (Jan. 1, 2011), pp. 65-74, XP055442145, NZ ISSN:0312-5963, DOI: 10.2165/11585880-000000000-00000 abstract.

Dong Seok Kim et al: "A New Treatment Strategy for Parkinson's Disease through the Gut-Brain Axis: The Glucagon-Like Peptide-1 Receptor Pathway", Cell Transplantation, vol. 26, No. 9, Sep. 8, 2017 (Sep. 8, 2017), pp. 1560-1571, XP055442220, US ISSN: 0963-6897, DOI: 10.1177/0963689717721234 the whole document.

Athauda Dilan et al: "Exenatide once weekly versus placebo in Parkinson's disease: a randomised, double-blind, placebo-controlled trial", The Lancet, vol. 390, No. 10103, Jan. 7, 2017 (Jan. 7, 2017), pp. 1664-1675, XP085230321, ISSN: ?0140-6736, DOI: 10.1016/S0140-6736(17)31585-4 the whole document.

International Search Report issued in corresponding PCT Patent Application No. PCT/US2017/057606 dated Jul. 2, 2018.

Search Report issued in corresponding Singaporean Patent Application No. SG 11201903462, dated Sep. 21, 2020.

EP Communication issued in corresponding EP Patent Application No. EP 17800650.8, dated Jul. 2, 2020.

Office Action issued in corresponding Korean Patent Application No. KR 10-2019-7014421, dated Apr. 3, 2020.

* cited by examiner

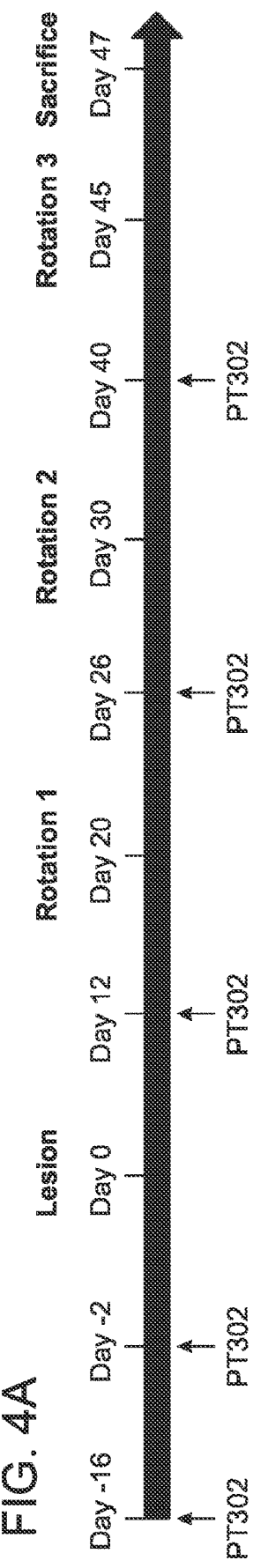
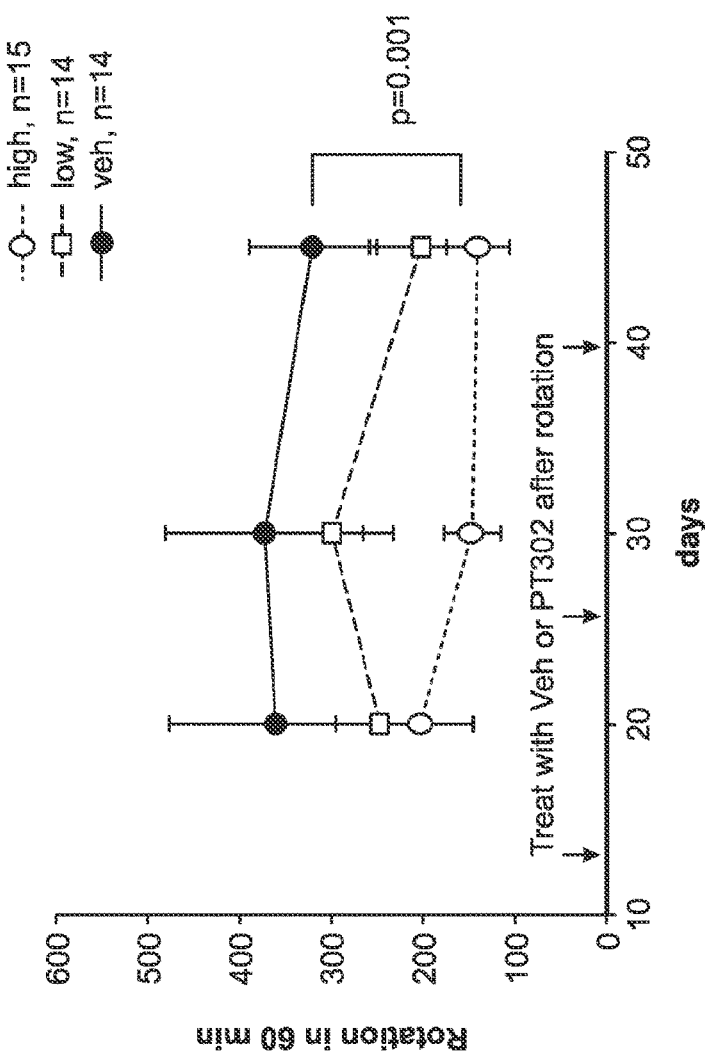
FIG. 4A
FIG. 4B

Non-lesioned side nigra

PT302(#882)

veh(#886)

PT302(#875)

| Dunnett's multiple comparisons test | Mean Diff. | 95.00% CI of diff. | Significant? | Summary | Adjusted P Value |
|---|---|---|---|---|---|
| Control vs. Ex-4 | 152 | 54.96 to 249 | Yes | ** | 0.005 |
| Control vs. PT302 0.4mg/kg | 173 | 75.96 to 270 | Yes | ** | 0.0022 |

Semi-Log plot of plasma Exendin-4 levels in male ICR mice after a single subcutaneous injection of PT302 (0.024 mg/kg, 0.12 mg/kg, 0.6 mg/kg)

PT302 dose:
- ♦ - 0.024 mg/kg
- ■ - 0.12 mg/kg
- ▲ - 0.6 mg/kg

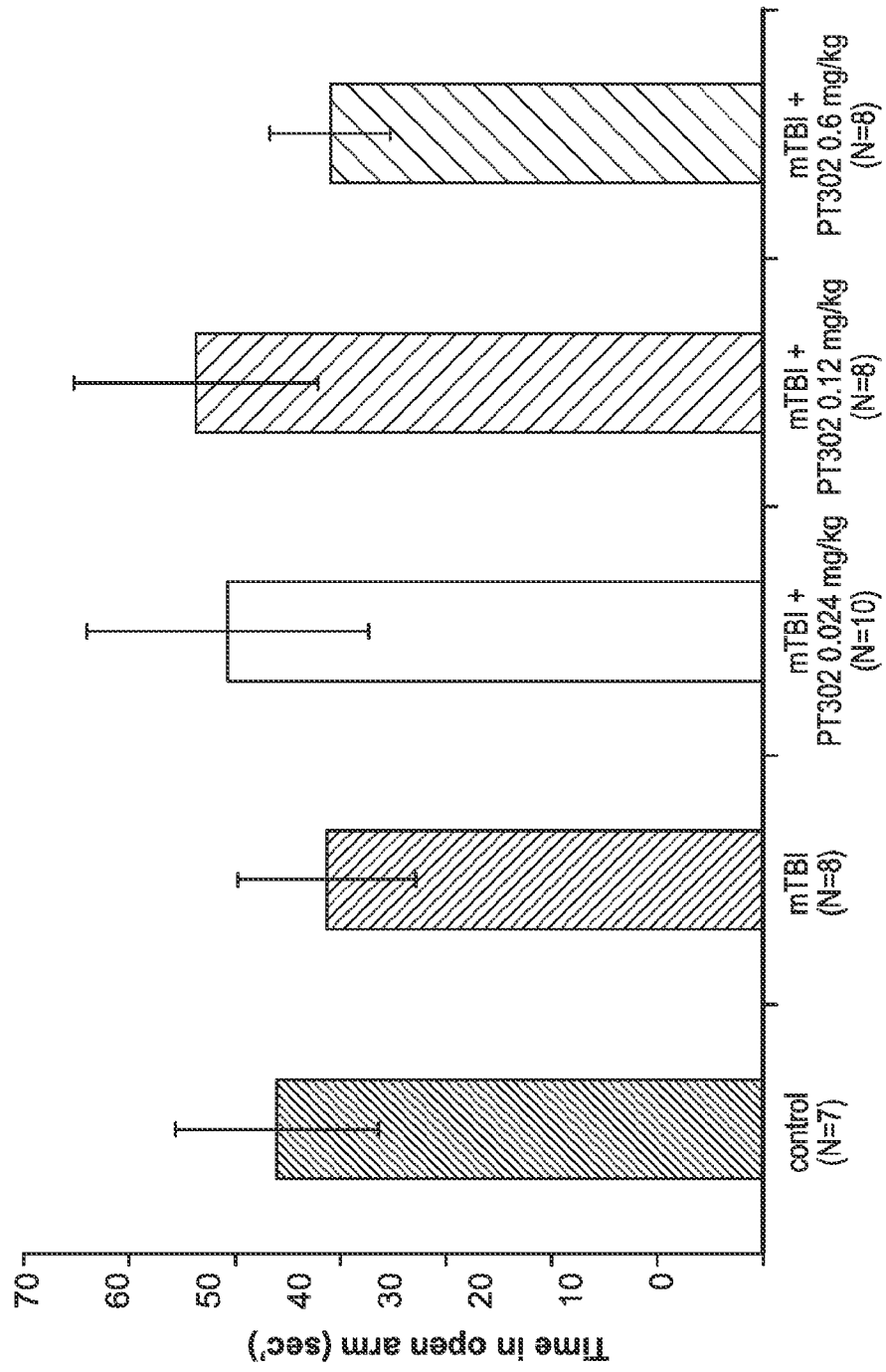

FIG. 11C Elevated plus maze evaluation at 7 days following mild traumatic brain injury (mTBI) Mice were subjected to a 30g weight drop and treated with PT302 (0, 0.024, 0.12 or 0.6 kg/kg s.c.) after mTBI. Control animals were handled similarly but received no mTBI.

N.B. The elevated plus maze provides an evaluation of 'anxiety' - a lack of effect indicates that mTBI was not anxiogenic - and hence not a confound when assessing Novel Object Recognition and Y-maze paradigms Animal number (N) in parenthesis

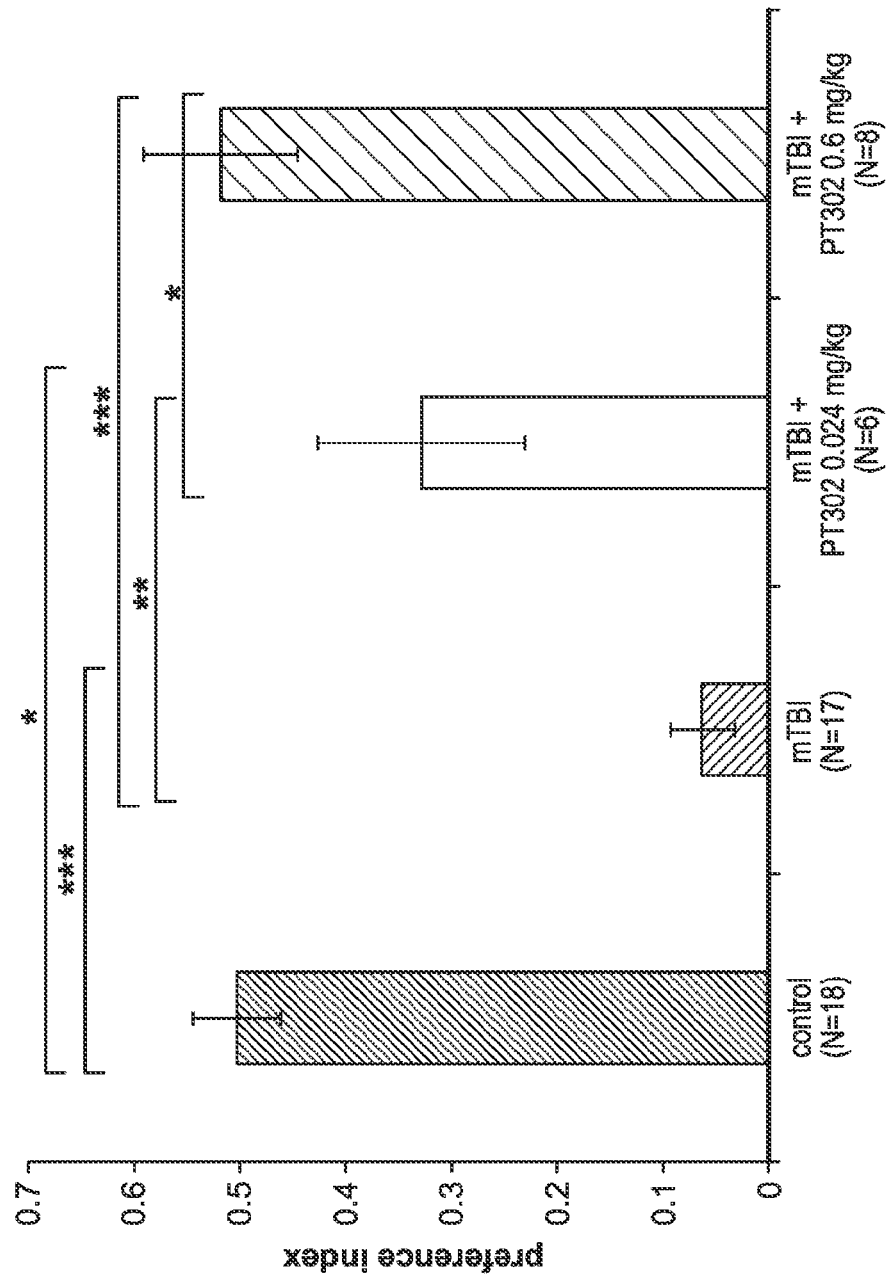
FIG. 12A Novel object recognition at 30 days following mild traumatic brain injury (mTBI) Mice were subjected to a 30g weight drop and treated with PT302 (0, 0.024, 0.12 or 0.6 kg/kg s.c.) after mTBI. Control animals were handled similarly but received no mTBI
Statistical significance: * $p \leq 0.05$,  $p \leq 0.01$, * $p \leq 0.001$
Animal number (N) in parenthesis

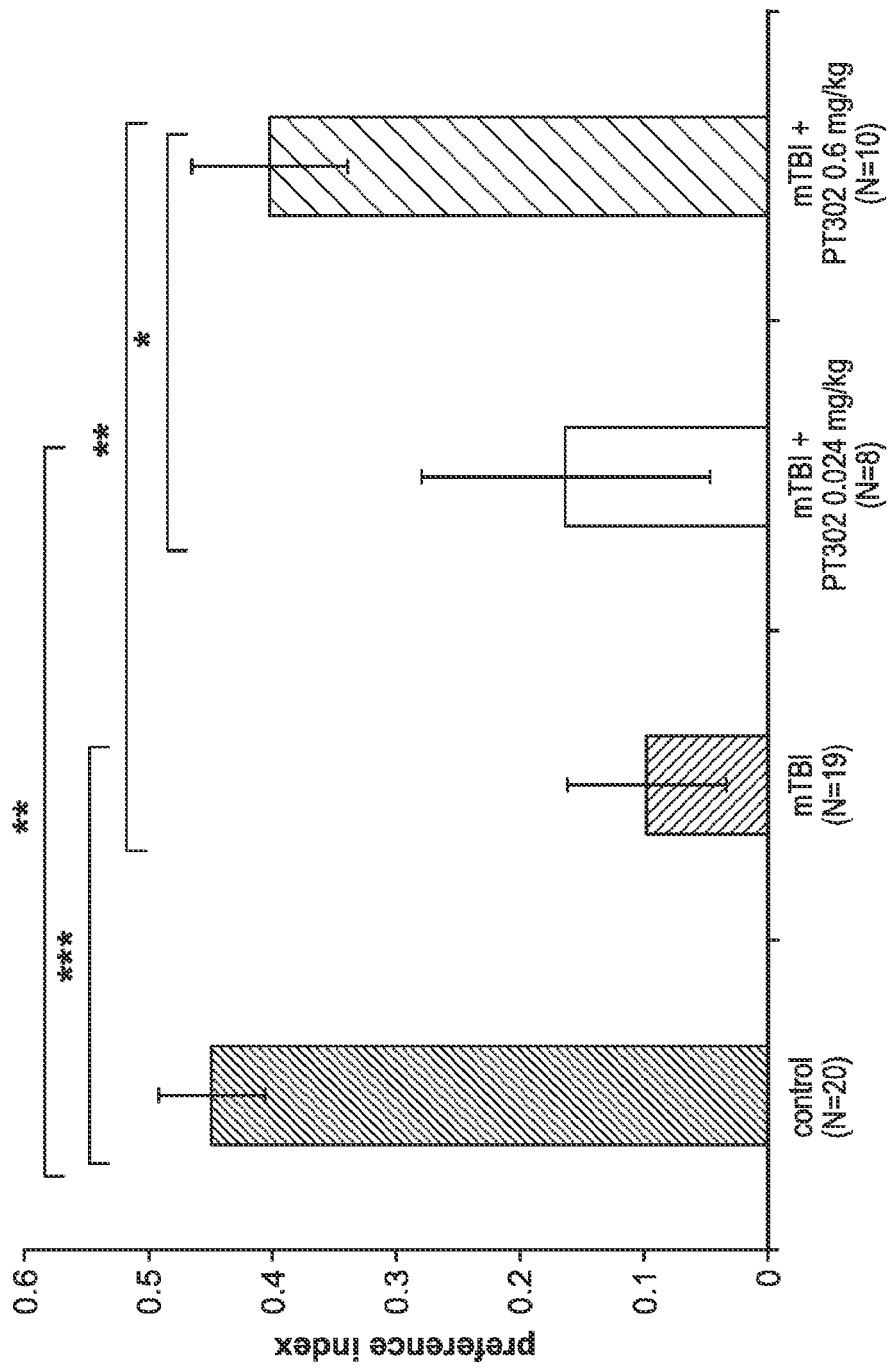

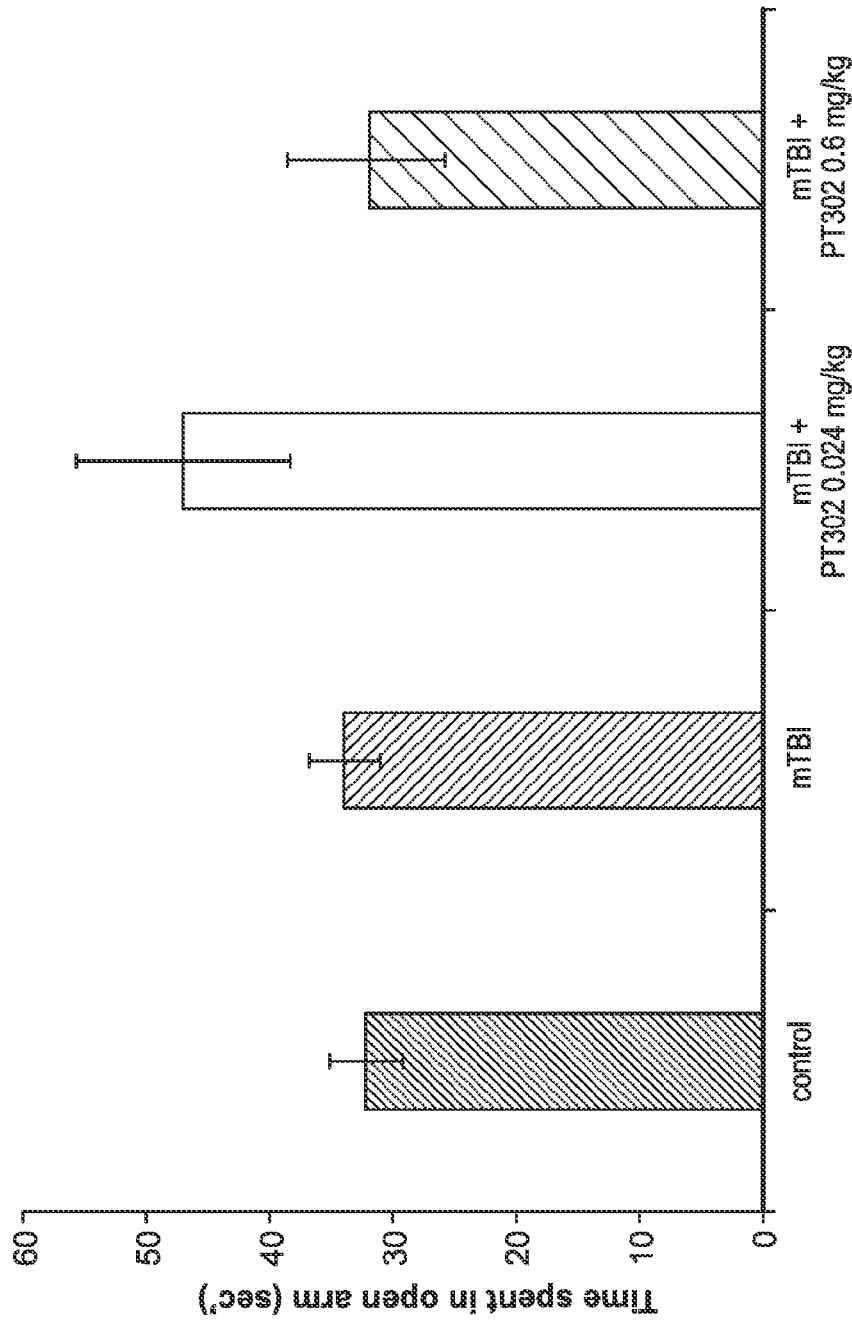

FIG. 12C Elevated plus maze evaluation at 30 days following mild traumatic brain injury (mTBI) Mice were subjected to a 30g weight drop and treated with PT302 (0, 0.024, 0.12 or 0.6 kg/kg s.c.) after mTBI. Control animals were handled similarly but received no mTBI.

N.B. The elevated plus maze provides an evaluation of 'anxiety' - a lack of effect indicates that mTBI was not anxiogenic - and hence not a confound when assessing Novel Object Recognition and Y-maze paradigms Animal number (N = 8 to 9 mice per group)

SEQUENCE LISTING

```
<160> NUMBER OF SEQ ID NOS: 55

<210> SEQ ID NO 1
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 1

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 2
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
```

```
            20                  25                  30

Ser Gly Ala Pro Pro Ser
        35

<210> SEQ ID NO 3
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 3

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 5

His Gly Glu Gly Thr Phe Thr Ser Asp Leu Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 6
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 6

His Gly Glu Gly Thr Phe Thr Ser Asp Leu Ser Lys Gln Met Glu Gly
1               5                   10                  15

Gln Ala Ala Lys Glu Phe Ile Ala Trp Leu Val Lys Gly Arg
            20                  25                  30

<210> SEQ ID NO 7
<211> LENGTH: 30
<212> TYPE: PRT
<213> ORGANISM: Artificial Sequence
<220> FEATURE:
```

```
<223> OTHER INFORMATION: Description of Artificial Sequence: Note =
      Synthetic Construct

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 8

His Xaa Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg
            20                  25                  30

<210> SEQ ID NO 9
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 30
<223> OTHER INFORMATION: Xaa=any amino acid

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Xaa Pro Ser
            20                  25                  30

Ser Gly Ala Pro Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 10

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 11
<211> LENGTH: 30
```

```
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 11

His Ala Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 12
<211> LENGTH: 37
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro
        35

<210> SEQ ID NO 13
<211> LENGTH: 35
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala
        35

<210> SEQ ID NO 14
<211> LENGTH: 33
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser

<210> SEQ ID NO 15
<211> LENGTH: 28
<212> TYPE: PRT
<213> ORGANISM: Artificial Sequence
<220> FEATURE:
```

<223> OTHER INFORMATION: Description of Artificial Sequence: Note =
      Synthetic Construct

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 16
<211> LENGTH: 26
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 16

His Gly Glu Gly Thr Phe Thr Ser Asp Leu Ser Lys Gln Met Glu Glu
1               5                   10                  15

Glu Ala Val Arg Leu Phe Ile Glu Trp Leu
            20                  25

<210> SEQ ID NO 17
<211> LENGTH: 23
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 17

His Gly Glu Gly Thr Phe Thr Ser Asp Leu Ser Lys Gln Met Glu Glu
1               5                   10                  15

Glu Ala Val Arg Leu Phe Ile
            20

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 18

His Gly Glu Gly Thr Phe Thr Ser Asp Leu Ser Lys Gln Met Glu Glu
1               5                   10                  15

Glu Ala Val Arg
            20

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 19

His Gly Glu Gly Thr Phe Thr Ser Asp Leu Ser Lys Gln Met Glu Glu
1               5                   10                  15

Glu

```
<210> SEQ ID NO 20
<211> LENGTH: 14
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 20

His Gly Glu Gly Thr Phe Thr Ser Asp Leu Ser Lys Gln Met
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 21

His Gly Glu Gly Thr Phe Thr Ser Asp Leu Ser
1               5                   10

<210> SEQ ID NO 22
<211> LENGTH: 34
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 3,4,5,6
<223> OTHER INFORMATION: Xaa= aminohexanoic acid

<400> SEQUENCE: 22

His Ala Xaa Xaa Xaa Xaa Glu Gly Thr Phe Thr Ser Asp Val Ser Ser
1               5                   10                  15

Tyr Leu Glu Gly Gln Ala Ala Lys Glu Phe Ile Ala Trp Leu Val Lys
            20                  25                  30

Gly Arg

<210> SEQ ID NO 23
<211> LENGTH: 38
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 3,4,5,6,7,8,9,10
<223> OTHER INFORMATION: Xaa=aminohexanoic acid

<400> SEQUENCE: 23

His Ala Xaa Xaa Xaa Xaa Xaa Xaa Xaa Xaa Glu Gly Thr Phe Thr Ser
1               5                   10                  15

Asp Val Ser Ser Tyr Leu Glu Gly Gln Ala Ala Lys Glu Phe Ile Ala
            20                  25                  30

Trp Leu Val Lys Gly Arg
        35

<210> SEQ ID NO 24
<211> LENGTH: 30
<212> TYPE: PRT
<213> ORGANISM: Artificial Sequence
```

```
<220> FEATURE:
<223> OTHER INFORMATION: Description of Artificial Sequence: Note =
      Synthetic Construct

<400> SEQUENCE: 24

His Gly Glu Gly Thr Phe Thr Ser Asp Val Ser Ser Tyr Met Glu Glu
1               5                   10                  15

Gln Ala Val Arg Leu Phe Ile Ala Trp Leu Val Lys Gly Arg
            20                  25                  30

<210> SEQ ID NO 25
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 25

His Gly Glu Gly Thr Phe Thr Ser Asp Val Ser Ser Tyr Met Glu Glu
1               5                   10                  15

Gln Ala Ala Lys Glu Phe Ile Ala Trp Leu Val Lys Gly Arg
            20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 26

His Gly Glu Gly Thr Phe Thr Ser Asp Val Ser Ser Tyr Leu Glu Gly
1               5                   10                  15

Gln Ala Val Arg Leu Phe Ile Ala Trp Leu Val Lys Gly Arg
            20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 27

His Gly Glu Gly Thr Phe Thr Ser Asp Val Ser Lys Tyr Leu Glu Gly
1               5                   10                  15

Gln Ala Ala Lys Glu Phe Ile Ala Trp Leu Val Lys Gly Arg
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 28

His Gly Glu Gly Thr Phe Thr Ser Asp Val Ser Lys Tyr Leu Glu Glu
1               5                   10                  15

Glu Ala Ala Lys Glu Phe Ile Ala Trp Leu Val Lys Gly Arg
            20                  25                  30
```

<210> SEQ ID NO 29
<211> LENGTH: 30
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 29

His Gly Glu Gly Thr Phe Thr Ser Asp Val Ser Lys Tyr Leu Glu Glu
1               5                   10                  15

Glu Ala Ala Lys Glu Phe Ile Glu Trp Leu Val Lys Gly Gly
            20                  25                  30

<210> SEQ ID NO 30
<211> LENGTH: 30
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 30

His Gly Glu Gly Thr Phe Thr Ser Asp Val Ser Lys Tyr Leu Glu Glu
1               5                   10                  15

Glu Ala Ala Lys Glu Phe Ile Glu Trp Leu Val Lys Gly Arg
            20                  25                  30

<210> SEQ ID NO 31
<211> LENGTH: 30
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 31

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Arg
            20                  25                  30

<210> SEQ ID NO 32
<211> LENGTH: 30
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 32

His Gly Glu Gly Thr Phe Thr Ser Asp Leu Ser Lys Gln Met Glu Glu
1               5                   10                  15

Glu Ala Val Arg Leu Phe Ile Ala Trp Leu Lys Asn Gly Arg
            20                  25                  30

<210> SEQ ID NO 33
<211> LENGTH: 30
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 33

His Gly Glu Gly Thr Phe Thr Ser Asp Leu Ser Lys Gln Met Glu Glu
1               5                   10                  15

Glu Ala Val Arg Glu Phe Ile Ala Trp Leu Lys Asn Gly Arg
            20                  25                  30

<210> SEQ ID NO 34
<211> LENGTH: 39
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 34

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Pro Ser
            20                  25                  30

Ser Gly Ala Pro Pro Ser
        35

<210> SEQ ID NO 35
<211> LENGTH: 39
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 35

His Gly Glu Gly Thr Phe Thr Ser Asp Val Ser Ser Tyr Leu Glu Gly
1               5                   10                  15

Gln Ala Ala Lys Glu Phe Ile Glu Trp Leu Lys Asn Gly Gly Pro Ser
            20                  25                  30

Ser Gly Ala Pro Pro Ser
        35

<210> SEQ ID NO 36
<211> LENGTH: 30
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 36

His Gly Glu Gly Thr Phe Thr Ser Asp Val Ser Ser Tyr Leu Glu Glu
1               5                   10                  15

Glu Ala Val Arg Leu Phe Ile Ala Trp Leu Val Lys Gly Arg
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Note = Synthetic Construct

<400> SEQUENCE: 37

His Gly Glu Gly Thr Phe Thr Ser Asp Leu Ser Lys Gln Met Glu Gly
1               5                   10                  15

Gln Ala Ala Lys Glu Phe Ile Glu Trp Leu Lys Asn Gly Arg

```
            20                  25                  30

<210> SEQ ID NO 38
<211> LENGTH: 42
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 38

Tyr Gly Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
        35                  40

<210> SEQ ID NO 39
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 39

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Pro Ser
        35

<210> SEQ ID NO 40
<211> LENGTH: 42
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 40

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Pro Ser Gly Ala Pro
        35                  40

<210> SEQ ID NO 41
<211> LENGTH: 45
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 41

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30
```

Ser Gly Ala Pro Pro Pro Ser Gly Ala Pro Pro Ser Ser
        35                  40                  45

<210> SEQ ID NO 42
<211> LENGTH: 40
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 42

His Xaa Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Pro
            20                  25                  30

Ser Ser Gly Ala Pro Pro Ser
        35                  40

<210> SEQ ID NO 43
<211> LENGTH: 43
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 43

His Xaa Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Pro
            20                  25                  30

Ser Ser Gly Ala Pro Pro Ser Gly Ala Pro
        35                  40

<210> SEQ ID NO 44
<211> LENGTH: 46
<212> TYPE: PRT
<213> ORGANISM: Artificial Sequence
<220> FEATURE:
<223> OTHER INFORMATION: Description of Artificial Sequence: Note =
      Synthetic Construct
<220> FEATURE:
<221> NAME/KEY: VARIANT
<222> LOCATION: 2
<223> OTHER INFORMATION: Xaa= aminohexanoic acid

<400> SEQUENCE: 44

His Xaa Ala Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Pro
            20                  25                  30

Ser Ser Gly Ala Pro Pro Ser Gly Ala Pro Pro Ser Ser
        35                  40                  45

<210> SEQ ID NO 45
<211> LENGTH: 40
<212> TYPE: PRT

<213> ORGANISM: Artificial Sequence
<220> FEATURE:
<223> OTHER INFORMATION: Description of Artificial Sequence: Note = Synthetic Construct
<220> FEATURE:
<221> NAME/KEY: VARIANT
<222> LOCATION: 3
<223> OTHER INFORMATION: Xaa= aminohexanoic acid

<400> SEQUENCE: 45

```
His Ala Xaa Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Pro
            20                  25                  30

Ser Ser Gly Ala Pro Pro Ser
        35                  40
```

<210> SEQ ID NO 46
<211> LENGTH: 43
<212> TYPE: PRT
<213> ORGANISM: Artificial Sequence
<220> FEATURE:
<223> OTHER INFORMATION: Description of Artificial Sequence: Note = Synthetic Construct
<220> FEATURE:
<221> NAME/KEY: VARIANT
<222> LOCATION: 3
<223> OTHER INFORMATION: Xaa= aminohexanoic acid

<400> SEQUENCE: 46

```
His Ala Xaa Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Pro
            20                  25                  30

Ser Ser Gly Ala Pro Pro Ser Gly Ala Pro
        35                  40
```

<210> SEQ ID NO 47
<211> LENGTH: 46
<212> TYPE: PRT
<213> ORGANISM: Artificial Sequence
<220> FEATURE:
<223> OTHER INFORMATION: Description of Artificial Sequence: Note = Synthetic Construct
<220> FEATURE:
<221> NAME/KEY: VARIANT
<222> LOCATION: 3
<223> OTHER INFORMATION: Xaa= aminohexanoic acid

<400> SEQUENCE: 47

```
His Ala Xaa Glu Gly Thr Phe Thr Ser Asp Val Ser Ser Tyr Leu Glu
1               5                   10                  15

Gly Gln Ala Ala Lys Glu Phe Ile Ala Trp Leu Val Lys Gly Arg Pro
            20                  25                  30

Ser Ser Gly Ala Pro Pro Ser Gly Ala Pro Pro Ser Ser
        35                  40                  45
```

<210> SEQ ID NO 48
<211> LENGTH: 43
<212> TYPE: PRT
<213> ORGANISM: Artificial Sequence
<220> FEATURE:
<223> OTHER INFORMATION: Description of Artificial Sequence: Note = Synthetic Construct
<220> FEATURE:
<221> NAME/KEY: VARIANT
<222> LOCATION: 2

```
<223> OTHER INFORMATION: Xaa= aminohexanoic acid

<400> SEQUENCE: 48

Tyr Xaa Ala Glu Gly Thr Phe Ile Ser Asp Tyr Ser Ile Ala Met Asp
1               5                   10                  15

Lys Ile His Gln Gln Asp Phe Val Asn Trp Leu Leu Ala Gln Lys Gly
            20                  25                  30

Lys Lys Asn Asp Trp Lys His Asn Ile Thr Gln
        35                  40

<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 49

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro
        35

<210> SEQ ID NO 50
<211> LENGTH: 39
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 50

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro Pro Pro Ser
        35

<210> SEQ ID NO 51
<211> LENGTH: 36
<212> TYPE: PRT
<213> ORGANISM: Artificial Sequence
<220> FEATURE:
<223> OTHER INFORMATION: Description of Artificial Sequence: Note =
      Synthetic Construct

<400> SEQUENCE: 51

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser Gly Ala Pro
        35

<210> SEQ ID NO 52
<211> LENGTH: 33
<212> TYPE: PRT
<213> ORGANISM: Artificial Sequence
<220> FEATURE:
```

-continued

```
<223> OTHER INFORMATION: Description of Artificial Sequence: Note =
      Synthetic Construct

<400> SEQUENCE: 52

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Pro Ser
            20                  25                  30

Ser

<210> SEQ ID NO 53
<211> LENGTH: 39
<212> TYPE: PRT
<213> ORGANISM: Artificial Sequence
<220> FEATURE:
<223> OTHER INFORMATION: amino acid sequence of Exendin-3

<400> SEQUENCE: 53

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 54
<211> LENGTH: 31
<212> TYPE: PRT
<213> ORGANISM: Artificial Sequence
<220> FEATURE:
<223> OTHER INFORMATION: amino acid sequence of Exendin-4 variant

<400> SEQUENCE: 54

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 55
<211> LENGTH: 39
<212> TYPE: PRT
<213> ORGANISM: Artificial Sequence
<220> FEATURE:
<223> OTHER INFORMATION: amino acid sequence of 14Leu25Phe Exendin-4
      variant

<400> SEQUENCE: 55

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Pro Ser
        35
```

METHODS OF DELIVERING A NEUROPROTECTIVE POLYPEPTIDE TO THE CENTRAL NERVOUS SYSTEM

CROSS-REFERENCE TO RELATED APPLICATIONS

This application is a U.S. 371 National Phase of International PCT Patent Application No. PCT/US2017/057606, filed Oct. 20, 2017, which application priority to United States Provisional Application No. 62/410,748, filed Oct. 20, 2016. The entire contents of these applications are incorporated herein by reference in their entirety.

GOVERNMENT FUNDING

Research supporting this application was carried out by the United States of America as represented by the Secretary, Department of Health and Human Services. The Government has certain rights in this invention.

INCORPORATION BY REFERENCE

In compliance with 37 C.F.R. § 1.52(e)(5), the sequence information contained in electronic file name: 1568390_100WO2_Sequence_Listing_ST25.txt; size 24.4 KB; created on: 3 Sep. 2017, using Patent-In 3.5, and Checker 4.4.0 is hereby incorporated herein by reference in its entirety.

BACKGROUND

Field

The present disclosure relates to compositions comprising a neuroprotective therapeutic polypeptide, such as, e.g., glucagon-like peptide-1 (GLP-1), exendin-4, and/or their peptide analogs. In particular, the present disclosure relates to methods to maintain a steady-state plasma level of the neuroprotective therapeutic polypeptide to facilitate delivery to the brain across the blood-brain barrier (BBB) for the treatment of a neurodegenerative condition.

Background Art

Glucagon-like peptide-1 (GLP-1), a hormone normally secreted by neuroendocrine cells of the gut in response to food, has been suggested as a new treatment for type 2 diabetes (Gutniak et al., 1992; Nauck et al., 1993). It increases insulin release by beta cells even in subjects with long-standing type 2 diabetes (Nauck et al., 1993). GLP-1 treatment has an advantage over insulin therapy because GLP-1 stimulates endogenous insulin secretion, which turns off when blood glucose levels drop (Nauck et al., 1993; Elahi et al., 1994). GLP-1 promotes euglycemia by increasing insulin release and synthesis, inhibiting glucagon release, and decreasing gastric emptying (Nauck et al., 1993; Elahi et al., 1994; Wills et al., 1996; Nathan et al., 1992; De Ore et al., 1997). GLP-1 is a product of posttranslational modification of proglucagon. The sequences of GLP-1 and its active fragments GLP-1 (7-37) and GLP-1(7-36) amide are known in the art (Fehmann et al., 1995). Although GLP-1 has been proposed as a therapeutic agent in the treatment of diabetes, it has a short biological half-life (De Ore et al., 1997), even when given by a bolus subcutaneously (Ritzel et al., 1995). GLP-1 degradation (and GLP-1 (7-36) amide), in part, is due to the enzyme dipeptidyl peptidase (DPP 1V), which cleaves the polypeptide between amino acids 8 and 9 (alanine and glutamic acid).

Exendin-4 is a polypeptide produced in the salivary glands of the Gila monster lizard (Goke et al., 1993). The amino acid sequence for exendin-4 is known in the art (Fehmann et al. 1995). Although it is the product of a uniquely non-mammalian gene and appears to be expressed only in the salivary gland (Chen and Drucker, 1997), exendin-4 shares a 52% amino acid sequence homology with GLP-1 and in mammals interacts with the GLP-1 receptor (Goke et al., 1993; Thorens et al., 1993). In vitro, exendin-4 has been shown to promote insulin secretion by insulin producing cells and, given in equimolar quantities, is more potent than GLP-1 at causing insulin release from insulin producing cells. Furthermore, exendin-4 potently stimulates insulin release to reduce plasma glucose levels in both rodents and humans and is longer acting than GLP-1. Exendin-4, however, because it does not occur naturally in mammalians, has certain potential antigenic properties in mammals that GLP-1 lacks.

In addition to the reduction in insulin production that occurs in diabetes, peripheral neuropathy is commonly associated with diabetes. Twenty to thirty percent of all diabetes subjects eventually develop peripheral neuropathy. Furthermore, there are reports of increased risk of Alzheimer's disease with heart disease, stroke, hypertension, and diabetes (Moceri et al., 2000; Ott et al., 1999). Thus, diabetes is a disease that is also associated with neurodegenerative diseases.

The GLP-1 receptor is present in both the rodent (Jin et al. 1988, Shughrue et al. 1996, Jia et al. 2015) and human (Wei and Mojsov 1995, Satoh et al. 2000) brains. The chemoarchitecture of the distribution appears to be largely confined to the hypothalamus, thalamus, brainstem, lateral septum, the subfornical organ and the area postrema, all circumventricular areas where generally large numbers of peptide receptors are located. However, specific binding sites for GLP-1 have also been detected throughout the caudate-putamen, cerebral cortex and cerebellum (Campos et al. 1994, Calvo et al. 1995, and Goke et al. 1995), albeit at lower densities. For example, Lu et al. 2014 demonstrated that GLP-1 receptor is expressed in amygdata, cerebellum, frontal cortex, hippocampus, hypothalamus, midbrain, medulla, pons, striatum, thalamus and themporal cortex of *Mustela putorius furo* (ferrets). GLP-1 receptor expression level in the brain is not affected by aging.

Furthermore, GLP-1 has been shown to be related to cognition and behavior. (During et al. 2003). In fact, a number of studies have suggested GLP-1 receptor agonists as a new treatment for neurodegenerative diseases including Parkinson's disease, Alzheimer's disease, Huntington's disease, traumatic brain injury, stroke, and peripheral neuropathy. However, drug delivery to the central nervous system (CNS) across the blood-brain barrier (BBB) is a substantial hurdle for the treatment of CNS-related diseases. For example, GLP-1 has a short half-life of 1-2 minutes and GLP-1-Transferrin fusion protein (GLP-1-Tf), which was produced to resist inactivation and thus increase the half-life of GLP-1 to approximately 2 days, is incapable of crossing the BBB. Kim et al. 2010 and Martin et al. 2012.

Additionally, while Exendin-4 has been shown to improve RotaRod Performance, as compared to GLP-1-Tf (Martin et al. 2012), and is known to enter the brain from the blood, the entry rate is limited (Kastin A J and Akeerstrom V, International Journal of Obesity (2003) 27, 313-318). Furthermore, Exenatide has been shown to be ineffective at providing neuroprotection in the MPTP mouse model for Parkinson's disease when provided with post treatments, daily for seven days (Liu et al. 2015).

As such, a need exists in the art for a method for treating neurodegenerative conditions, as well as a method of maintaining a steady-state plasma level of a neuroprotective GLP-1 receptor agonist, thereby facilitating and driving drug delivery to the central nervous system across the BBB.

SUMMARY

In an aspect of the present disclosure, a method for delivering a neuroprotective polypeptide to at least a portion of a central nervous system (CNS) of a subject. The method comprising: administering to the systemic blood circulation of the subject a therapeutically effective amount of neuroprotective polypeptide by a controlled-release formulation or a device providing a sustained release or delivery of the neuroprotective polypeptide, the neuroprotective polypeptide includes at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof; and wherein the controlled-release neuroprotective formulation or sustained release of the neuroprotective polypeptide enhances the delivery and/or uptake of the neuroprotective polypeptide across a blood-brain barrier (BBB) of the subject to at least a portion of the central nervous system (CNS) relative to a rapid release formulation of the neuroprotective peptide.

In another aspect of the present disclosure, a method of treating a subject with a central nervous system (CNS)-related disease or reducing at least one symptom of a CNS-related disease in a subject in need thereof. The method comprising: administering to the systemic blood circulation of the subject a therapeutically effective amount of a neuroprotective polypeptide by a controlled-release formulation or a device providing a sustained release or delivery of a neuroprotective polypeptide, wherein the neuroprotective polypeptide includes at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4 or a combination thereof; and wherein the controlled-release neuroprotective formulation or a device enhances the delivery of the neuroprotective polypeptide across a blood-brain barrier (BBB) of the subject to at least a portion of the central nervous system (CNS) relative to a rapid release formulation of the neuroprotective polypeptide.

In an aspect of the present disclosure, a method for delivering a neuroprotective polypeptide to at least a portion of a central nervous system (CNS) of a subject is provided. The method comprises administering a controlled-release neuroprotective formulation to the systemic blood circulation of the subject. In an embodiment, the controlled-release neuroprotective formulation includes at least one neuroprotective polypeptide selected from the group consisting of GLP-1, exendin (e.g. exendin-4), or a therapeutically effective GLP-1 or exendin analogue (e.g. exendin-4 analogue), wherein the neuroprotective polypeptide binds to and activates a receptor that binds at least one of GLP-1, exendin (such as exendin-4), or a combination thereof, and the controlled-release neuroprotective formulation enhances the delivery of the neuroprotective polypeptide across a blood-brain barrier (BBB) of the subject to at least a portion of the central nervous system (CNS) relative to rapid release formulation of the neuroprotective polypeptide.

In certain embodiments, the controlled-release formulation is a long acting formulation of the neuroprotective polypeptide.

In other embodiments, the long acting formulation comprises a depot formulation for sustained release of the neuroprotective polypeptide.

In particular embodiments, the long acting formulation comprises a composition for sustained release of the neuroprotective polypeptide.

In additional embodiments, the controlled-release formulation further comprises a biodegradable polymer with a specific viscosity and coating materials, having bioavailability and sustained release of the neuroprotective polypeptide in an effective concentration for a certain period.

In particular embodiments, the controlled-release neuroprotective formulation comprises: a controlled-release microsphere that includes a core with the neuroprotective polypeptide and a biodegradable polymer; and a coating layer that coats the core.

In an embodiment, administering the controlled-release neuroprotective formulation alleviates at least one symptom of at least one CNS-related condition in the subject.

In further embodiments, the CNS-related condition is selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy (CTE), motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

In a certain embodiment, administering a controlled-release neuroprotective formulation comprises injecting the controlled-release neuroprotective formulation.

In additional embodiments, injecting the controlled-release neuroprotective formulation is a subcutaneous injection. For example, administering a controlled-released neuroprotective formulation can comprise subcutaneously injecting the controlled-release neuroprotective formulation.

In another embodiment, administering the controlled-release neuroprotective formulation results in a steady-state plasma concentration of the neuroprotective polypeptide in a range of about 50 to about 4500 pg/mL.

In other embodiments, administering the controlled-release neuroprotective formulation results in a cumulative increase in the neuroprotective polypeptide concentration in the cerebrospinal fluid (CSF), the brain or a combination thereof in the subject.

In particular embodiments, the neuroprotective polypeptide concentration in the CSF is within the range of about 5 to about 400 pg/mL (e.g., about 10 to about 400 pg/mL).

In an additional aspect, a method of treating a subject with a CNS-related disease or reducing at least one symptom of a CNS-related disease in a subject in need thereof is provided. The method comprises administering to the subject a therapeutically effective amount of a controlled-release neuroprotective formulation to the systemic blood circulation of the subject. The controlled-release neuroprotective formulation includes at least one neuroprotective polypeptide selected from the group consisting of GLP-1, exendin (such as exendin-4), or a therapeutically effective GLP-1 or exendin (such as exendin-4) analogue; the neuroprotective polypeptide binds to and activates a receptor that binds at least one of GLP-1, exendin (e.g. exendin-4) or a combination thereof; and the controlled-release neuroprotective formulation enhances the delivery of the neuroprotective polypeptide across a BBB of the subject to at least a portion of the CNS relative to a rapid release formulation of the neuroprotective polypeptide.

In certain embodiments, the controlled-release formulation is a long acting formulation of the neuroprotective polypeptide.

In other embodiments, the long acting formulation comprises a depot formulation for sustained release of the neuroprotective polypeptide.

In additional embodiments, the long acting formulation comprises a composition for sustained release of the neuroprotective polypeptide.

In additional embodiments, the controlled-release formulation further comprises a biodegradable polymer with a specific viscosity and coating materials, having bioavailability and sustained release of the neuroprotective polypeptide in an effective concentration for a certain period.

In particular embodiments, the controlled-release neuroprotective formulation comprises: a controlled-release microsphere that includes a core with the neuroprotective polypeptide and a biodegradable polymer; and a coating layer that coats the core.

In a particular embodiment, administering the controlled-release neuroprotective formulation alleviates at least one symptom of at least one CNS-related condition in the subject.

In an embodiment, the CNS condition is selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy, motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

In further embodiments, administering the controlled-release neuroprotective formulation comprises injecting the controlled-release neuroprotective formulation to the subject.

In certain embodiments, injecting the controlled-release neuroprotective formulation to the subject is a subcutaneous injection.

In additional embodiments, administering the controlled-release formulation results in a steady-state plasma concentration of the neuroprotective polypeptide that is in a range of about 50 to about 4500 pg/mL.

In some embodiments, administering the controlled-release formulation results in a cumulative increase in the neuroprotective polypeptide concentration in at least one of the cerebrospinal fluid (CSF), the brain, or a combination thereof.

In a further aspect, a method for delivering a neuroprotective polypeptide to at least a portion of a central nervous system (CNS) of a subject is provided. The method comprises: providing a sustained delivery to the systemic blood circulation of the subject at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof; and wherein the controlled-release neuroprotective formulation enhances the delivery and/or uptake of the neuroprotective polypeptide across a blood brain barrier (BBB) of the subject to at least a portion of the central nervous system (CNS) relative to a rapid release formulation of the neuroprotective peptide.

In yet another aspect, a method of treating a subject with a central nervous system (CNS)-related disease or reducing at least one symptom of a CNS-related disease in a subject in need thereof is provided. The method comprises: providing a sustained delivery to the systemic blood circulation of the subject at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4 or a combination thereof; and wherein the controlled-release neuroprotective formulation enhances the delivery of the neuroprotective polypeptide across a blood brain barrier (BBB) of the subject to at least a portion of the central nervous system (CNS) relative to a rapid release formulation of the neuroprotective polypeptide.

In an embodiments, providing the sustained release neuroprotective polypeptide or polypeptides includes administering the polypeptide(s) via a device (e.g., a pump, a mini-pump, an osmotic pump, an osmotic delivery device, an infusion pump, an intravenous administration device, a peristaltic pump, a miniature infusion pump, or the like).

In certain embodiments, the neuroprotective polypeptide or polypeptides is administered at a rate of about 1 pM/kg/min to about 30 pM/kg/min (e.g., about 3 pM/kg/min to about 17.5 pM/kg/min).

In other embodiments, administering the controlled-release neuroprotective formulation or providing a sustained delivery of the neuroprotective polypeptide alleviates at least one symptom of at least one CNS-related condition in the subject.

In particular embodiments, the CNS-related condition is selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy, motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

In an embodiment, administering the controlled-release formulation or providing the sustained release of the neuroprotective polypeptide results in a steady-state plasma concentration of the neuroprotective polypeptide that is in a range of about 50 to about 4500 pg/mL.

In certain embodiments, administering the controlled-release formulation or providing the sustained release of the neuroprotective polypeptide results in a cumulative increase in the neuroprotective polypeptide concentration in at least one of the cerebrospinal fluid (CSF), the brain, or a combination thereof.

In yet another embodiment, the neuroprotective polypeptide concentration in the CSF is within the range of about 5 to about 400 pg/mL.

In some embodiments, the ratio of the steady-state polypeptide concentration in the CFS to the plasma is in the range of about 0.1% to about 5%.

In further embodiments, the neuroprotective polypeptide is selected from the group consisting of SEQ ID NOS: 1-55. For example, the neuroprotective polypeptide may comprise an amino acid sequence selected from SEQ ID NOS: 1-55.

In other embodiments, the exendin-4 analogue is represented by Chemical Formula I or its pharmaceutically acceptable salt:

Xaa1 Xaa2 Xaa3 Xaa4 Xaa5 Xaa6 Xaa7 Xaa8 Xaa9
Xaa10 Xaa11 Xaa12 Xaa13 Xaa14 Xaa15
Xaa16 Xaa17 Ala Xaa19 Xaa20 Xaa21 Xaa22
Xaa23 Xaa24 Xaa25 Xaa26 Xaa27
Xaa28-$Z_1$,                    (Chemical Formula I)

wherein:
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala, or Arg;
Xaa21 is Ala, Leu, or Lys-NHε-R, wherein R is Lys, Arg, or a C1-C10 straight chain or branched alkanoyl;
Xaa22 is Ala, Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
Xaa27 is Ala or Lys;
Xaa28 is Ala or Asn; and
$Z_1$ is —OH, —$NH_2$, Gly-$Z_2$, Gly Gly-$Z_2$, Gly Gly Xaa31-$Z_2$, Gly Gly Xaa31 Ser-$Z_2$, Gly Gly Xaa31 Ser Ser-$Z_2$, Gly Gly Xaa31 Ser Ser Gly-$Z_2$, Gly Gly Xaa31 Ser Ser Gly Ala-$Z_2$, Gly Gly Xaa31 Ser Ser Gly Ala Xaa36-$Z_2$, Gly Gly Xaa31 Ser Ser Gly Ala Xaa36 Xaa37-$Z_2$, Gly Gly Xaa31 Ser Ser Gly Ala Xaa36 Xaa37 Xaa38-$Z_2$, or Gly Gly Xaa31 Ser Ser Gly Ala Xaa36 Xaa37 Xaa38 Xaa39-$Z_2$,
Xaa31, Xaa36, Xaa37, and Xaa38 are independently selected from the group consisting of Pro, homoproline, 3Hyp, 4Hyp, thioproline, N-alkylglycine, N-alkylpentylglycine, or N-alkylalanine, Xaa39 is Ser, or Ty (e.g. Ser), and
$Z_2$ is —OH, or —$NH_2$,
provided that:
no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala; and
when Xaa1 is His, Arg, or Tyr, at least one of Xaa3, Xaa4, and Xaa9 is Ala.

In other embodiments, the exendin-4 analogue is represented by Chemical Formula II or their pharmaceutically acceptable salts:

Xaa1 Xaa2 Xaa3 Xaa4 Xaa5 Xaa6 Xaa7 Xaa8 Xaa9
Xaa10 Xaa11 Xaa12 Xaa13 Xaa14 Xaa15
Xaa16 Xaa17 Ala Xaa19 Xaa20 Xaa21 Xaa22
Xaa23 Xaa24 Xaa25 Xaa26 $X_1$-$Z_1$,    (Chemical Formula II)

wherein:
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHε-R (wherein, R is Lys, Arg, C1-C10 straight chain or branched alkanoyl, or cycloalleylalkanoyl);
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
$X_1$ is Lys Asn, Asn Lys, Lys-NHε-R Asn, Asn Lys-NHε-R, Lys-NHε-R Ala, Ala Lys-NHε-R, wherein R is Lys, Arg, a C1-C10 straight chain or branched alkanoyl, or cycloalkylalkanoyl;
$Z_1$ is —OH, —$NH_2$, Gly-$Z_2$, Gly Gly-$Z_2$, Gly Gly Xaa31-$Z_2$, Gly Gly Xaa31 Ser-$Z_2$, Gly Gly Xaa31 Ser Ser-$Z_2$, Gly Gly Xaa31 Ser Ser Gly-$Z_2$, Gly Gly Xaa31 Ser Ser Gly Ala-$Z_2$, Gly Gly Xaa31 Ser Ser Gly Ala Xaa36-$Z_2$, Gly Gly Xaa31 Ser Ser Gly Ala Xaa36 Xaa37-$Z_2$, Gly Gly Xaa31 Ser Ser Gly Ala Xaa36 Xaa37 Xaa38-$Z_2$, or Gly Gly Xaa31 Ser Ser Gly Ala Xaa36 Xaa37 Xaa38 Xaa39-$Z_2$;
Xaa31, Xaa36, Xaa37, and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr; and
$Z_2$ is —OH or —$NH_2$),
provided that:
no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala; and
when Xaa1 is His, Arg, Tyr, or 4-imidazopropionyl, at least one of Xaa3, Xaa4, and Xaa9 is Ala.

BRIEF DESCRIPTION OF THE DRAWINGS

The accompanying drawings, which are incorporated in and constitute a part of this specification, illustrate (one) several embodiment(s) of the present disclosure and together with the description, serve to explain the principles of the present disclosure.

FIG. 4A. Outline of the study design of Example 2 in which Sprague-Dawley rats were administered PT302 prior to a 6-OHDA unilateral lesion of the medial forebrain bundle.

FIG. 4B. A graph illustrating the methamphetamine-induced (meth-induced) rotational behavior of 6-OHDA rats pre-treated with PT302.

FIG. 11C. A graph illustrating that the results of FIGS. 11A and 11B was not a result of anxiety-like behavior.

FIG. 12A. A graph illustrating that sustained-release Exenatide (PT302: 0.12 and 0.6 mg/kg) results in a high preference for new objects in mTBI-induced mice, as compared to untreated mTBI-induced mice that suffered from visual memory deficits and spent less time near the novel objects; as evaluated at 30 days following mTBI by the Novel Object Recognition paradigm.

FIG. 12B. A graph illustrating that sustained-release Exenatide (PT302: 0.12 and 0.6 mg/kg) ameliorated the mTBI-spatial memory deficit observed in untreated mTBI-induced mice; as evaluated by Y-maze 30 days following mTBI.

FIG. 12C. A graph illustrating that the results of FIGS. 12A and 12B were not a result of anxiety-like behavior.

DETAILED DESCRIPTION

Figure 1A:
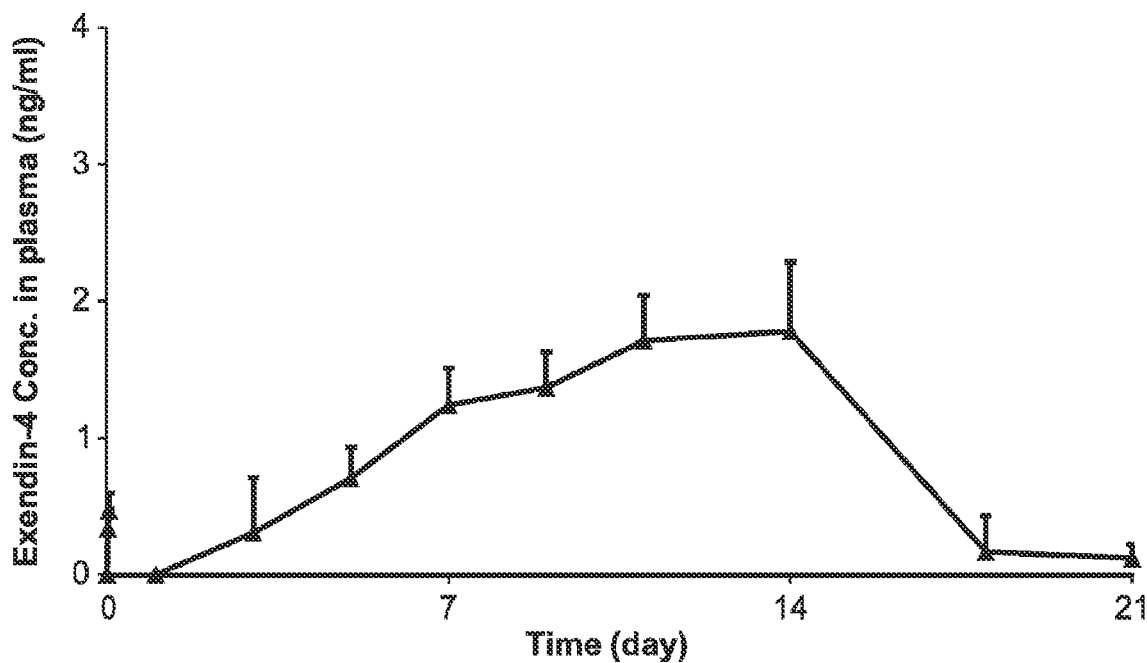
FIG. 1A. A graph illustrating time-dependent exenatide (exendin-4) plasma levels from a single subcutaneous administration of 2 mg/kg sustained-release-Exenatide (PT302) to adult (9 weeks old) male Sprague-Dawley rats.

The present disclosure is based on the surprising and unexpected enhanced delivery of the active ingredients described herein (e.g., GLP-1, exendin and biologically active analogues or derivatives of GLP-1 and exendin). The present description may be understood more readily by reference to the following detailed description of preferred embodiments of the disclosure and the Examples included therein and to the Figures and their previous and following description.

Before the present compounds, compositions, articles, devices, and/or methods are disclosed and described, it is to be understood that the present disclosure is not limited to specific synthetic methods, specific treatment regimens, or to particular purification procedures, as such may, of course, vary. It is also to be understood that the terminology used herein is for the purpose of describing particular embodiments only and is not intended to be limiting.

All publications, patent applications, patents, and other references mentioned herein are incorporated by reference in their entireties, including, e.g. U.S. Pat. Nos. 8,853,160, 8,278,272, 7,576,050, 9,155,702, International Patent Publication WO/2003/011892, and Gu et al. (Clinical Therapeutics. 36(1): 101-114 (2014)) are each incorporated herein by reference in their entireties for all purposes.

As used in the specification and the appended claims, the singular forms "a," "an" and "the" include plural referents unless the context clearly dictates otherwise. Thus, for example, reference to "a polypeptide" includes mixtures of polypeptides, reference to "a pharmaceutical carrier" includes mixtures of two or more such carriers, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. As used herein, "about" refers to the given value±10%.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

As used throughout, by "subject" is meant an individual. In certain embodiments, the subject is a mammal such as a primate. In a particular embodiment, the subject is a human. Thus, the "subject" can include domesticated animals, such as cats, dogs, etc., livestock (e.g., cattle, horses, pigs, sheep, goats, etc.), and laboratory animals (e.g., mouse, rabbit, rat, guinea pig, etc.).

The term "polypeptide" and "peptide" are generally used interchangeably unless the context indicates otherwise. Unless indicated otherwise, both "polypeptide" and "peptide" can refer to naturally occurring or non-naturally occurring amino acids connected by peptide bonds.

The term "steady-state" is used in its ordinary meaning within pharmacokinetics. Briefly, a steady-state concentration, e.g., in plasma or cerebrospinal fluid (CSF) is the concentration in the plasma and CSF when the rate of neuroprotective polypeptide(s) administered is equal to the rate at which the neuroprotective polypeptide(s) are being eliminated by the subject's body. Determining a steady-state concentration of the neuroprotective polypeptide(s) of the present disclosure is routine for one of ordinary skill in the art.

By "isolated polypeptide" or "purified polypeptide" is meant a polypeptide that is substantially free from the materials with which the polypeptide is normally associated in nature or in culture. The polypeptides of the disclosure can be obtained, for example, by extraction from a natural source if available (for example, a mammalian cell), by expression of a recombinant nucleic acid encoding the polypeptide (for example, in a cell or in a cell-free translation system), or by chemically synthesizing the polypeptide. In addition, polypeptide may be obtained by cleaving full length polypeptides. When the polypeptide is a fragment of a larger naturally occurring polypeptide, the isolated polypeptide is shorter than and excludes the full-length, naturally-occurring polypeptide of which it is a fragment.

The present disclosure relates to methods of delivering a neuroprotective polypeptide to at least a portion of a central nervous system (CNS) of a subject. The method comprises administering a controlled-release neuroprotective formulation to the systemic blood circulation of the subject, wherein: the controlled-release neuroprotective formulation includes at least one neuroprotective polypeptide selected from the group consisting of GLP-1, exendin (e.g., exendin-4), or a therapeutically effective GLP-1 or exendin analogue (such as an exendin-4 analogue); the neuroprotective polypeptide binds to and activates a receptor that binds at least one of GLP-1, exendin (e.g., exendin-4), or a combination thereof; and the controlled-release neuroprotective formulation enhances the delivery of the neuroprotective polypeptide across a blood brain barrier (BBB) of the subject to at least a portion of the central nervous system (CNS) relative to a rapid release formulation of the neuroprotective polypeptide.

As shown in FIGS. 1A, 1B, 2, and 3, the controlled-release neuroprotective formulation results in a greater maintenance of plasma levels of Exenatide in an animal model. Furthermore, FIGS. 7B and 8B demonstrate that a controlled-release formulation of Exenatide is a more effective neuroprotective and a more effective neurorestorative formulation/therapeutic than Exenatide alone.

The present disclosure relates to methods for delivering a neuroprotective polypeptide to at least a portion of a central nervous system (CNS) of a subject. The method can comprise: administering to the systemic blood circulation of the subject a therapeutically effective amount of neuroprotective polypeptide by a controlled-release formulation or a device providing a sustained release or delivery of the neuroprotective polypeptide, the neuroprotective polypeptide includes at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof; and wherein the controlled-release neuroprotective formulation or sustained release of the neuroprotective polypeptide enhances the delivery and/or uptake of the neuroprotective polypeptide across a blood-brain barrier (BBB) of the subject to at least a portion of the central nervous system (CNS) relative to a rapid release formulation of the neuroprotective peptide.

The present disclosure also relates to methods of treating a subject with a central nervous system (CNS)-related disease or reducing at least one symptom of a CNS-related disease in a subject in need thereof. The method can comprise: administering to the systemic blood circulation of the subject a therapeutically effective amount of a neuroprotective polypeptide by a controlled-release formulation or a device providing a sustained release or delivery of a neuroprotective polypeptide, the neuroprotective polypeptide includes at least one neuroprotective polypeptide selected from the group consisting of GLP-1, exendin-4, or a therapeutically effective GLP-1 or exendin-4 analogue, the neuroprotective polypeptide binds to and activates a receptor that binds at least one of GLP-1, exendin-4 or a combination thereof; and wherein the controlled-release neuroprotective formulation or a device enhances the delivery of the neuroprotective polypeptide across a blood-brain barrier (BBB) of the subject to at least a portion of the central nervous system (CNS) relative to a rapid release formulation of the neuroprotective polypeptide.

In certain embodiments, the controlled-release formulation is a long acting formulation of the neuroprotective polypeptide. The long acting formulation can comprise a depot formulation for sustained release of the neuroprotective polypeptide. For example, the long acting formulation can comprise a composition for sustained release of the neuroprotective polypeptide (described in greater detail below). In additional embodiments, the controlled-release formulation further comprises a biodegradable polymer with a specific viscosity and coating materials, having bioavailability and sustained release of the neuroprotective polypeptide in an effective concentration for a certain period. In additional embodiments, the controlled-release formulation further comprises a biodegradable polymer with a specific viscosity and coating materials, having bioavailability and sustained release of the neuroprotective polypeptide in an effective concentration for a certain period without an initial burst (e.g., without an initial burst, such as a detrimental initial burst, of the active ingredient) of the active ingredient. In particular embodiments, the controlled-release neuroprotective formulation comprises: a controlled-release microsphere that includes a core with the neuroprotective polypeptide and a biodegradable polymer; and a coating layer that coats the core.

In an embodiment, administering the controlled-release neuroprotective formulation alleviates at least one symptom of at least one CNS-related condition in the subject. For example, the CNS-related condition can be selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy, motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

Administering the controlled-release neuroprotective formulation can comprise injecting the controlled-release neuroprotective formulation. For example, the controlled-release neuroprotective formulation may be injected subcutaneously.

In another embodiment, administering the controlled-release neuroprotective formulation results in a steady-state plasma concentration of the neuroprotective polypeptide that is in a range of about 50 to about 4500 pg/mL. For example, the steady-state plasma concentration of the neuroprotective polypeptide can be in a range of about 50 to about 4500 pg/mL, about 50 to about 4250 pg/mL, about 50 to about 4000 pg/mL, about 50 to about 3750 pg/mL, about 50 to about 3500 pg/mL, about 50 to about 3250 pg/mL, about 50 to about 3000 pg/mL, about 50 to about 2750 pg/mL, about 50 to about 2500 pg/mL, about 50 to about 2250 pg/mL, about 50 to about 2000 pg/mL, about 50 to about 1750 pg/mL, about 50 to about 1500 pg/mL, about 50 to about 1250 pg/mL, about 50 to about 1000 pg/mL, about 50 to about 750 pg/mL, about 50 to about 500 pg/mL, about 50 to about 250 pg/mL, about 250 to about 4500 pg/mL, about 250 to about 4250 pg/mL, about 250 to about 4000 pg/mL, about 250 to about 3750 pg/mL, about 250 to about 3500 pg/mL, about 250 to about 3250 pg/mL, about 250 to about 3000 pg/mL, about 250 to about 2750 pg/mL, about 250 to about 2500 pg/mL, about 250 to about 2250 pg/mL, about 250 to about 2000 pg/mL, about 250 to about 1750 pg/mL, about 250 to about 1500 pg/mL, about 250 to about 1250 pg/mL, about 250 to about 1000 pg/mL, about 250 to about 750 pg/mL, about 250 to about 500 pg/mL, about 500 to about 4500 pg/mL, about 500 to about 4250 pg/mL, about 500 to about 4000 pg/mL, about 500 to about 3750 pg/mL, about 500 to about 3500 pg/mL, about 500 to about 3250 pg/mL, about 500 to about 3000 pg/mL, about 500 to about 2750 pg/mL, about 500 to about 2500 pg/mL, about 500 to about 2250 pg/mL, about 500 to about 2000 pg/mL, about 500 to about 1750 pg/mL, about 500 to about 1500 pg/mL, about 500 to about 1250 pg/mL, about 500 to about 1000 pg/mL, about 500 to about 750 pg/mL, about 750 to about 4500 pg/mL, about 750 to about 4250 pg/mL, about 750 to about 4000 pg/mL, about 750 to about 3750 pg/mL, about 750 to about 3500 pg/mL, about 750 to about 3250 pg/mL, about 750 to about 3000 pg/mL, about 750 to about 2750 pg/mL, about 750 to about 2500 pg/mL, about 750 to about 2250 pg/mL, about 750 to about 2000 pg/mL, about 750 to about 1750 pg/mL, about 750 to about 1500 pg/mL, about 750 to about 1250 pg/mL, about 750 to about 1000 pg/mL, about 1000 to about 4500 pg/mL, about 1000 to about 4250 pg/mL, about 1000 to about 4000 pg/mL, about 1000 to about 3750 pg/mL, about 1000 to about 3500 pg/mL, about 1000 to about 3250 pg/mL, about 1000 to about 3000 pg/mL, about 1000 to about 2750 pg/mL, about 1000 to about 2500 pg/mL, about 1000 to about 2250 pg/mL, about 1000 to about 2000 pg/mL, about 1000 to about 1750 pg/mL, about 1000 to about 1500 pg/mL, about 1000 to about 1250 pg/mL, about 1250 to about 4500 pg/mL, about 1250 to about 4250 pg/mL, about 1250 to about 4000 pg/mL, about 1250 to about 3750 pg/mL, about 1250 to about 3500 pg/mL, about 1250 to about 3250 pg/mL, about 1250 to about 3000 pg/mL, about 1250 to about 2750 pg/mL, about 1250 to about 2500 pg/mL, about 1250 to about 2250 pg/mL, about 1250 to about 2000 pg/mL, about 1250 to about 1750 pg/mL, about 1250 to about 1500 pg/mL, about 1500 to about 4500 pg/mL, about 1500 to about 4250 pg/mL, about 1500 to about 4000 pg/mL, about 1500 to about 3750 pg/mL, about 1500 to about 3500 pg/mL, about 1500 to about 3250 pg/mL, about 1500 to about 3000 pg/mL, about 1500 to about 2750 pg/mL, about 1500 to about 2500 pg/mL, about 1500 to about 2250 pg/mL, about 1500 to about 2000 pg/mL, about 1500 to about 1750 pg/mL, about 1750 to about 4500 pg/mL, about 1750 to about 4250 pg/mL, about 1750 to about 4000 pg/mL, about 1750 to about 3750 pg/mL, about 1750 to about 3500 pg/mL, about 1750 to about 3250 pg/mL, about 1750 to about 3000 pg/mL, about 1750 to about 2750 pg/mL, about 1750 to about 2500 pg/mL, about 1750 to about 2250 pg/mL, about 1750 to about 2000 pg/mL, about 2000 to about 4500 pg/mL, about 2000 to about 4250 pg/mL, about 2000 to about 4000 pg/mL, about 2000 to about 3750 pg/mL, about 2000 to about 3500 pg/mL, about 2000 to about 3250 pg/mL, about 2000 to about 3000 pg/mL, about 2000 to about 2750 pg/mL, about 2000 to about 2500 pg/mL, about 2000 to about 2250 pg/mL, about 2250 to about 4500 pg/mL, about 2250 to about 4250 pg/mL, about 2250 to about 4000 pg/mL, about 2250 to about 3750 pg/mL, about 2250 to about 3500 pg/mL, about 2250 to about 3250 pg/mL, about 2250 to about 3000 pg/mL, about 2250 to about 2750 pg/mL, about 2250 to about 2500 pg/mL, about 2500 to about 4500 pg/mL, about 2500 to about 4250 pg/mL, about 2500 to about 4000 pg/mL, about 2500 to about 3750 pg/mL, about 2500 to about 3500 pg/mL, about 2500 to about 3250 pg/mL, about 2500 to about 3000 pg/mL, about 2500 to about 2750 pg/mL, about 2750 to about 4500 pg/mL, about 2750 to about 4250 pg/mL, about 2750 to about 4000 pg/mL, about 2750 to about 3750 pg/mL, about 2750 to about 3500 pg/mL, about 2750 to about 3250 pg/mL, about 2750 to about 3000 pg/mL, about 3000 to about 4500 pg/mL, about 3000 to about 4250 pg/mL, about 3000 to about 4000 pg/mL, about 3000 to about 3750 pg/mL, about 3000 to about 3500 pg/mL, about 3000 to about 3250 pg/mL, about 3250 to about 4500 pg/mL, about 3250 to about 4250 pg/mL, about 3250 to about 4000 pg/mL, about 3250 to about 3750 pg/mL, about 3250 to about 3500 pg/mL, about 3500 to about 4500 pg/mL, about 3500 to about 4250 pg/mL, about 3500 to about 4000 pg/mL, or about 3500 to about 3750 pg/mL.

The sustained steady-state plasma concentration of the neuroprotective polypeptide, as described above, results in a cumulative increase in the neuroprotective polypeptide concentration in the cerebrospinal fluid (CSF), the brain or a combination thereof in the subject. For example, the neuroprotective polypeptide concentration in the CSF can be within the range of about 5 to about 400 pg/mL or about 10 to about 400 pg/mL. That is, the concentration of the neuroprotective polypeptide in the CSF can be in a range about 10 to about 350 pg/mL, about 10 to about 300 pg/mL, about 10 to about 250 pg/mL, about 10 to about 200 pg/mL, about 10 to about 150 pg/mL, about 10 to about 100 pg/mL, about 10 to about 50 pg/mL, about 50 to about 400 pg/mL, about 50 to about 350 pg/mL, about 50 to about 300 pg/mL, about 50 to about 250 pg/mL, about 50 to about 200 pg/mL, about 50 to about 150 pg/mL, about 50 to about 100 pg/mL, about 100 to about 400 pg/mL, about 100 to about 350 pg/mL, about 100 to about 300 pg/mL, about 100 to about 250 pg/mL, about 100 to about 200 pg/mL, about 100 to about 150 pg/mL, about 150 to about 400 pg/mL, about 150 to about 350 pg/mL, about 150 to about 300 pg/mL, about 150 to about 250 pg/mL, about 150 to about 200 pg/mL, about 200 to about 400 pg/mL, about 200 to about 350 pg/mL, about 200 to about 300 pg/mL, about 200 to about 250 pg/mL, about 250 to about 400 pg/mL, about 250 to about 350 pg/mL, about 250 to about 300 pg/mL, about 300 to about 400 pg/mL, about 300 to about 350 pg/mL, or about 350 to about 400 pg/mL.

In any aspect or embodiment described herein, the ratio of the steady-state polypeptide concentration in the CFS to the plasma can be in the range of about 0.1% to about 5%. For example, the ratio of the steady-state concentration in the CSF to the steady-state concentration of the polypeptide in the plasma can be, in any aspect or embodiment described herein, at least about 0.1%, at least about 0.3%, at least about 0.5%, at least about 0.7%, at least about 0.9%, at least about 1%, at least about 1.1%, at least about 1.2%, at least about 1.5%, at least about 2.0%, about 0.1% to about 5%, about 0.1% to about 4%, about 0.1% to about 3%, about 0.1% to about 2%, about 0.5% to about 5%, about 0.5% to about 4%, about 0.5% to about 3%, about 0.5% to about 2%, about 1% to about 5%, about 1% to about 4%, about 1% to about 3%, about 1% to about 2%, about 2% to about 5%, about 2% to about 4%, about 2% to about 3%, about 3% to about 5%, about 3% to about 4%, or about 4% to about 5%.

In any aspect or embodiment described herein, the percent change in the steady-state level of the neuroprotective polypeptide concentration in the plasma (i.e., percent change once steady-state is achieved) may be no greater than about 80% (e.g., no greater than about 50%). For example, the percent change in the neuroprotective polypeptide concentration in the plasma may be no greater than about 80% (e.g., no greater than about 50%) when re-administered after a steady-state plasma level/concentration is achieved (e.g., the neuroprotective polypeptide concentration in the plasma may be at a steady state after about 2, about 3, about 4, about 5, or about 6 weeks of the first administration). For example, the percent change in the steady-state plasma concentration of the neuroprotective polypeptide after steady-state is achieved is no greater than about 80%, about 79%, about 78%, about 77%, about 76%, about 75%, about 74%, about 73%, about 72%, about 71%, about 70%, about 69, about 68%, about 67%, about 66%, about 65%, about 64%, about 63%, about 62%, about 61%, about 60%, about 59%, about 58%, about 57%, about 56%, about 55%, about 54%, about 53%, about 52%, about 51%, about 50%, about 49%, about 48%, about 47%, about 46%, about 45%, about 44%, about 43%, about 42%, about 41%, about 40%, about 39%, about 39%, about 37%, about 36%, about 35%, about 34%, about 33%, about 32%, about 31%, about 30%, about 29%, about 28%, about 27%, about 26%, about 25%, about 24%, about 23%, about 22%, about 21%, about 20%, about 19%, about 18%, about 17%, about 16%, about 15%, %, at 14%, about 13%, about 12%, about 11%, about 10%, about 9%, about 8%, about 7%, about 6%, or about 5%, e.g. when the neuroprotective polypeptide is re-administered within about 28 days (e.g., within about 7, 14, or about 21 days) of a previous neuroprotective polypeptide administration (e.g., administered about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, or about 28 days after a previous neuroprotective polypeptide(s) administration).

In any aspect or embodiment described herein, the formulation is administered once every about 7 to about 28 days (e.g., about 7 to about 21 days or about 7 days to about 14 days). For example, the formulation can be administered a plurality, wherein each administration is about 7 to about 28 days (e.g., once every about 7, about 8, about 9, about 10, about 11, about 12, about 13, about 14, about 15, about 16, about 17, about 18, about 19, about 20, about 21, about 22, about 23, about 24, about 25, about 26, about 27, or about 28 days) apart (e.g., a subsequent administration is about 7 to about 28 days after a previous administration). The formulation can be administered, in any aspect or embodiment herein, a plurality of times, wherein the formulation is administered at an interval of about 7 to about 28 days (e.g., about 7, about 8, about 9, about 10, about 11, about 12, about 13, about 14, about 15, about 16, about 17, about 18, about 19, about 20, or about 21 day intervals (i.e., once every about 7, about 8, about 9, about 10, about 11, about 12, about 13, about 14, about 15, about 16, about 17, about 18, about 19, about 20, about 21, about 22, about 23, about 24, about 26, about 27, or about 28 day interval).

In an additional aspect, a method of treating a subject with a central nervous system (CNS)-related disease or reducing at least one symptom of a CNS-related disease in a subject in need thereof is provided. The method comprises administering to the subject a therapeutically effective amount of a controlled-release neuroprotective formulation to the systemic blood circulation of the subject, wherein: the controlled-release neuroprotective formulation includes at least one neuroprotective polypeptide selected from the group consisting of GLP-1, exendin (e.g. exendin-4), or a therapeutically effective GLP-1 or exendin (e.g. exendin-4) analogue; the neuroprotective polypeptide binds to and activates a receptor that binds at least one of GLP-1, exendin (e.g. exendin-4) or a combination thereof; and the controlled-release neuroprotective formulation enhances the delivery of the neuroprotective polypeptide across a blood-brain barrier (BBB) of the subject to at least a portion of the central nervous system (CNS) relative to the neuroprotective polypeptide alone.

In a particular embodiment, administering the controlled-release neuroprotective formulation alleviates at least one symptom of at least one CNS-related condition in the subject. For example, the CNS condition is selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy, motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

In further embodiments, administering the controlled-release neuroprotective formulation comprises injecting the controlled-release neuroprotective formulation to the subject. For example, administering the controlled-release neuroprotective formulation comprising subcutaneously injecting the controlled-release neuroprotective formulation to the subject. In additional embodiments, the controlled-release formulation further comprises a biodegradable polymer with a specific viscosity and coating materials, having bioavailability and sustained release of the neuroprotective polypeptide in an effective concentration for a certain period. In any aspect or embodiment described herein, the controlled-release formulation has bioavailability and sustained release of the neuroprotective polypeptide in an effective concentration for a certain period without an initial burst (e.g. a detrimental initial burst) of the active ingredient. In particular embodiments, the controlled-release neuroprotective formulation comprises: a controlled-release microsphere that includes a core with the neuroprotective polypeptide and a biodegradable polymer; and a coating layer that coats the core.

In additional embodiments, administering the controlled-release formulation results in a steady-state plasma concentration of the neuroprotective polypeptide that is in a range as described above, e.g. about 50 to about 4500 pg/mL.

In some embodiments, administering the controlled-release formulation results in a cumulative increase in the neuroprotective polypeptide concentration in at least one of the cerebrospinal fluid (CSF), the brain, or a combination thereof.

In a further aspect, the disclosure provides a method for delivering a neuroprotective polypeptide to at least a portion of a central nervous system (CNS) of a subject. The method comprises: providing a sustained delivery to the systemic blood circulation of the subject at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof; and wherein the controlled-release neuroprotective formulation enhances the delivery and/or uptake of the neuroprotective polypeptide across a blood-brain barrier (BBB) of the subject to at least a portion of the CNS relative to a rapid release formulation of the neuroprotective peptide.

In yet another aspect, the disclosure provides a method of treating a subject with a CNS-related disease or reducing at least one symptom of a CNS-related disease in a subject in need thereof. The method comprises: providing a sustained delivery to the systemic blood circulation of the subject at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4 or a combination thereof; and wherein the controlled-release neuroprotective formulation enhances the delivery of the neuroprotective polypeptide across a BBB of the subject to at least a portion of the CNS relative to a rapid release formulation of the neuroprotective polypeptide. In any aspect or embodiment described herein, providing the sustained release of the neuroprotective polypeptide or polypeptides includes administering the neuroprotective polypeptide or polypeptides with a device (e.g., a pump, a mini-pump, an osmotic pump, an osmotic delivery device, an infusion pump, an intravenous administration device, a peristaltic pump, a miniature infusion pump, or the like).

The neuroprotective polypeptide or polypeptides (e.g., in the controlled-release neuroprotective formulation) may be administered at a rate of about 0.5 pM/kg/min to about 35 pM/kg/min (e.g., about 3 pM/kg/min to about 17.5 pM/kg/min). For example, the neuroprotective polypeptide or polypeptides may be administered at a rate of about 0.5 pM/kg/min to about 35 pM/kg/min, about 0.5 pM/kg/min to about 35 pM/kg/min, about 0.5 pM/kg/min to about 32.5 pM/kg/min, about 0.5 pM/kg/min to about 30 pM/kg/min, about 0.5 pM/kg/min to about 27.5 pM/kg/min, about 0.5 pM/kg/min to about 25 pM/kg/min, about 0.5 pM/kg/min to about 22.5 pM/kg/min, about 0.5 pM/kg/min to about 20 pM/kg/min, about 0.5 pM/kg/min to about 17.5 pM/kg/min, about 0.5 pM/kg/min to about 15 pM/kg/min, about 0.5 pM/kg/min to about 12.5 pM/kg/min, about 0.5 pM/kg/min to about 10 pM/kg/min, about 1.5 pM/kg/min to about 35 pM/kg/min, about 1.5 pM/kg/min to about 35 pM/kg/min, about 1.5 pM/kg/min to about 32.5 pM/kg/min, about 1.5 pM/kg/min to about 30 pM/kg/min, about 1.5 pM/kg/min to about 27.5 pM/kg/min, about 1.5 pM/kg/min to about 25 pM/kg/min, about 1.5 pM/kg/min to about 22.5 pM/kg/min, about 1.5 pM/kg/min to about 20 pM/kg/min, about 1.5 pM/kg/min to about 17.5 pM/kg/min, about 1.5 pM/kg/min to about 15 pM/kg/min, about 1.5 pM/kg/min to about 12.5 pM/kg/min, about 1.5 pM/kg/min to about 10 pM/kg/min, about 2.5 pM/kg/min to about 35 pM/kg/min, about 2.5 pM/kg/min to about 35 pM/kg/min, about 2.5 pM/kg/min to about 32.5 pM/kg/min, about 2.5 pM/kg/min to about 30 pM/kg/min, about 2.5 pM/kg/min to about 27.5 pM/kg/min, about 2.5 pM/kg/min to about 25 pM/kg/min, about 2.5 pM/kg/min to about 22.5 pM/kg/min, about 2.5 pM/kg/min to about 20 pM/kg/min, about 2.5 pM/kg/min to about 17.5 pM/kg/min, about 2.5 pM/kg/min to about 15 pM/kg/min, about 2.5 pM/kg/min to about 12.5 pM/kg/min, about 2.5 pM/kg/min to about 10 pM/kg/min, about 5 pM/kg/min to about 35 pM/kg/min, about 5 pM/kg/min to about 35 pM/kg/min, about 5 pM/kg/min to about 32.5 pM/kg/min, about 5 pM/kg/min to about 30 pM/kg/min, about 5 pM/kg/min to about 27.5 pM/kg/min, about 5 pM/kg/min to about 25 pM/kg/min, about 5 pM/kg/min to about 22.5 pM/kg/min, about 5 pM/kg/min to about 20 pM/kg/min, about 5 pM/kg/min to about 17.5 pM/kg/min, about 5 pM/kg/min to about 15 pM/kg/min, about 5 pM/kg/min to about 12.5 pM/kg/min, about 5 pM/kg/min to about 10 pM/kg/min, about 10 pM/kg/min to about 35 pM/kg/min, about 10 pM/kg/min to about 35 pM/kg/min, about 10 pM/kg/min to about 32.5 pM/kg/min, about 10 pM/kg/min to about 30 pM/kg/min, about 10 pM/kg/min to about 27.5 pM/kg/min, about 10 pM/kg/min to about 25 pM/kg/min, about 10 pM/kg/min to about 22.5 pM/kg/min, about 10 pM/kg/min to about 20 pM/kg/min, about 10 pM/kg/min to about 17.5 pM/kg/min, about 15 pM/kg/min to about 35 pM/kg/min, about 15 pM/kg/min to about 35 pM/kg/min, about 15 pM/kg/min to about 32.5 pM/kg/min, about 15 pM/kg/min to about 30 pM/kg/min, about 15 pM/kg/min to about 27.5 pM/kg/min, about 15 pM/kg/min to about 25 pM/kg/min, about 20 pM/kg/min to about 35 pM/kg/min, about 20 pM/kg/min to about 35 pM/kg/min, about 20 pM/kg/min to about 32.5 pM/kg/min, about 20 pM/kg/min to about 30 pM/kg/min, or about 25 pM/kg/min to about 35 pM/kg/min.

In any aspect or embodiment described herein, the controlled-release formulation or the neuroprotective polypeptide or polypeptides may be administered via a device. For example, the device may be an implantable device that contains and delivers the controlled-release formulation or the neuroprotective polypeptide or polypeptides. The device may be a pump, a mini-pump, an osmotic pump, an osmotic delivery device, an infusion pump, an intravenous administration device, a peristaltic pump, a miniature infusion pump, or the like. In any aspect or embodiment described herein, the device may be an implantable device, which may provide constant flow, adjustable flow, or programmable flow of the controlled-release formulation or the neuroprotective polypeptide or polypeptides. For example, an osmotic delivery device as described in U.S. Pat. No. 8,298,561 B2 or U.S. Pat. No. 8,940,316 B2, both of which are incorporated herein by reference in their entireties.

The term "osmotic delivery device" as used herein refers to a device used for delivery of one or more beneficial agent (e.g., the neuroprotective polypeptide or polypeptides or the controlled-release formulation) to a subject, wherein the device comprises, for example, a reservoir (made, for example, from a titanium alloy) having a lumen that contains a suspension formulation (e.g., comprising the neuroprotective polypeptide or polypeptides or the controlled-release formulation) and an osmotic agent formulation. A piston assembly positioned in the lumen isolates the suspension formulation from the osmotic agent formulation. A semipermeable membrane positioned at a first distal end of the reservoir adjacent the osmotic agent formulation, as well as a flow modulator (which defines a delivery orifice through which the suspension formulation exits the device) that is positioned at a second distal end of the reservoir adjacent the suspension formulation. The osmotic delivery device or osmotic pump may be implanted within the subject, for example, subcutaneously (e.g., in the inside, outside, or back of the upper arm; or in the abdominal area).

The neuroprotective polypeptide or polypeptides or the controlled-release formulation described herein may be administered via a device to provide sustained delivery of the neuroprotective polypeptide or polypeptides or the controlled-release formulation over an extended period of time, such as over weeks, months, or up to about one year. Such a device, which may be an implantable device, is capable of delivering the neuroprotective polypeptide or polypeptides or the controlled-release formulation at a desired flow rate over a desired period of time. The neuroprotective polypeptide or polypeptides or the controlled-release formulation may be loaded into the implantable, drug delivery device by conventional techniques.

The neuroprotective polypeptide or polypeptides or the controlled-release formulation may be delivered, for example, using an osmotically, mechanically, electromechanically, or chemically driven device. In any aspect or embodiment described herein, the neuroprotective polypeptide or polypeptides or the controlled-release formulation is delivered at a flow rate that is therapeutically effective to the subject in need of treatment by the neuroprotective polypeptide(s).

The neuroprotective polypeptide or polypeptides or the controlled-release formulation may be delivered over a period ranging from more than about one week to about one year or more (e.g., for about one month to about a year or more or for about three months to about a year or more). The device may include a reservoir having at least one orifice through which the neuroprotective polypeptide or polypeptides or the controlled-release formulation is delivered. The neuroprotective polypeptide or polypeptides or the controlled-release formulation may be stored within the reservoir. In any aspect or embodiment described herein, the device is an osmotic delivery device, which may be an implantable device, wherein delivery of the neuroprotective polypeptide or polypeptides or the controlled-release formulation is osmotically driven. Some osmotic delivery devices or osmotic pumps and their component parts have been described, for example, the DUROS® delivery device or similar devices (see, e.g., U.S. Pat. Nos. 5,609,885; 5,728,396; 5,985,305; 5,997,527; 6,113,938; 6,132,420; 6,156,331; 6,217,906; 6,261,584; 6,270,787; 6,287,295; 6,375,978; 6,395,292; 6,508,808; 6,544,252; 6,635,268; 6,682,522; 6,923,800; 6,939,556; 6,976,981; 6,997,922; 7,014,636; 7,207,982; 7,112,335; 7,163,688; U.S. Patent Application Publication Nos. 2005-0175701, 2007-0281024, and 2008-0091176, all of which are incorporated herein by reference in their entireties).

The DUROS® delivery device typically consists of a cylindrical reservoir which contains the osmotic engine, piston, and drug formulation. The reservoir is capped at one end by a controlled-rate water-permeable membrane and capped at the other end by a diffusion moderator through which drug formulation is released from the drug reservoir. The piston separates the drug formulation from the osmotic engine and utilizes a seal to prevent the water in the osmotic engine compartment from entering the drug reservoir. The diffusion moderator is designed, in conjunction with the drug formulation (e.g., the neuroprotective polypeptide or polypeptides or the controlled-release formulation), to prevent body fluid from entering the drug reservoir through the orifice.

The DUROS® device releases a therapeutic agent at a predetermined rate based on the principle of osmosis. Extracellular fluid enters the DUROS® device through a semipermeable membrane directly into a salt engine that expands to drive the piston at a slow and even delivery rate. Movement of the piston forces the drug formulation (e.g., the neuroprotective polypeptide or polypeptides or the controlled-release formulation) to be released through the orifice or exit port at a predetermined sheer rate. In any aspect or embodiment of the present invention, the reservoir of the DUROS® device is load with the neuroprotective polypeptide(s) or the controlled-release formulation, wherein the device is capable of delivering the neuroprotective polypeptide(s) or the controlled-release formulation to a subject over an extended period of time (e.g., about 1, about 2, about 3, about 4, about 5, about 6, about 7, about 8, about 9, about 10, about 11, or about 12 months) at a predetermined, therapeutically effective delivery rate.

Any implantable, device may be used in the practice of the present disclosure and may include regulator-type implantable pumps that provide constant flow, adjustable flow, or programmable flow of the compound.

The amount of the neuroprotective polypeptide(s) or the controlled-release formulation employed in the delivery device of the disclosure is that amount necessary to deliver a therapeutically effective amount of the agent to achieve the desired therapeutic result. In practice, this will vary depending upon such variables, for example, as the particular agent, the site of delivery, the severity of the condition, and the desired therapeutic effect. Typically, for an osmotic delivery device, the volume of a beneficial agent chamber comprising neuroprotective polypeptide(s) or the controlled-release formulation is between about 100 µl to about 1000 µl (e.g., about 120 µl and about 500 µl or about 150 µl and about 200 µl).

In any aspect or embodiment described herein, the osmotic delivery device is implanted within the subject, for example, subcutaneously. The device(s) can be inserted in either or both arms (e.g., in the inside, outside, or back of the upper arm) or into the abdomen. For example, the device may be implanted under the abdominal skin in the area extending below the ribs and above the belt line. To provide a number of locations for insertion of one or more osmotic delivery device within the abdomen, the abdominal wall can be divided into 4 quadrants as follows: the upper right quadrant extending 5-8 centimeters below the right ribs and about 5-8 centimeters to the right of the midline, the lower right quadrant extending 5-8 centimeters above the belt line and 5-8 centimeters to the right of the midline, the upper left quadrant extending 5-8 centimeters below the left ribs and about 5-8 centimeters to the left of the midline, and the lower left quadrant extending 5-8 centimeters above the belt line and 5-8 centimeters to the left of the midline. This provides multiple available locations for implantation of one or more devices on one or more occasions.

In other embodiments, administering the controlled-release neuroprotective formulation or providing a sustained delivery of the neuroprotective polypeptide alleviates at least one symptom of at least one CNS-related condition in the subject selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy, motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

In any aspect or embodiment described herein, administering the controlled-release formulation or providing the sustained release of the neuroprotective polypeptide results in a steady-state plasma concentration of the neuroprotective polypeptide that is in a range of about 50 to about 4500 pg/mL.

In any aspect or embodiment described herein, administering the controlled-release formulation or providing the sustained release of the neuroprotective polypeptide results in a cumulative increase in the neuroprotective polypeptide concentration in at least one of the cerebrospinal fluid (CSF), the brain, or a combination thereof.

Neuroprotective Polypeptides

The neuroprotective polypeptide may have an amino acid selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, or SEQ ID NO: 55. The neuroprotective polypeptide may comprise an amino acid sequence selected from SEQ ID NOS: 1-55. Furthermore, the neuroprotective polypeptide may consist of an amino acid sequence selected from SEQ ID NOS: 1-55.

By "analogue of GLP-1 or exendin-4" it is meant modified GLP-1 and/or exendin amino acid sequences that show agonist properties (i.e., show one or more biological activities of GLP-1 or exendin-4). Such modifications include chimeric polypeptides that include one or more amino acid residues present in GLP-1 and one or more amino acid residues present in exendin-4. The modifications also include truncations of either GLP-1 or exendin-4 or the chimeric polypeptides. For example, a truncated chimeric polypeptide is exendin-4 7-36 with the G at position 36 replaced with the R in position 36 of GLP-1. The polypeptides of the present disclosure include one or more additional amino acids (i.e., insertions or additions), deletions of amino acids, or substitutions in the amino acid sequence of GLP-1 or exendin-4 without appreciable loss of functional activity as compared to GLP-1 or exendin-4. For example, the deletion can consist of amino acids that are not essential to the presently defined differentiating activity and the substitution(s) can be conservative (i.e., basic, hydrophilic, or hydrophobic amino acids substituted for the same) or non-conservative. A conservative substitution is one in which the substituted amino acid has similar structural or chemical properties with the corresponding amino acid in the reference sequence. By way of example, conservative amino acid substitutions involve substitution of one aliphatic or hydrophobic amino acid, e.g. alanine, valine, leucine and isoleucine, with another; substitution of one hydroxyl-containing amino acid, e.g. serine and threonine, with another; substitution of one acidic residue, e.g. glutamic acid or aspartic acid, with another; replacement of one amide-containing residue, e.g. asparagine and glutamine, with another; replacement of one aromatic residue, e.g. phenylalanine and tyrosine, with another; replacement of one basic residue, e.g. lysine, arginine and histidine, with another; and replacement of one small amino acid, e.g., alanine, serine, threonine, methionine, and glycine, with another. Thus, it is understood that, where desired, modifications and changes may be made in the amino acid sequence of GLP-1 and exendin-4, and a protein having like characteristics still obtained. Various changes may be made in the amino acid sequence of the GLP-1 or exendin-4 amino acid sequence (or underlying nucleic acid sequence) without appreciable loss of biological utility or activity and possibly with an increase in such utility or activity.

The term "fragments" or "truncations" as used herein regarding GLP-1 or exendin-4 or polypeptides having amino acid sequences substantially homologous thereto means a polypeptide sequence of at least 5 contiguous amino acids of either GLP-1, exendin-4, or polypeptides having amino acid sequences substantially homologous thereto, wherein the polypeptide sequence has an insulinotropic function.

Other modifications include D-enantiomers, in which at least one naturally occurring L-configuration of an amino acid residue is replaced by the D-configuration of the amino acid residue.

The present disclosure contemplates the use of a spacer, such as a lateral spacer. The term "lateral spacer" is defined as a compound that is incorporated within the amino acid sequence by chemical bonds, whereby the compound increases the distance between two or more amino acid residues in order to reduce or eliminate the cleavage (e.g., by DPP 1V) of the amino acid sequence at or near that position. For example, in the sequence A-X-B, where A and B are amino acid residues and X is the lateral spacer, cleavage of the sequence by an enzyme is reduced or eliminated when compared to the sequence in the absence of the lateral spacer (A-B). For example, 1 to 4 compounds can be incorporated into the amino acid sequence as the lateral spacer. Thus, 1, 2, 3, or 4 compounds are inserted in various embodiments.

In general, the lateral spacer is any compound that can form a peptide bond with an amino acid, i.e., contains at least one amino group and at least one carboxyl group ($CO_2$), where the carboxyl group can be a carboxylic acid or the ester or salt thereof. In one embodiment, the lateral spacer has the formula $H_2N-R^1-CO_2H$ (I), wherein $R^1$ comprises a substituted or unsubstituted, branched or straight chain $C_1$ to $C_{20}$ alkyl group, alkenyl group, or alkynyl group; a substituted or unsubstituted $C_3$ to $C_8$ cycloalkyl group; a substituted or unsubstituted $C_6$ to $C_{20}$ aryl group; or substituted or unsubstituted $C_4$ to $C_{20}$ heteroaryl group. In another embodiment, $R^1$ can be represented by the formula $(CH_2)_n$, where n is from 1 to 10. In an embodiment, $R^1$ is $(CH_2)_3$(3-aminopropionic acid) or $(CH_2)_5$(6-aminohexanoic acid).

The present disclosure provides a method that includes the administration of a controlled-release formulation comprising at least one neuroprotective polypeptide. The polypeptide can comprise a modified GLP-1 or exendin (e.g. exendin-4) sequence, or an analogue or derivative thereof, with a spacer between the amino acid residues comparable to residues 7 and 8 (designated in the case of GLP-1 with a Aha spacer, for example, "GLP-1 Aha$^8$") or residues 8 and 9 (designated in the case of GLP-1 with a Aha spacer, for example, "GLP-1Aha$^9$") of GLP-1. The lateral spacer, in one embodiment, is one or more aminoproprionic acid residues. In one embodiment, the spacer is a 6-aminohexanoic acid spacer and the 6-aminohexanoic acid spacer comprises less than four 6-aminohexanoic acid residues. The polypeptide, for example, can comprise GLP-1 7-36 with one or more 6-aminohexanoic acid residues between residues 7 and 8 (i.e., GLP-1 Aha$^8$) or can comprise GLP-1 7-36 with one or more 6-aminohexanoic acid residues between residues 8 and 9. The polypeptide can comprise GLP-1 7-36 with two or more 6-aminohexanoic acid residues between residues 7 and 8 (i.e., GLP-1 Aha$^8$) or can comprise GLP-1 7-36 with two or more 6-aminohexanoic acid residues between residues 8 and 9. The polypeptide, for example, can comprise GLP-1 7-36 with three or more 6-aminohexanoic acid residues between residues 7 and 8 (i.e., GLP-1 Aha$^8$) or can comprise GLP-1 7-36 with three or more 6-aminohexanoic acid residues between residues 8 and 9.

In other embodiments, the polypeptide of the present disclosure has an insulinotropic effect that is comparable to the effect of an equimolar amount of GLP-1 or, in an embodiment, an insulinotropic effect that is comparable to the effect of an equimolar amount of exendin-4. By "comparable to the effect" it is meant an effect that is within about 10-15% of the effect of GLP-1 or exendin-4. In another embodiment, the polypeptide has an insulinotropic effect that exceeds the insulinotropic effect of either GLP-1 or exendin-4. By "exceeding the effect" of GLP-1 or exendin-4 it is meant an increase in insulinotropic effect compared to GLP-1 or exendin-4, such as an increase that is greater than about 10% of the effect of GLP-1 or exendin-4. Thus, in an embodiment, the polypeptide of the present disclosure is as potent as GLP-1 or exendin-4, and in another embodiment, the polypeptide of the present disclosure is more potent that GLP-1 and, optionally, more potent than exendin-4. In other embodiments, the polypeptide of the present disclosure is longer acting than GLP-1. In a further embodiment, the polypeptide is at least as long acting as exendin-4. In other embodiments, the polypeptide is longer acting than exendin-4. By "longer acting" it is meant that the polypeptide is more resistant than GLP-1 or exendin-4 to at least one degradative enzyme. For example, the polypeptide of the present disclosure is more resistant to degradation by the enzyme dipeptidyl peptidase-4 (DPPIV) than is GLP-1 and, optionally, more resistant than exendin-4. Such resistance to one or more degradative enzymes can be assessed directly by detecting the amount of degradation products (e.g., the amount of N-terminal degradation products) or the amount of uncleaved polypeptide. Alternatively, the resistance to one or more degradative enzymes can be detected indirectly by assessing the reduction in insulinotropic effect over time following administration of a polypeptide of the disclosure. For example, as the degradative enzymes cleave the polypeptides of the disclosure, plasma insulin levels should decline after a single administration. In additional embodiments, this decline would be slower than for GLP-1 and/or perhaps even slower than for exendin-4.

The polypeptides of the disclosure can be prepared using any of a number of chemical polypeptide synthesis techniques well known to those of ordinary skill in the art including solution methods and solid phase methods. Solid phase synthesis in which the C-terminal amino acid of the polypeptide sequence is attached to an insoluble support followed by sequential addition of the remaining amino acids in the sequence is one synthetic method for preparing the polypeptides. Techniques for solid phase synthesis are described by Merrifield et al., *J. Am. Chem. Soc.* 85:2149-2156 (1963). Many automated systems for performing solid phase peptide synthesis are commercially available.

Solid phase synthesis is started from the carboxy-terminal end (i.e., the C-terminus) of the polypeptide by coupling a protected amino acid via its carboxyl group to a suitable solid support. The solid support used is not a critical feature provided that it is capable of binding to the carboxyl group while remaining substantially inert to the reagents utilized in the peptide synthesis procedure. For example, a starting material can be prepared by attaching an amino-protected amino acid via a benzyl ester linkage to a chloromethylated resin or a hydroxymethyl resin or via an amide bond to a benzhydrylamine (BHA) resin or p-methylbenzhydrylamine (MBHA) resin. Materials suitable for use as solid supports are well known to those of skill in the art and include, but are not limited to, the following: halomethyl resins, such as chloromethyl resin or bromomethyl resin; hydroxymethyl resins; phenol resins, such as 4-(a-[2,4-dimethoxyphenyl]-Fmoc-aminomethyl)phenoxy resin; tert-alkyloxycarbonyl-hydrazidated resins; and the like. Such resins are commercially available and their methods of preparation are known to those of ordinary skill in the art.

The acid form of the peptides may be prepared by the solid phase peptide synthesis procedure using a benzyl ester resin as a solid support. The corresponding amides may be produced by using benzhydrylamine or methylbenzhydrylamine resin as the solid support. Those skilled in the art will recognize that when the BHA or MBHA resin is used, treatment with anhydrous hydrofluoric acid to cleave the peptide from the solid support produces a peptide having a terminal amide group.

The α-amino group of each amino acid used in the synthesis should be protected during the coupling reaction to prevent side reactions involving the reactive α-amino function. Certain amino acids also contain reactive side-chain functional groups (e.g. sulfhydryl, amino, carboxyl, hydroxyl, etc.) which must also be protected with appropriate protecting groups to prevent chemical reactions from occurring at those sites during the peptide synthesis. Protecting groups are well known to those of skill in the art. See, for example, The Peptides: Analysis, Synthesis, Biology, Vol. 3: Protection of Functional Groups in Peptide Synthesis (Gross and Meienhofer (eds.), Academic Press, N.Y. (1981)).

A properly selected α-amino protecting group will render the α-amino function inert during the coupling reaction, will be readily removable after coupling under conditions that will not remove side chain protecting groups, will not alter the structure of the peptide fragment, and will prevent racemization upon activation immediately prior to coupling. Similarly, side-chain protecting groups must be chosen to render the side chain functional group inert during the synthesis, must be stable under the conditions used to remove the α-amino protecting group, and must be removable after completion of the peptide synthesis under conditions that will not alter the structure of the peptide.

Coupling of the amino acids may be accomplished by a variety of technique known to those of skill in the art. Typical approaches involve either the conversion of the amino acid to a derivative that will render the carboxyl group more susceptible to reaction with the free N-terminal amino group of the peptide fragment, or use of a suitable coupling agent such as, for example, N,N'-dicyclohexylcarbodiimide (DCC) or N,N'-diisopropylcarbodiimide (DIPCDI). Frequently, hydroxybenzotriazole (HOBt) is employed as a catalyst in these coupling reactions.

Generally, synthesis of the peptide is commenced by first coupling the C-terminal amino acid, which is protected at the N-amino position by a protecting group such as fluorenylmethyloxycarbonyl (Fmoc), to a solid support. Prior to coupling of Fmoc-Asn, the Fmoc residue has to be removed from the polymer. Fmoc-Asn can, for example, be coupled to the 4-(a-[2,4-dimethoxyphenyl]-Fmoc-amino-methyl) phenoxy resin using N,N'-dicyclohexylcarbodiimide (DCC) and hydroxybenzotriazole (HOBt) at about 25° C. for about two hours with stirring. Following the coupling of the Fmoc-protected amino acid to the resin support, the α-amino protecting group is removed using 20% piperidine in DMF at room temperature.

After removal of the α-amino protecting group, the remaining Fmoc-protected amino acids are coupled stepwise in the desired order. Appropriately protected amino acids are commercially available from a number of suppliers (e.g., Novartis (Switzerland) or Bachem (Torrance, Calif.)). As an alternative to the stepwise addition of individual amino acids, appropriately protected peptide fragments consisting of more than one amino acid may also be coupled to the "growing" peptide. Selection of an appropriate coupling reagent, as explained above, is well known to those of skill in the art.

Each protected amino acid or amino acid sequence is introduced into the solid phase reactor in excess and the coupling is carried out in a medium of dimethylformamide (DMF), methylene chloride ($CH_2Cl_2$), or mixtures thereof. If coupling is incomplete, the coupling reaction may be repeated before deprotection of the N-amino group and addition of the next amino acid. Coupling efficiency may be monitored by a number of means well known to those of skill in the art. A method of monitoring coupling efficiency may be by the ninhydrin reaction. Peptide synthesis reactions may be performed automatically using a number of commercially available peptide synthesizers such as the Biosearch 9500™ synthesizer (Biosearch, San Raphael, Calif.).

The peptide can be cleaved and the protecting groups removed by stirring the insoluble carrier or solid support in anhydrous, liquid hydrogen fluoride (HF) in the presence of anisole and dimethylsulfide at about 0° C. for about 20 to 90 minutes, e.g. 60 minutes; by bubbling hydrogen bromide (HBr) continuously through a 1 mg/10 mL suspension of the resin in trifluoroacetic acid (TFA) for 60 to 360 minutes at about room temperature, depending on the protecting groups selected; or by incubating the solid support inside the reaction column used for the solid phase synthesis with 90% trifluoroacetic acid, 5% water and 5% triethylsilane for about 30 to 60 minutes. Other deprotection methods well known to those of skill in the art may also be used.

The peptides can be isolated and purified from the reaction mixture by means of peptide purification well known to those of skill in the art. For example, the peptides may be purified using known chromatographic procedures such as reverse phase HPLC, gel permeation, ion exchange, size exclusion, affinity, partition, or countercurrent distribution.

The neuroprotective polypeptides can also be prepared by other means including, for example, recombinant techniques. Examples of appropriate cloning and sequencing techniques, and instructions sufficient to direct persons of skill through many cloning exercises are found in Sambrook et al. (1989) Molecular Cloning—A Laboratory Manual (2nd ed.) Vol. 1-3, Cold Spring Harbor Laboratory, Cold Spring Harbor Press, NY, (Sambrook).

For example, the exendin derivative or derivatives utilized in the controlled-release formulation may be a compound represented by Chemical Formula I, or its pharmaceutically acceptable salt:

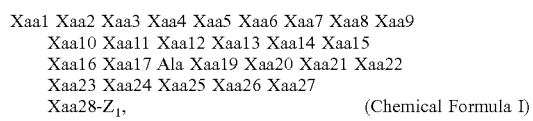

(Chemical Formula I)

wherein:

Xaa1 is His, Arg, Tyr, Ala, Norval, Val, Norleu, or 4-imidazopropionyl;

Xaa2 is Ser, Gly, Ala, or Thr;

Xaa3 is Ala, Asp, or Glu;

Xaa4 is Ala, Norval, Val, Norleu, or Gly;

Xaa5 is Ala or Thr;

Xaa6 is Ala, Phe, Tyr, or naphthylalanine;

Xaa7 is Thr or Ser;

Xaa8 is Ala, Ser, or Thr;

Xaa9 is Ala, Norval, Val, Norleu, Asp, or Glu;

Xaa10 is Ala, Leu, Ile, Val, pentylglycine, or Met;

Xaa11 is Ala or Ser;

Xaa12 is Ala or Lys;

Xaa13 is Ala or Gln;

Xaa14 is Ala, Leu, Ile, pentylglycine, Val, or Met;

Xaa15 is Ala or Glu;

Xaa16 is Ala or Glu;

Xaa17 is Ala or Glu;

Xaa19 is Ala or Val;

Xaa20 is Ala, or Arg;

Xaa21 is Ala, Leu, or Lys-NHε-R, wherein R is Lys, Arg, or a C1-C10 straight chain or branched alkanoyl;

Xaa22 is Ala, Phe, Tyr, or naphthylalanine;

Xaa23 is Ile, Val, Leu, pentylglycine, tert-butylglycine, or Met;

Xaa24 is Ala, Glu, or Asp;

Xaa25 is Ala, Trp, Phe, Tyr, or naphthylalanine;

Xaa26 is Ala or Leu;

Xaa27 is Ala or Lys;

Xaa28 is Ala or Asn; and $Z_1$ is —OH, —$NH_2$, Gly-$Z_2$, Gly Gly-$Z_2$, Gly Gly Xaa31-$Z_2$, Gly Gly Xaa31 Ser-$Z_2$, Gly Gly Xaa31 Ser Ser-$Z_2$, Gly Gly Xaa31 Ser Ser Gly-$Z_2$, Gly Gly Xaa31 Ser Ser Gly Ala-$Z_2$, Gly Gly Xaa31 Ser Ser Gly Ala Xaa36-$Z_2$, Gly Gly Xaa31 Ser Ser Gly Ala Xaa36 Xaa37-$Z_2$, Gly Gly Xaa31 Ser Ser Gly Ala Xaa36 Xaa37 Xaa38-$Z_2$, or Gly Gly Xaa31 Ser Ser Gly Ala Xaa36 Xaa37 Xaa38 Xaa39-$Z_2$, Xaa31, Xaa36, Xaa37, and Xaa38 are independently selected from the group consisting of Pro, homoproline, 3Hyp, 4Hyp, thioproline, N-alkylglycine, N-alkylpentylglycine, or N-alkylalanine, Xaa39 is Ser, or Tyr (e.g. Ser), and $Z_2$ is —OH, or —$NH_2$, provided that:

no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala; and when Xaa1 is His, Arg, or Tyr, at least one of Xaa3, Xaa4, and Xaa9 is Ala.

In some embodiments, the N-alkyl groups for N-alkylglycine, N-alkylpentylglycine, and N-alkylalanine may include lower alkyl groups, such as, of 1 to about 6 carbon atoms or 1 to 4 carbon atoms. The compound represented by Chemical Formula I may include compounds identified in Examples 1 to 89 (Compounds 1 to 89, respectively), and the corresponding compounds identified in Examples 104 and 105 in PCT Application Serial No. PCT/US98/24273, filed on Nov. 13, 1998, entitled "Novel Exendin Agonist Compounds", which is hereby incorporated by reference in its entireties for all purposes.

In a particular embodiment, exendin derivatives of Chemical Formula I may include those wherein Xaa1 of Chemical Formula I is His, Ala, Norval, or 4-imidazopropionyl. In another embodiment, Xaa1 of Chemical Formula I is His, Ala, or 4-imidazopropionyl. In an additional embodiment, the Xaa1 of Chemical Formula I is His or 4-imidazopropionyl.

Exendin derivatives of Chemical formula I may be those wherein Xaa2 is Gly.

Exendin derivatives of Chemical Formula I may be those wherein Xaa3 is Ala.

Exendin derivatives of Chemical Formula I may be those wherein Xaa4 is Ala.

Exendin derivatives of Chemical Formula I may be those wherein Xaa9 is Ala.

Exendin derivatives of Chemical Formula I may be those wherein Xaa14 is Leu, pentylglycine, or Met.

Exendin derivatives of Chemical Formula I may be those wherein Xaa21 is Lys-NHε-R, wherein R is Lys, Arg, or $C_1$-$C_{10}$ straight chain or branched alkanoyl.

In an embodiment, the exendin derivatives of Chemical Formula I may be those wherein Xaa25 is Trp or Phe.

In another embodiment, the exendin derivatives of Chemical Formula I may be those wherein Xaa6 is Ala, Phe, or naphthylalanine, Xaa22 is Phe or naphthylalanine, and Xaa23 is Ile or Val. Further, exendin derivatives of Chemical Formula I may be those wherein:

Xaa31, Xaa36, Xaa37, and Xaa38 are independently selected from the group consisting of Pro, homoproline, thioproline, and N-alkylalanine; $Z_1$ may be —$NH_2$; and $Z_2$ may be —$NH_2$.

In other embodiments, the exendin derivatives of Chemical Formula I may be those wherein Xaa1 is Ala, His, or Tyr (e.g., Ala or His); Xaa2 is Ala or Gly; Xaa6 is Phe or naphthylalanine; Xaa14 is Ala, Leu, pentylglycine, or Met; Xaa22 is Phe or naphthylalanine;

Xaa23 is Ile or Val; Xaa31, Xaa36, Xaa37, and Xaa38 are independently selected from the group consisting of Pro, homoproline, thioproline, and N-alkylalanine; Xaa39 is Ser or Tyr (e.g. Ser); and $Z_1$ may be —$NH_2$.

According to an embodiment, the exendin derivatives of Chemical Formula I may be those wherein Xaa1 is His or Ala; Xaa2 is Gly or Ala; Xaa3 is Ala, Asp, or Glu; Xaa4 is Ala or Gly; Xaa5 is Ala or Thr; Xaa6 is Phe or naphthylalanine; Xaa7 is Thr or Ser; Xaa8 is Ala, Ser, or Thr; Xaa9 is Ala, Asp, or Glu; Xaa10 is Ala, Leu, or pentylglycine; Xaa11 is Ala or Ser;

Xaa12 is Ala or Lys; Xaa13 is Ala or Gln; Xaa14 is Ala, Leu, Met, or pentylglycine; Xaa15 is Ala or Glu; Xaa16 is Ala or Glu; Xaa17 is Ala or Glu; Xaa19 is Ala or Val; Xaa20 is Ala or Arg; Xaa21 is Ala or Leu; Xaa22 is Phe or naphthylalanine; Xaa23 is Ile, Val, or tert-butylglycine; Xaa24 is Ala, Glu, or Asp; Xaa25 is Ala, Trp, or Phe; Xaa26 is Ala or Leu;

Xaa27 is Ala or Lys; Xaa28 is Ala or Asn; $Z_1$ is —OH, —$NH_2$, Gly-$Z_2$, Gly Gly-$Z_2$, Gly Gly Xaa31-$Z_2$, Gly Gly Xaa31 Ser-$Z_2$, Gly Gly Xaa31 Ser Ser-$Z_2$, Gly Gly Xaa31 Ser Ser Gly-$Z_2$, Gly Gly Xaa31 Ser Ser Gly Ala-$Z_2$, Gly Gly Xaa31 Ser Ser Gly Ala Xaa36-$Z_2$, Gly Gly Xaa31 Ser Ser Gly Ala Xaa36 Xaa37-$Z_2$, Gly Gly Xaa31 Ser Ser Gly Ala Xaa36 Xaa37 Xaa38-$Z_2$, or Gly Gly Xaa31 Ser Ser Gly Ala Xaa36 Xaa37 Xaa38 Xaa39-$Z_2$; Xaa31, Xaa36, Xaa37, and Xaa38 are independently Pro, homoproline, thioproline, or N-methylalanine; Xaa39 is Ser or Tyr (e.g. Ser); and $Z_2$ is —OH or —$NH_2$, provided that no more than three of Xaa3, Xaa5, Xaa6, Xaa8, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala, and when Xaa1 is His, Arg, or Tyr, at least one of Xaa3, Xaa4, and Xaa9 may be Ala.

In further embodiments, the compounds of Chemical Formula I may include those having the amino acid sequences of SEQ ID NOS: 5 to 93 set forth in PCT application Serial No. PCT/US98/25728, or those set forth in U.S. Provisional Application 60/066,029, which are hereby incorporated by reference.

According to an embodiment, provided are compounds where Xaa14 is Leu, He, Val, or pentylglycine (e.g. Leu or pentylglycine); and Xaa25 is Ala, Phe, Tyr, or naphthylalanine (e.g. Phe or naphthylalanine). These compounds will be less susceptible to oxidative degradation, both in vitro and in vivo, as well as during synthesis of the compound.

In another aspect, the exendin derivatives may include the compounds represented by Chemical Formula II, or their pharmaceutically acceptable salts:

Xaa1 Xaa2 Xaa3 Xaa4 Xaa5 Xaa6 Xaa7 Xaa8 Xaa9
Xaa10 Xaa11 Xaa12 Xaa13 Xaa14 Xaa15
Xaa16 Xaa17 Ala Xaa19 Xaa20 Xaa21 Xaa22
Xaa23 Xaa24 Xaa25 Xaa26 $X_1$-$Z_1$, 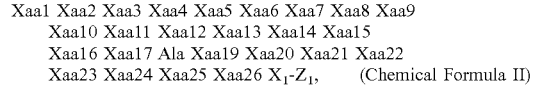

wherein:
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHε-R (wherein, R is Lys, Arg, C1-C10 straight chain or branched alkanoyl, or cycloalleylalkanoyl);
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;

X₁ is Lys Asn, Asn Lys, Lys-NHε-R Asn, Asn Lys-NHε-R, Lys-NHε-R Ala, Ala Lys-NHε-R, wherein R is Lys, Arg, a C1-C10 straight chain or branched alkanoyl, or cycloalkylalkanoyl;

Z₁ is —OH, —NH₂, Gly-Z₂, Gly Gly-Z₂, Gly Gly Xaa31-Z₂, Gly Gly Xaa31 Ser-Z₂, Gly Gly Xaa31 Ser Ser-Z₂, Gly Gly Xaa31 Ser Ser Gly-Z₂, Gly Gly Xaa31 Ser Ser Gly Ala-Z₂, Gly Gly Xaa31 Ser Ser Gly Ala Xaa36-Z₂, Gly Gly Xaa31 Ser Ser Gly Ala Xaa36 Xaa37-Z₂, Gly Gly Xaa31 Ser Ser Gly Ala Xaa36 Xaa37 Xaa38-Z₂, or Gly Gly Xaa31 Ser Ser Gly Ala Xaa36 Xaa37 Xaa38 Xaa39-Z₂;

Xaa31, Xaa36, Xaa37, and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr; and Z₂ is —OH or —NH₂), provided that:

no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala; and when Xaa1 is His, Arg, Tyr, or 4-imidazopropionyl, at least one of Xaa3, Xaa4, and Xaa9 is Ala.

In certain embodiments, exendin derivatives of Chemical Formula II may include those wherein Xaa1 is His, Ala, Norval, or 4-imidazopropionyl (e.g. Xaa1 includes His, 4-imidazopropionyl, or Ala, or Xaa1 includes His, or 4-imidazopropionyl).

Exendin derivatives of Chemical Formula II may be those wherein Xaa2 is Gly.

Exendin derivatives of Chemical Formula II may be those wherein Xaa4 is Ala.

Exendin derivatives of Chemical Formula II may be those wherein Xaa9 is Ala.

Exendin derivatives of Chemical Formula II may be those wherein Xaa14 is Leu, pentylglycine, or Met.

Exendin derivatives of Chemical Formula II may be those wherein Xaa25 is Trp or Phe.

Exendin derivatives of Chemical Formula II may be those wherein Xaa6 is Ala, Phe, or naphthylalanine, Xaa22 is Phe or naphthylalanine, and Xaa23 is Ile or Val.

Exendin derivatives of Chemical Formula II may be those wherein Z₁ is —NH₂.

Exendin derivatives of Chemical Formula II may be those wherein Xaa31, Xaa36, Xaa37, and Xaa38 are independently selected from the group consisting of Pro, homoproline, thioproline, and N-alkylalanine.

Exendin derivatives of Chemical Formula II may be those wherein Xaa39 is Ser or Tyr (e.g. Ser). Eexendin derivatives of Chemical Formula II may be those wherein Z2 is —NH₂.

Exendin derivatives of Chemical Formula II may be those wherein Z₁ is —NH₂.

Exendin derivatives of Chemical Formula II may be those wherein Xaa21 is Lys-NHε-R, wherein, R is Lys, Arg, or C1-C10 straight chain or branched alkanoyl.

Exendin derivatives of Chemical Formula II may be those wherein X1 is Lys Asn, Lys-NHε-R Asn, or Lys-NHε-R Ala, wherein R is Lys, Arg, or a C1-C10 straight chain or branched alkanoyl.

In further embodiments, exendin derivatives of Chemical Formula II may include compounds having the amino acid sequences identified as SEQ ID Nos: 95-110 set forth in WO99/025728. The exendin derivatives of Chemical Formula II may include compounds having the amino acid sequences identified as SEQ ID Nos: 5-93, as described in PCT application PCT/US98/24210, filed Nov. 13, 1998, entitled "Novel Exendin Agonist Compounds". In another aspect, the exendin derivatives of Chemical Formula II may include compounds having the amino acid sequences identified as SEQ ID Nos: 37-40 set forth in WO99/007404. The above documents are hereby incorporated by reference.

The abbreviations used in Chemical Formula I and II stand for the following.

"ACN" and "CH₃CN" refer to acetonitrile.

"Boc", "tBoc", and "Tboc" refer to t-butoxy carbonyl.

"DCC" refers to N,N'-dicyclohexylcarbodiimide.

"Fmoc" refers to fluorenylmethoxycarbonyl.

"HBTU" refers to 2-(1H-benzotriazol-1-yl)-1,1,3,3,-tetramethyluronium hexafluorophosphate.

"HOBt" refers to 1-hydroxybenzotriazole monohydrate.

"homoP" and "hPro" refer to homoproline.

"MeAla" and "Nme" refer to N-methylalanine.

"naph" refers to naphthylalanine.

"pG" and "pGly" refer to pentylglycine.

"tBuG" refers to tertiary-butylglycine.

"ThioP" and "tPro" refer to thioproline.

"3Hyp" refers to 3-hydroxyproline.

"4Hyp" refers to 4-hydroxyproline.

"NAG" refers to N-alkylglycine.

"NAPG" refers to N-alkylpentylglycine.

"Norval" refers to norvaline.

In an embodiment, the exendin fragments or derivatives may have a C-terminus substituted or non-substituted with an amide group, and may be selected from the group consisting of exendin-4(1-28) (SEQ ID NO: 15), exendin-4(1-28) amide, exendin-4(1-30) (SEQ ID NO: 7), exendin-4(1-30) amide, exendin-4(1-31) (SEQ ID NO: 54), exendin-4(1-31) amide, ¹⁴Leu25Phe exendin-4 (SEQ ID NO: 55), ¹⁴Leu²⁵Phe exendin-4 amide, and their pharmaceutically acceptable salts.

Controlled-Release Formulation

According to other embodiments, the controlled-release composition or microspheres may contain exendin, GLP-1 or a therapeutically effective GLP-1 or exendin analogue as an active ingredient in the amount of about 0.1 to about 10 parts by weight (e.g. about 0.8 to about 6 parts by weight) based on 100 parts by weight of the composition or microsphere comprising: exendin (such as exendin-4), GLP-1 or a therapeutically effective GLP-1 or exendin analogue (such as an exendin-4 analogue); biodegradable polymers; and coating materials. For example, the controlled-release composition or microspheres may include about 0.1 to about 10 parts, about 0.1 to about 9 parts, about 0.1 to about 8 parts, about 0.1 to about 7 parts, about 0.1 to about 6 parts, about 0.1 to about 6 parts, about 0.1 to about 5 parts, about 0.1 to about 4 parts, about 0.1 to about 3 parts, about 0.5 to about 10 parts, about 0.5 to about 9 parts, about 0.5 to about 8 parts, about 0.5 to about 7 parts, about 0.5 to about 6 parts, about 0.5 to about 6 parts, about 0.5 to about 5 parts, about 0.5 to about 4 parts, about 0.5 to about 3 parts, about 1 to about 10 parts, about 1 to about 9 parts, about 1 to about 8 parts, about 1 to about 7 parts, about 1 to about 6 parts, about 1 to about 6 parts, about 1 to about 5 parts, about 1 to about 4 parts, about 1 to about 3 parts, about 2 to about 10 parts, about 2 to about 9 parts, about 2 to about 8 parts, about 2 to about 7 parts, about 2 to about 6 parts, about 2 to about 6 parts, about 2 to about 5 parts, about 2 to about 4 parts, about 3 to about 10 parts, about 3 to about 9 parts, about 3 to about 8 parts, about 3 to about 7 parts, about 3 to about 6 parts, about 4 to about 10 parts, about 4 to about 9 parts, about 4 to about 8 parts, about 4 to about 7 parts, about 5 to about 10 parts, about 5 to about 9 parts, about 5 to about 8 parts, about 6 to about 10 parts, about 6 to about 9 parts, or about 7 to about 10 parts of exendin or a therapeutically effective analogue thereof and/or GLP-1 or a therapeutically effective analogue thereof by weight, based on 100 parts by weight of the composition or microsphere comprising: exendin, GLP-1, or a therapeutically effective GLP-1 or exendin analogue; biodegradable polymers; and coating materials. When the amount of exendin, GLP-1 or a therapeutically effective GLP-1 or exendin analogue contained in the composition or microspheres according to the present disclosure is lower than the above range, the efficient effect of exendin, GLP-1 or a therapeutically effective GLP-1 or exendin analogue cannot be obtained, and when the amount of exendin, GLP-1 or a therapeutically effective GLP-1 or exendin analogue is higher than the above range, the initial burst of exendin, GLP-1 or a therapeutically effective GLP-1 or exendin analogue is increased, thereby causing side effects due to an initial burst, and thus it is preferable that the amount of exendin, GLP-1 or a therapeutically effective GLP-1 or exendin analogue is within the above range.

The biodegradable polymer refers to all polymers that do not harm human beings, because when it is administered into the body, it can be slowly degraded and excreted. The biodegradable polymer may include one or more (e.g., one, two, three, four, five, six, or more) selected from the group consisting of polylactide (PLA), polyglycolide (PGA), poly (lactide-co-glycolide) (PLGA), polyorthoester, polyanhydride, polyhydroxybutyric acid, polycaprolactone, and polyalkylcarbonate, and copolymers of one or more polymers and polyethylenglycol (PEG), wherein the one or more polymers may be in the form of a copolymer or a simple mixture.

For example, the biodegradable polymer may be one or more selected from the group consisting of poly(lactide-co-glycolide)s (PLGA) consisting of RG502H (IV=0.16 to 0.24 dL/g), RG503H (IV=0.32 to 0.44 dL/g), and RG504H (IV=0.45 to 0.60 dL/g), having the lactide:glycolide ratio of 1:1, and RG752H (IV=0.14 to 0.22 dL/g) having the lactide:glycolide ratio of 75:25, polylactides (PLA), R202H (IV=0.16 to 0.24 dL/g) and R203H (IV=0.25 to 0.35 dL/g), which are provided by Evnik, Germany; poly(lactide-co-glycolide)s, 5050DL 2A (IV=0.15 to 0.25 dL/g), 5050DL 3A (IV=0.25 to 0.43 dL/g), and 5050DL 4A (IV=0.38 to 0.48 dL/g), which are copolymers provided by Evonik (Parsippany, N.J.), USA, having a lactide:glycolide ratio of 1:1; and the like, but equivalent polymers may be provided/acquired from any appropriate source.

In further embodiments, the biodegradable polymer may be a polymer-sugar complex, wherein a sugar is coupled with: (1) a polymer selected from the group consisting of polylactides (PLA), polyglycolides (PGA), poly(lactide-co-glycolide)s (PLGA), polyorthoesters, polyanhydrides, polyhydroxybutyric acids, polycaprolactones, and polyalkylcarbonates; (2) a copolymer of at least two of the polymer group; or (3) a copolymer of polyethylenglycol (PEG) and one of the polymer group.

In other embodiment of the present disclosure, the polymer-sugar complex may refer to a complex, wherein the polymer is substituted for a hydroxyl group of the sugar. The sugar may include monosaccharides and polysaccharides, which include 1 to 8 saccharide units, wherein each saccharide unit includes 3 to 6 hydroxyl groups, and straight chain sugar-alcohols including 3 to 6 hydroxyl groups and having a molecular weight of 20,000 or less. The sugar-alcohols may include mannitol, pentaerythritol, sorbitol, ribitol, and xylitol. The polymer couples with the sugar at three or more hydroxyl groups present in the sugar.

The polymer-sugar complex according to the above embodiment has in vivo properties similar to the polymer that is coupled with sugar, has various degradation rates depending on the kind of the polymer used, and is degraded to a harmless polymer and sugar in the body, and therefore it may be suitable for the biodegradable polymer. In an embodiment, the polymer-sugar complex may be a PLA-glucose complex, a PGA-glucose complex, or a PLGA-glucose complex, wherein the PLGA-glucose complex may be one having the following structure:

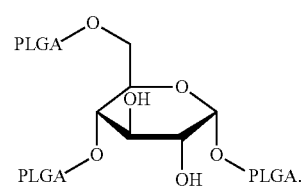

In the controlled-release microspheres according to the present disclosure, the coating layer formed on the surface thereof allows effective control of the initial burst of exendin or GLP-1 or therapeutically effective GLP-1 or exendin analogue, thereby preventing the side effects caused by the excessive initial burst. The biodegradable polymer may be used without any limitation of viscosity.

In the controlled-release composition/formulation according to the present disclosure, the biodegradable polymer plays a role as a matrix for preserving the active ingredient (exendin, GLP-1 or a therapeutically effective GLP-1 or exendin analogue), where an insufficiently low viscosity of the polymer fails to effectively preserve the active ingredient, thereby increasing the initial burst, and an excessively high viscosity of the polymer causes a decrease in the total released amount of the active ingredient, thereby decreasing the bioavailability thereof. In the present disclosure, not only the biodegradable polymer, but also, the coating materials contained in the composition plays a role of controlling drug release, and thus, the biodegradable polymer having a relatively low viscosity can be used. Therefore, in order to effectively control the initial burst of drug and improve the bioavailability, the intrinsic viscosity (IV) of the biodegradable polymer, which is measured for a biodegradable polymer dissolved in chloroform at a concentration of 1% (W/V) at 25° C.±0.1° C. using a Ubbelohde Viscometer, may be about 0.1 to about 0.6 dL/g (e.g. about 0.15 to about 0.31 dL/g or about 0.16 to about 0.24 dL/g).

In the composition, formulation or the microspheres of the present disclosure, the biodegradable polymer plays a role as a matrix for preserving the active ingredient during release and controlling the release rate, where its content in the composition or the microspheres may be about 85 to about 99.89 parts by weight (e.g. about 91 to about 99 parts by weight), based on 100 parts by weight of the composition/formulation or the microspheres containing the active ingredient (exendin, GLP-1 or a therapeutically effective GLP-1 or exendin analogue), biodegradable polymer(s), and coating material(s).

The coating material is used to prevent excessive initial burst and increasing the bioavailability of the active ingredient, and in the microspheres of the present disclosure, it may be in the form of a coating layer on the surface thereof. The coating material may be one or more (e.g. one, two, or three) selected from basic amino acids, polypeptides, and organic nitrogen compounds. The basic amino acid may include arginine, lysine, histidine, and their derivatives. The polypeptide may include 2 to 10 amino acids (e.g. 2 to 5 amino acids), including one or more (e.g., one, two or three) selected from arginine, lysine, and histidine. The polypeptide may include more basic amino acids than acidic amino acids, thereby exhibiting a basic property. For example, the polypeptide may be L-Ala-L-His-L-Lys, L-Arg-L-Phe, Gly-L-His, Gly-L-His-Gly, Gly-L-His-L-Lys, L-His-Gly, L-His-Leu, L-Lys-L-Tyr-L-Lys, L-His-L-Val, L-Lys-L-Lys, L-Lys-L-Lys-L-Lys, L-Lys-L-Thr-L-Thr-L-Lys-L-Ser, and the like. Further, the organic nitrogen compound may be creatine, creatinine, urea, and the like.

The content of the coating material contained in the composition of the present disclosure, or coated on the microspheres, may be about 0.01 to about 5 parts by weight (e.g. about 0.015 to about 3 parts, about 0.01 to about 4, about 0.01 to about 3, about 0.01 to about 2, about 0.01 to about 4, about 0.01 to about 2, about 0.015 to about 5, about 0.015 to about 4, about 0.015 to about 2, about 0.05 to about 5, about 0.05 to about 4, about 0.05 to about 3, about 0.05 to about 2, about 0.1 to about 5, about 0.1 to about 4, about 0.1 to about 3, about 0.1 to about 2, about 0.5 to about 5, about 0.05 to about 4, about 0.05 to about 3, about 0.05 to about 2, about 1 to about 5, about 1 to about 4, about 1 to about 3, about 1.5 to about 5, about 1.5 to about 4, about 1.5 to about 3, about 2 to about 5, about 2 to about 4, about 3 to about 5 about 3 to about 4, or about 4 to about 5) by weight, based on 100 parts by weight of the composition or the microspheres comprising exendin, GLP-1 or a therapeutically effective GLP-1 or exendin analogue, biodegradable polymer(s), and coating material(s). An effective control of drug release cannot be obtained if the content of the coating material is lower than the above scope, whereas the effect of controlling the initial burst is not additionally increased even if the content of the coating material is increased to higher than the above scope.

Each controlled-release microsphere according to the present disclosure may have a smooth surface coated with the coating material, and an average size of about 1 to about 50 μm (e.g., about 5 to about 30 μm, about 1 to about 40 μm, about 1 to about 30 μm, about 1 to about 20 μm, about 1 to about 10 μm, about 5 to about 50 μm, about 5 to about 40 μm, about 5 to about 30 μm, about 5 to about 20 μm, about 5 to about 10 μm, about 10 to about 50 μm, about 10 to about 40 μm, about 10 to about 30 μm, about 10 to about 20 μm, about 20 to about 50 μm, about 20 to about 40 μm, about 20 to about 30 μm, about 30 to about 50 μm, about 30 to about 40 μm, or about 40 to about 50 μm). The smooth surface of the microsphere allows achievement of effective initial burst control and excellent bioavailability.

Unlike the conventional form, the controlled-release microsphere or a microsphere prepared from the composition/formulation of the present disclosure is coated with the coating material, allowing prevention of an excessive/detrimental initial burst and an increase in bioavailability, which cannot be obtained in the conventional exendin, GLP-1 or a therapeutically effective GLP-1 or exendin analogue containing microsphere. In particular, an excessive/detrimental initial burst of exendin, GLP-1 or a therapeutically effective GLP-1 or exendin analogue causes various side effects, such as vomiting, nausea, headache, and the like, and thus it is very important to lower the initial burst amount to 5% or below. The controlled-release microsphere or a microsphere prepared from the composition (or formulation) of the present disclosure lowers the released amount for the initial 24 hours to 5% or below. In order to decrease the side effects due to administering exendin, GLP-1 or a therapeutically effective GLP-1 or exendin analogue containing controlled-release microsphere, the initial burst amount for the initial hour may be about 5% or below (e.g. about 4% or below, about 3% or below, about 2% or below, or about 1% or below. The microspheres of the present disclosure comprise a coating layer of the coating material on the surface thereof, allowing effective control of the initial burst to remove the side effects due to the excessive/detrimental initial burst, and obtain a lasting and sufficient release of drug to achieve excellent bioavailability.

In an embodiment of the present disclosure, the formulation or the microspheres may further comprise excipients, such as protective colloids and/or stabilizers.

The composition or the microspheres may further comprise one or more protective colloids selected from polyvinyl alcohols, albumins, polyvinylpyrrolidones, gelatins, and the like. Although the protective colloid has no special effect to prevent the excessive/detrimental initial burst of active ingredient contained in the microspheres, it plays a role to prevent aggregation between the microspheres and improve dispersibility. Considering such role, the content of the protective colloid may be about 0.02% (W/W) to about 1.0% (W/W) (e.g. about 0.02% to about 0.8%, about 0.02% to about 0.6%, about 0.02% to about 0.4%, about 0.05% to about 1.0%, about 0.04% to about 0.8%, about 0.05% to about 0.5%, about 0.05% to about 0.4%, about 0.05% to about 0.3%, about 0.05% to about 0.2%, about 0.1% to about 1.0%, about 0.1% to about 0.8%, about 0.1% to about 0.6%, about 0.1% to about 0.4%, about 0.1% to about 0.3%, about 0.1% to about 0.2%, about 0.2% to about 1.0%, about 0.2% to about 0.8%, about 0.2% to about 0.6%, about 0.2% to about 0.4%, about 0.4% to about 1.0%, about 0.4% to about 0.8%, about 0.4% to about 0.6%, about 0.6% to about 1.0%, about 0.6% to about 0.8%, or about 0.8% to about 1.0%), based on the weight of the composition, formulation or the microspheres containing the exendin, GLP-1 or a therapeutically effective GLP-1 or exendin analogue, biodegradable polymer(s), and coating material(s).

In addition, in order to improve the stability of the microspheres during freeze-drying, the composition/formulation or the microspheres of the present disclosure may further comprise excipients selected from mannitol, trehalose, sucrose, sodium carboxymethyl cellulose, and the like, in an amount of about 5% (W/W) to about 30% (W/W), e.g. about 10% (W/W) to about 20% (W/W), based on the weight of the composition or the microspheres comprising the exendin, GLP-1 or a therapeutically effective GLP-1 or exendin analogue, biodegradable polymer(s), and coating material(s).

Further, the composition, formulation or the microsphere of the present disclosure may further comprise any additives and excipients conventionally used in drug formulation, the kind and the content of which may be easily determined by one skilled in the relevant art.

The exendin, GLP-1 or a therapeutically effective GLP-1 or exendin analogue comprising controlled-release microspheres utilized in the methods of present disclosure may be prepared by various methods, for example by coating the surface of the microspheres through suspending the microspheres in the coating material solution during or after the preparation of the microspheres, to prepare the controlled-release microspheres. The method of preparing the microspheres may be performed by a double emulsion method (W/O/W method), single emulsion method (O/W method), a phase-separation method, a spray drying method, and the like.

Specifically, the method of preparing the exendin, GLP-1 or a therapeutically effective GLP-1 or exendin analogue containing controlled-release microspheres may include the steps of: mixing active agent(s) and biodegradable polymer(s) to prepare a W/O-type emulsion or a homogeneous mixture; and emulsifying by adding the emulsion or the homogeneous mixture into an aqueous solution of a coating material to form a coating layer.

More specifically, in the case of using a double emulsion method, the method may include the steps of emulsifying by mixing an active ingredient(s) aqueous solution and a biodegradable polymer dissolved in an organic solvent to form a primary emulsion (W/O-type); suspending the emulsion in an aqueous solution of a coating material to form a W/O/W-type emulsion; heating the W/O/W-type emulsion to remove the solvent and harden the obtained microspheres; collecting and washing the hardened microspheres; and freeze-drying the microspheres. The organic solvent may be any organic solvent that is capable of forming an emulsion by dissolving the biodegradable polymer and then being mixed with an aqueous solution, and, for example, it may be one or more selected from the group consisting of chloroform, ethylacetate, methylenechloride, and methylethylketone (e.g. methylenechloride). In this case, the coating material is contained in a secondary aqueous phase (outer aqueous phase of the W/O/W emulsion), to form a coating layer on the outside of the microspheres comprising at least one active ingredient (e.g., exendin, GLP-1 or a therapeutically effective GLP-1 or exendin-4 analogue, or a combination thereof) and the biodegradable polymer, when the organic solvent is removed.

Alternatively, if a single emulsion method is employed, the method may include the steps of dissolving the active ingredient(s) and a biodegradable polymer in an organic solvent to form a homogeneous mixture; adding an aqueous solution containing a coating material to the obtained mixture to form an emulsion; heating the emulsion to remove the solvent and harden the obtained microspheres; collecting and washing the hardened microspheres; and freeze-drying the microspheres. The organic solvent may be any organic solvent that is capable of completely mixing the active ingredient(s) and the biodegradable polymer(s) to form a homogeneous mixture, and of being mixed with an aqueous solution to form an emulsion. For example, the organic solvent may be a mixed solvent wherein one or more selected from the group consisting of alcohols having 1 to 5 carbon atoms, glacial acetic acid, formic acid, dimethyl sulfoxide, and n-methylpyrrolidone, and one or more selected from the group consisting of chloroform, ethyl acetate, methylethylketone, and methylene chloride are mixed, and for example, wherein methanol and methylene chloride are mixed. In this case, the surface the finally-obtained microspheres has a coating layer thereon, by emulsifying the homogeneous mixture of the biodegradable polymer and the active ingredient(s) and adding the coating material to an aqueous solution for removing the organic solvent.

The method of preparing controlled-release microspheres may include the steps of: mixing the active ingredient(s) and a biodegradable polymer to form an emulsion or a homogeneous mixture; solidifying the obtained emulsion or homogeneous mixture to prepare primary microspheres; and suspending the obtained primary microspheres in an aqueous solution of a coating material to form a coating layer on each microsphere.

The solidifying method has no limitation, and may be any solidifying method conventionally used in the relevant art, for example a phase-separation method or a spray drying method. More specifically, if a phase-separation method is employed in the solidifying step, the method may include the steps of: mixing an aqueous solution of the active ingredient(s) and a biodegradable polymer dissolved in an organic solvent to form an emulsion, or mixing the active ingredient(s) and a biodegradable polymer in a mixed solvent to form a homogeneous mixture solution; adding an oil, such as silicon oil, to the obtained emulsion or solution to prepare primary microspheres; adding a non-solvent for the biodegradable polymer, such as a mixed solvent of an alcohol having 1 to 5 carbon atoms and an alkane having 1 to 12 carbon atoms, such as a mixed solvent of ethanol and heptane, to remove the organic solvent from the microspheres and harden the microspheres; suspending the obtained microspheres in an aqueous solution of a coating material to form a coating layer on each microsphere; and collecting, washing, and freeze-drying the coating layer-formed microspheres.

The organic solvent may be one or more (e.g. one, two, three, or four) selected from the group consisting of chloroform, ethyl acetate, methylene chloride, and methylethylketone, (e.g. methylene chloride). The mixed solvent may be one wherein one or more (e.g., one, two, three, four, five, or more) selected from the group consisting of at least one alcohol having 1 to 5 carbon atoms, glacial acetic acid, formic acid, dimethyl sulfoxide, and n-methylpyrrolidone, and one or more (e.g. one, two, three, or four) selected from the group consisting of chloroform, ethyl acetate, methylethylketone, and methylene chloride, are mixed (e.g. a mixed solvent of methanol and methylene chloride).

Alternatively, if a spray drying method is employed, the method may include the steps of: mixing an aqueous solution of active ingredient(s) and a biodegradable polymer dissolved in an organic solvent to form an emulsion, or mixing the active ingredient(s) and a biodegradable polymer in a single solvent or a mixed solvent to form a homogeneous mixture solution; spray-drying the obtained emulsion or solution to prepare primary microspheres; suspending the obtained primary microspheres in an aqueous solution of a coating material to form a coating layer on each microsphere; and washing and freeze-drying the coating layer-formed microspheres.

The organic solvent may be one or more (e.g. one, two, three, or four) selected from the group consisting of chloroform, ethyl acetate, methylene chloride, and methylethylketone (e.g. methylene chloride). The single solvent may be one or more (e.g. one, two, three, four, or five) selected from the group consisting of glacial acetic acid and formic acid, and the mixed solvent may be one wherein one or more (e.g., one, two, three, four, or more) selected from the group consisting of at least one alcohol having 1 to 5 carbon atoms, glacial acetic acid, formic acid, dimethyl sulfoxide, and n-methylpyrrolidone, and one or more selected from the group consisting of chloroform, ethyl acetate, methylethylketone, and methylene chloride, are mixed (e.g. a mixed solvent of methanol and methylene chloride).

The method may further include a step of adding a protective colloid material through any conventional method, such as protective colloid material may be added during the step of coating the microspheres with the coating material.

The concentration of the coating material dissolved in aqueous phase or in aqueous solution may be from about 0.01 M to about 1 M (e.g. about 0.1 M to about 0.5 M, about 0.01 M to about 0.8 M, about, about 0.01 M to about 0.6 M, about 0.01 M to about 0.4 M, about 0.1 to about 1 M, about 0.1 M to about 0.8 M, about, about 0.1 M to about 0.6 M, about 0.1 M to about 0.4 M, about 0.2 to about 1 M, about 0.2 M to about 0.8 M, about, about 0.2 M to about 0.6 M, about 0.2 M to about 0.4 M, about 0.4 to about 1 M, about 0.4 M to about 0.8 M, about, about 0.4 M to about 0.6 M, about 0.6 to about 1 M, about 0.6 M to about 0.8 M about, or about 0.8 M to about 1 M). A lower concentration of the coating material than the above scope fails to completely coat the surface of the microspheres with the coating material, whereas a higher concentration of the coating material than the above scope results in a supersaturated coating material solution, which cannot result in an improved effect on controlling the initial burst, and thus the concentration of the coating material may be within the above scope.

Administration

The controlled-release composition of the present disclosure may be administered through an oral or parenteral pathway (e.g. a parenteral pathway), such as an intravenous pathway, a subcutaneous pathway, an intramuscular pathway, an intraperitoneal pathway, and the like. Therefore, in an embodiment of the present disclosure, the controlled-release composition or formulation may be applied as an injection solution in the form of a dispersed solution. The effective amount of the composition may be suitably adjusted according to the age of the subject, the kind and the seriousness of the disease, and the condition of the subject, and the dosage of the active ingredient in the composition may be from about 0.01 to about 100 μg/kg/day (e.g. about 0.1 to about 10 μg/kg/day), which may be administered at once or dividedly at several times. The exact amount required will vary from polypeptide to polypeptide and subject to subject, depending on the species, age, and general condition of the subject, the severity of disease that is being treated, the particular polypeptide used, its mode of administration, and the like. Thus, it is not possible to specify an exact "insulinotropic amount" or an amount useful in treating neuronal disease or injury. However, an appropriate amount may be determined by one of ordinary skill in the art using only routine experimentation.

One skilled in the art would recognize how to monitor the effectiveness of the treatment and how to adjust the treatment accordingly. For example, blood glucose levels could be monitored with normoglycemia being the optimal effect of treatment. If blood glucose levels are higher than preferred levels, then the amount of polypeptide administered should be increased, and, if blood glucose levels are lower than preferred levels, then the amount of polypeptide administered would be decreased.

The compounds may be administered orally, intravenously, intramuscularly, intraperitoneally, topically, transdermally, locally, systemically, intraventricularly, intracerebrally, subdurally, or intrathecally. One skilled in the art would know to modify the mode of administration, the pharmacologic carrier, or other parameters to optimize the insulinotropic effects. The amount of active compound administered will, of course, be dependent on the subject being treated, the subject's weight, the manner of administration and the judgment of the prescribing physician.

Depending on the intended mode of administration, the pharmaceutical compositions may be in the form of solid, semi-solid or liquid dosage forms, such as, for example, tablets, suppositories, pills, capsules, powders, liquids, suspensions, lotions, creams, gels, or the like, e.g. in unit dosage form suitable for single administration of a precise dosage. The compositions will include, as noted above, an effective amount of the selected drug in combination with a pharmaceutically acceptable carrier and, in addition, may include other medicinal agents, pharmaceutical agents, carriers, adjuvants, diluents, etc. See, e.g., Remington's Pharmaceutical Sciences, latest edition, by E.W. Martin Mack Pub. Co., Easton, Pa., which discloses typical carriers and conventional methods of preparing pharmaceutical compositions that may be used in conjunction with the preparation of formulations of the polypeptides and which is incorporated by reference herein. For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., an active compound as described herein and optional pharmaceutical adjuvants in an excipient, such as, for example, water, saline aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see Remington's Pharmaceutical Sciences, referenced above.

For oral administration, fine powders or granules may contain diluting, dispersing, and/or surface active agents, and may be presented in water or in a syrup, in capsules or sachets in the dry state, or in a nonaqueous solution or suspension wherein suspending agents may be included, in tablets wherein binders and lubricants may be included, or in a suspension in water or a syrup. Where desirable or necessary, flavoring, preserving, suspending, thickening, or emulsifying agents may be included. In certain embodiments, the oral administration form is tablets or granules, which may be coated. Parental administration, if used, is generally characterized by injection.

Injectables can be prepared in conventional forms, either as liquid solutions or suspensions, solid forms suitable for solution or suspension in liquid prior to injection, or as emulsions. A more recently revised approach for parental administration involves use of a slow release or sustained release system, such that a constant level of dosage is maintained. See, e.g., U.S. Pat. No. 3,710,795, which is incorporated by reference herein.

For topical administration, liquids, suspension, lotions, creams, gels or the like may be used as long as the active compound can be delivered to the surface of the skin.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the present disclosure and are not intended to limit the scope of what the inventors regard as their disclosure. Efforts have been made to ensure accuracy with respect to numbers (e.g., amounts, temperature, etc.), but some errors and deviations should be accounted for.

Statistics:

Values are expressed as means±S.E.M. The Kolmogorov-Smirnov test was used to determine normality of distributions. Student's t test, Mann-Whitney tests, Fisher Exact test or 1- and 2-way ANOVAs were used for statistical analysis as indicated in results. ANOVA on ranks was used when the normality assumption was violated. Post-hoc Newman- Keuls test or Dunn's test was used for all pairwise multiple comparisons. A statistically significant difference was defined as p<0.05.

Example 1. Pharmacokinetics of Exendin-4 and Sustained Release in Plasma

PT302, a sustained release formulation of Exendin-4, contains a mixture of polymers (98%) and Exendin-4 (2%). Plasma levels of Exenatide were analyzed after injection with the Sustained Release formulation of exendin-4 (PT302). In particular, the pharmacokinetics of a single dose of PT302 was examined using 6 adult (9 weeks old) male Sprague-Dawley rats. PT302 was freshly dissolved in diluent and 2 mg/kg was administered subcutaneously. Blood was collect at 0 hours, 0.5 hours, and 1 hour after injection, as well as days 1, 3, 5, 7, 9, 11, 14, 18, 21, and 26 post injection. Plasma levels of Exendin-4 were quantified by the Peptron Exenatide EIA Kit (Peptron, Daejeon, South Korea). The data is shown in FIG. 1A with a Cmax of 1.85 ng/ml, a Tmax of 12.5 days, and a AUC of 18.55 ng*d/ml (values calculated from individual data of all 6 animals). As seen in FIG. 1A, the sustained-release formulation PT302 provides prolonged Exendin-4 plasma levels from a single subcutaneous injection acceptable for one to two weeks dosing regimen.

Figure 1B:
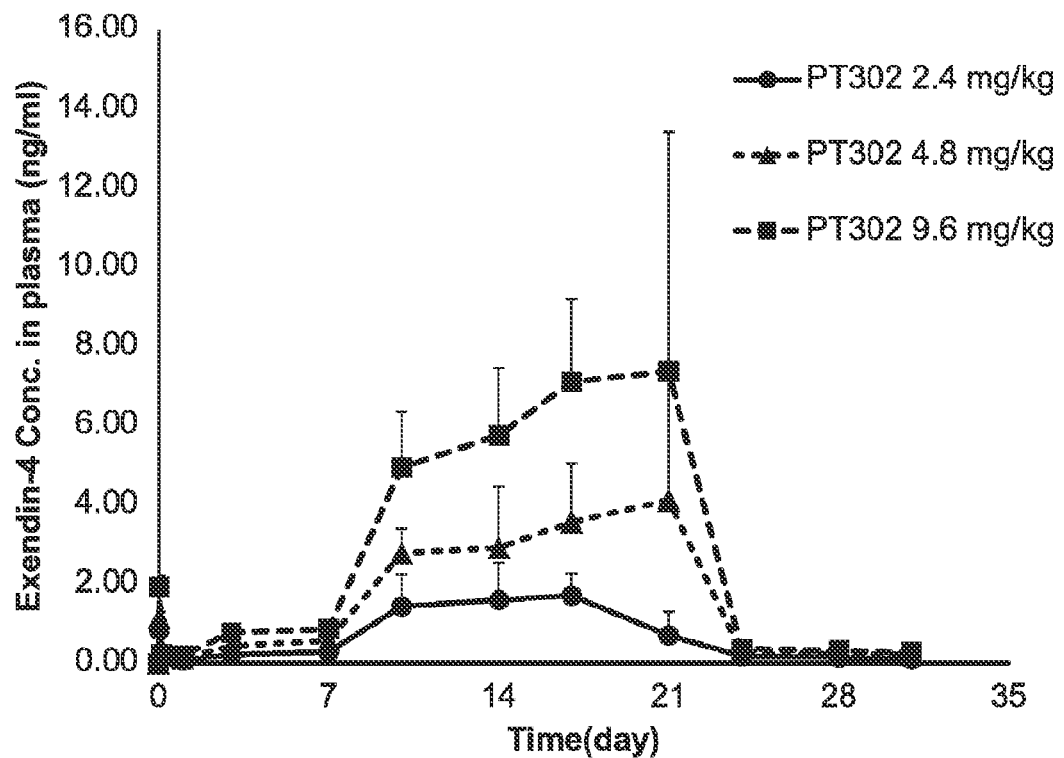
FIG. 1B. A graph illustrating time-dependent exenatide (exendin-4) plasma levels from a single subcutaneous administration of 2.4 mg/kg, 4.8 mg/kg, or 9.6 mg/kg sustained-release-Exenatide (PT302) to adult (9 weeks old) male Sprague-Dawley rats.

The pharmacokinetics of a single dose of PT302 at various dosages (2.4 mg/kg, 4.8 mg/kg, and 9.6 mg/kg) was examined using 6 adult (9 week old) male Sprague-Dawley rats per group. PT302 was freshly dissolved in diluent and administered as indicated subcutaneously. Blood was collected at 0 hours, 0.5 hours, and 1 hour after injection, as well as days 1, 3, 7, 10, 14, 17, 21, 24, 28, and 31 post injection. Plasma levels of Exendin-4 were quantified as discussed above. The data is shown in FIG. 1B with a Cmax of 2.23 ng/ml, a Tmax of 14.83 days, and AUC of 21.13 ng*d/ml for the 2.4 mg/kg dose; a Cmax of 5.21 ng/ml, a Tmax of 16.17 days, and AUC of 49.46 ng*d/ml for the 4.8 mg/kg dose; and a Cmax of 9.42 ng/ml, a Tmax of 17.17 days, and AUC of 87.14 ng*d/ml for the 9.6 mg/kg dose. FIG. 1B demonstrates that the sustained-release formulation PT302 provides prolonged Exendin-4 plasma levels from a single subcutaneous injection directly related to the dose level of PT302 administered.

Figure 2:
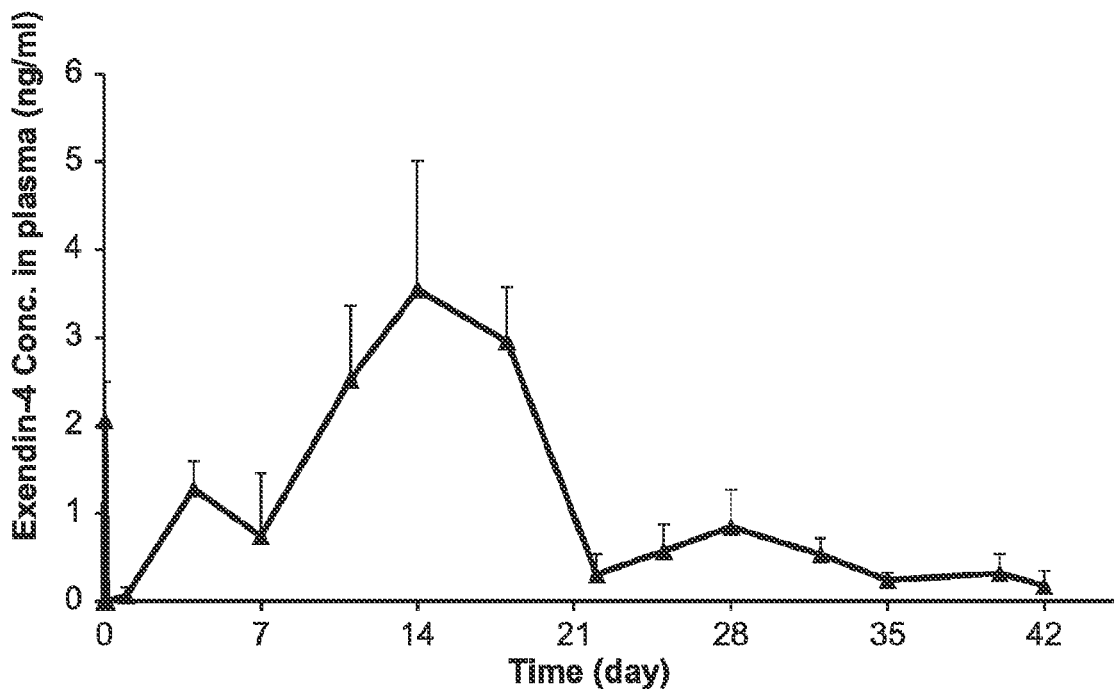
FIG. 2. A graph illustrating time dependent exendin-4 plasma levels from a single subcutaneous injection of sustained-release-Exenatide (PT304) at the amount of 4.0 mg/kg to adult (9 weeks old) male Sprague-Dawley rats.
Figure 3:
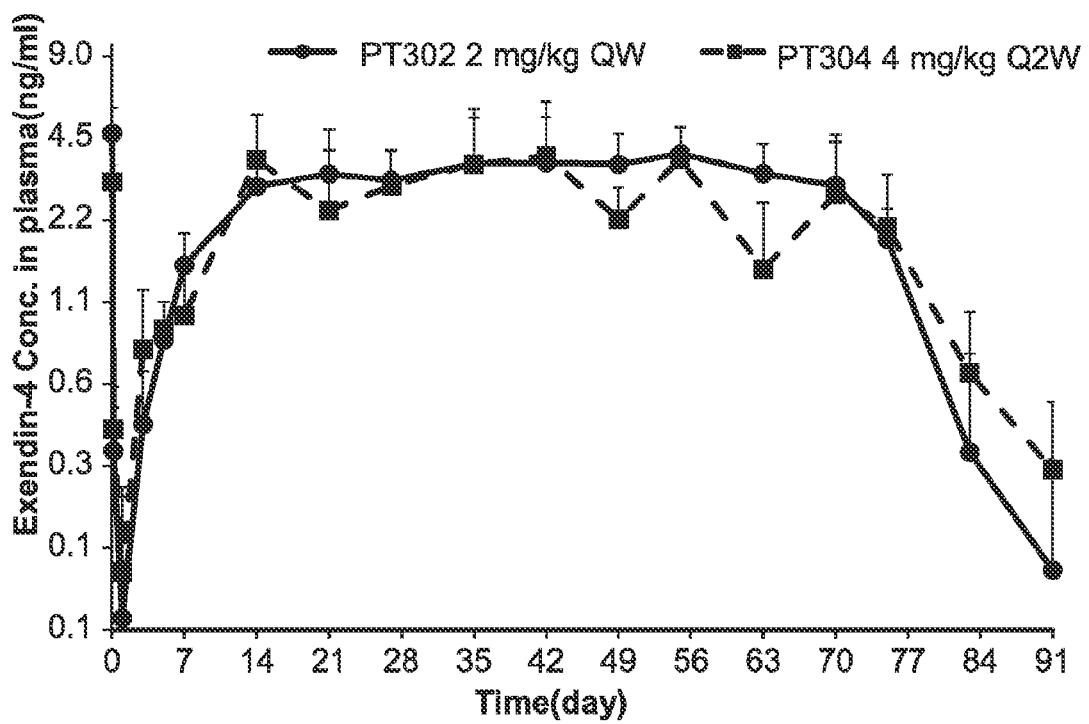
FIG. 3. A graph illustrating time-dependent exendin-4 plasma levels over a 10 week period in male Sprague-Dawley rats administered either PT302 or PT304 at the amounts and times indicated.

PT304, a sustained release formulation of Exendin-4, contains a mixture of polymers (96%) and Exendin-4 (4%). Plasma levels of Exenatide were analyzed after injection of 6 adult (9 weeks old) male Sprague-Dawley rats with the Sustained Release formulation of exendin-4 (PT304). PT304 was freshly dissolved in diluent and 4 mg/kg was administered subcutaneously. Blood was collect at 1 hour, and 3 hour after injection, as well as days 1, 4, 7, 11, 14, 18, 21, 25, 28, 32, 35, 39, and 42 post injection. Plasma levels of Exendin-4 were quantified by the Peptron Exenatide EIA Kit. The data is shown in FIG. 2 with a Cmax of 3.82 ng/ml, a Tmax of 14.17 days, and a AUC of 48.34 ng*d/ml (values calculated from individual data of all 6 animals). As seen in FIG. 2, the sustained-release formulation PT304 provides prolonged Exendin-4 plasma levels from a single subcutaneous injection acceptable for two to four weeks dosing regimen.

The pharmacokinetics of PT302 for a 10 week period was examined in 10 adult (9 weeks old) Sprague-Dawley rats per group. The rats were subcutaneously injected with a dose of 2 mg/kg of PT302 weekly or 4 mg/kg of PT304 every other week. The PT302 and PT304 were prepared as discussed above, and blood collected at 1 hour and 3 hours after the first injection, as well as on days 1, 3, 5, 7, 10, 14, 21, 28, 35, 42, 49, 56, 63, 70, 77, 84, and 91 days after the first injection. Serum levels of Exendin-4 were quantified as discussed above, and is shown in FIG. 3. The weekly injected rats had a Cmax of 5.27 ng/ml, a Tmax of 51.60 days, and a AUC of 236.42 ng*d/mL, while the fortnightly injected rats had a Cmax of 5.08 ng/ml, a Tmax of 47.89 days, and a AUC of 211.51 ng*d/mL.

Example 2. Pre-Treatment with PT302 Reduces Meth-Mediated Rotation in the 6-OHDA Rat Model of Parkinson's Disease The animals were treated with vehicle (9 rats), 0.4 mg/kg PT302 (low dose; 9 rats), or 2 mg/kg PT302 (high dose; 10 rats) on the days defined in FIG. 4A (i.e., on days 16 and 2 prior to a 6-OHDA unilateral lesion of the medial forebrain bundle, and on days 12, 26 and 40 after lesioning). As shown in FIGS. 4A and 4B, rats were subjected to meth-mediated rotation on days 20, 30 and 45 post-lesioning, and were euthanized on day 47. For lesioning, rats were anesthetized by chloral hydrate (400 mg/kg, i.p.) and placed in a stereotaxic frame. 6-OHDA (2.76 µg/µl×5 µl in 0.9% NaCl containing 0.2 mg/ml ascorbic acid) was unilaterally injected into the medial forebrain bundle (−4.4 mm AP, 1.2 mm ML relative to bregma and 8.4 mm below skull) over 4 minutes through a Hamilton microsyringe held by a stereotaxic arm. The microsyringe was lowered to the desired target locus in the brain using micromanipulators attached to the stereotaxic frame. The speed of injection (0.5 µl/minute) was controlled by a syringe pump (Micro 4, WPI, Sarasota, Fla.). The needle was removed 5 minutes after the injection. A piece of bone wax was placed on the burr hole to prevent the leakage of fluid. The wound was sutured or clipped. Body temperature was monitored with a thermistor probe and maintained at 37° C. with a heating pad during anesthesia. After recovery from the anesthesia, body temperature was further maintained at 37° C. for 3 hours using a temperature controlled incubator.

Meth-induced Rotational behavior [Liu D M, Lin S Z, Wang S D, Wu M I, Wang Y. Xenografting human T2 sympathetic ganglion from hyperhidrotic patients partially restores catecholaminergic functions in hemi-Parkinsonian athymic rats. Cell Transplant 1999; 8:563-91; and Luo Y, Hoffer B J, Wang Y. Rotation, Drug-induced. In: Kompoliti K, Verhagen Metman L, editors. Encyclopedia of Movement Disorders. Oxford: Academic Press, 2010. p 49-51] was evaluated using an 8-channel rotometer system (RotoMax, AccuScan Instruments, Inc). Animals were challenged with methamphetamine (2.5 mg/kg) 6 days after 6-OHDA lesioning as previously described [Yin L H, Shen H, Diaz-Ruiz O, Backman C M, Bae E, Yu S J, Wang Y. Early post-treatment with 9-cis retinoic acid reduces neurodegeneration of dopaminergic neurons in a rat model of Parkinson's disease. BMC Neurosci 2012; 13:120]. Methamphetamine is an indirect agonist that induces release of dopamine in the brain. Rats that receive unilateral injections of 6-OHDA in the nigrostriatal dopaminergic system are used as a model for PD. These animals exhibit ipsilateral rotations after administration of indirect dopamine agonists (such as methamphetamine) and contralateral rotations after direct dopamine agonists (such as apomorphine). These behaviors are related to unilateral changes in the expression of striatal dopaminergic markers.

As shown in FIG. 4B, treatment with PT302 significantly reduced rotation in both high and low dose of PT302 treatment group (p=0.018, F2, 87=4.309, two way ANOVA in low dose group) relative to vehicle. A post-hoc Newman-Keuls test indicated that the high dose of PT302 significantly attenuated meth-mediated rotation (p=0.037). Thus, sustained, steady-state administration of Exendin-4 in the form of PT302 significantly mitigated behavioral effects induced by a unilateral 6-OHDA lesion of the medial forebrain bundle in rats (a well characterized animal model of PD), providing neuroprotective activity.

Figure 4C:
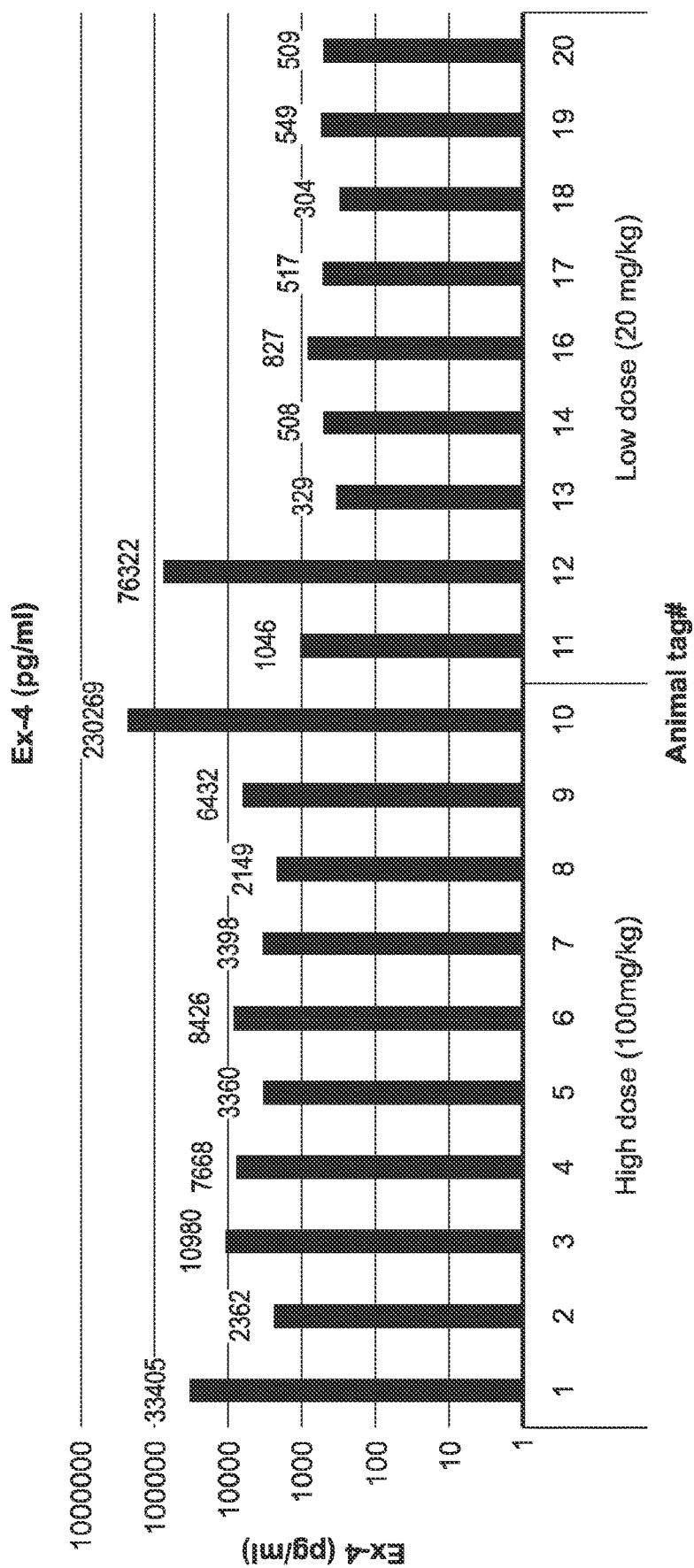
FIG. 4C. A graph illustrating plasma levels of Exendin-4 in 6-OHDA rats that have been pre-treated with PT302.

Plasma levels of Exendin-4 were quantified as discussed above. As shown in FIG. 4C, the average Exendin-4 plasma level was 30.845 pg/ml (n=10) in high dose rats and 8,990 pg/ml (n=9) in low dose rats. However, when the outlier rats/measurements (rat 1, 10 and 12) are removed, the average Exendin-4 plasma level was 5,596 pg/ml (n=8) in the high dose rats and 574 pg/ml (n=8) in the low dose rats.

Example 3. Post-Treatment with PT302 Reduced Meth-Induced Rotational Behavior in 6-OHDA Lesioned Rats The use of the unilateral 6-OHDA lesion of the medial forebrain bundle rodent model of PD, described in Example 2, can be combined with the post-treatment of a potential drug, as shown in the scheme in FIG. 5A. In this scenario, rodents are challenged with a unilateral 6-OHDA lesion (0 day), and treatment is initiated 6 days thereafter. This is a more difficult rodent model of PD to treat, as dopaminergic cell death has already been initiated and is ongoing prior to treatment. Nineteen rats were lesioned as described above. The meth-induced rotation was examined as discussed above with animals that rotated in excess of 300 turns/hour being separated into 2 groups to equalize group rotational behavior for vehicle or PT302 groups before the initiation of treatment. As outlined in FIG. 5A, meth-induced rotation was examined on 6, 20, 30 and 45 days after lesioning and the animals (adult male Sprague-Dawley rats-2 months old upon arrival) were treated with vehicle (s.c., n=1) or PT302 (100 mg/kg containing 2.0 mg/kg Exendin-4, s.c., n=8) on days 6, 20, and 34 after 6-OHDA lesioning. The PT302 was prepared as described above. The animals were euthanized on day 47 after lesioning. Blood and brain samples were collected, and plasma was separated and stored (−80° C.). Exendin-4 was measured in the plasma collected.

Figures 5A, 5B:
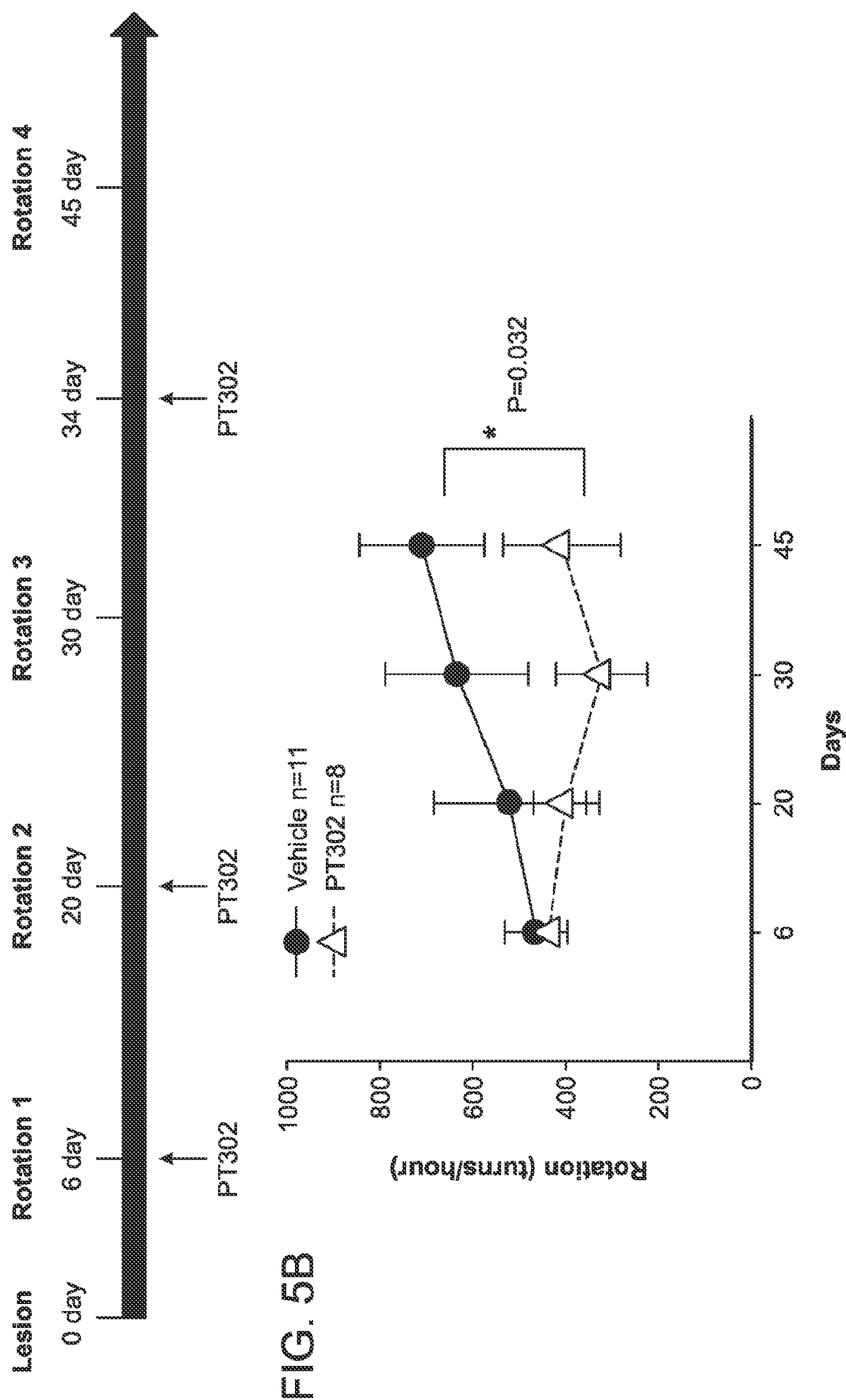
FIG. 5A. Outline of the study design of Example 3 in which Sprague-Dawley rats were administered PT302 after a 6-OHDA unilateral lesion of the medial forebrain bundle.
FIG. 5B. A graph illustrating the meth-induced rotational behavior of 6-OHDA rats that receive post-treatment with PT302.

As shown in FIG. 5B, PT302 significantly reduced meth-induced rotational behavior in the unilaterally 6-OHDA-lesioned rats (p=0.032, two way ANOVA), as compared to the vehicle control.

TH was examined by immunohistochemistry. Specifically, serial cryostat sections of the entire brain were cut at 25 μm thickness. One series from every sixth section was stained for TH. To control for staining variability, specimens from all experimental groups were included in every batch and reacted together in a net well tray under the same conditions. Sections were rinsed in 0.1M phosphate buffer (PB), blocked with 4% bovine serum albumin (BSA) and 0.3% Triton x-100 in 0.1M PB. Sections were then incubated in primary antibody (mouse monoclonal anti-TH diluted in 4% BSA and 0.3% Triton x-100 in 0.1M PB, concentration 1:100; Chemicon, Temecula, Calif.) for 17-19 hours at 4° C. Sections were then rinsed in 0.1M PB and incubated in secondary antibodies for 1 hour, followed by incubation for 1 hour with avidin-biotin-horseradish peroxidase complex. Sections were mounted on slides, and coverslipped. Control sections were incubated without primary antibody.

TH immunoreactivity in the striatum was measured by the ImageJ and was averaged from 3 brain sections chosen so that the anterior commissure was visible. TH immunoreactivity in the substantia nigra was measured every 360 μm throughout the midbrain (from bregma −4.2 mm to −6.0 mm). A total of 5 brain sections from each animal was used. The volume of the substantia nigra was analyzed using Cavalieri's method.

PT302 Reduced 6-OHDA-Mediated Dopaminergic Neurodegeneration in the Striatum.

Figure 5C:
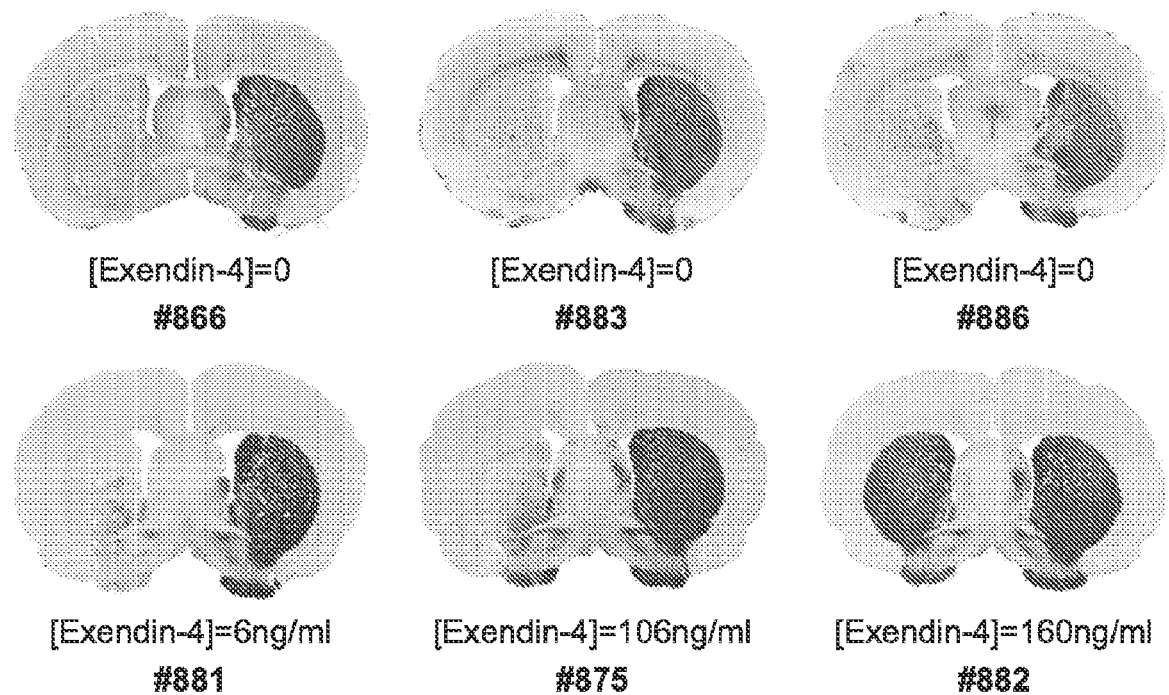
FIG. 5C. Representative microscopic images of Tyrosine hydroxylase (TH) immunohistochemistry of the striatum performed on rats with a 6-OHDA unilateral lesion of the medial forebrain bundle receiving vehicle (control; rats #866, #883, and #886) and PT302 (rats #881, #875, #882). Exendin-4 plasma concentrations (ng/ml) are noted for each animal.
Figure 5D:
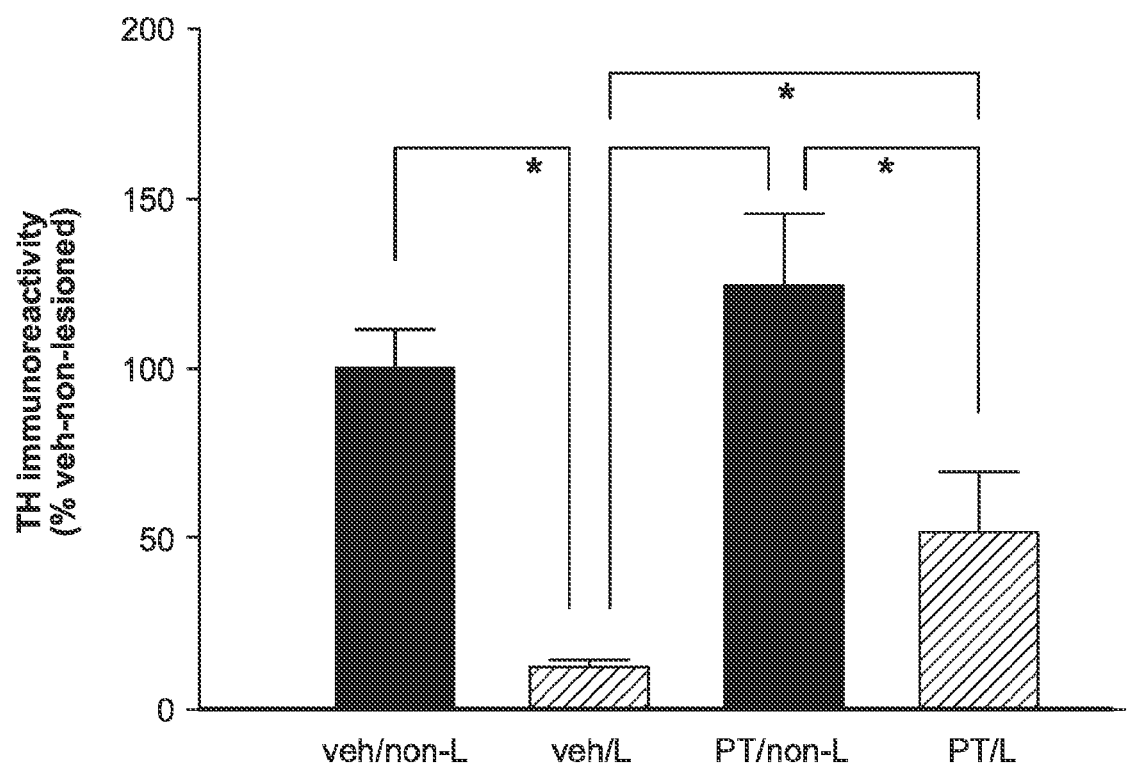
FIG. 5D. A graph illustrating the quantified TH immunoreactivity observed in the immunohistochemistry described in and associated with FIG. 5C.

Representative striatal TH immunostaining and plasma Exendin-4 levels from 3 rats (#866, 883, 886) receiving vehicle and 3 rats (#881, 875, 882) receiving PT302 are shown in FIG. 5C (plasma concentrations of exendin-4 in these same animals was quantified and are also noted in FIG. 5C). As shown in FIG. 5D, the injection of 6-OHDA significantly reduced striatal TH immunoreactivity in animals receiving vehicle, while PT302 significantly increased TH immunoreactivity in the lesioned striatum (*p<0.001, 2-Way ANOVA). L=lesioned side; non-L-non-lesioned side; veh=animals receiving vehicle; PT=PT302.

Figure 5E:
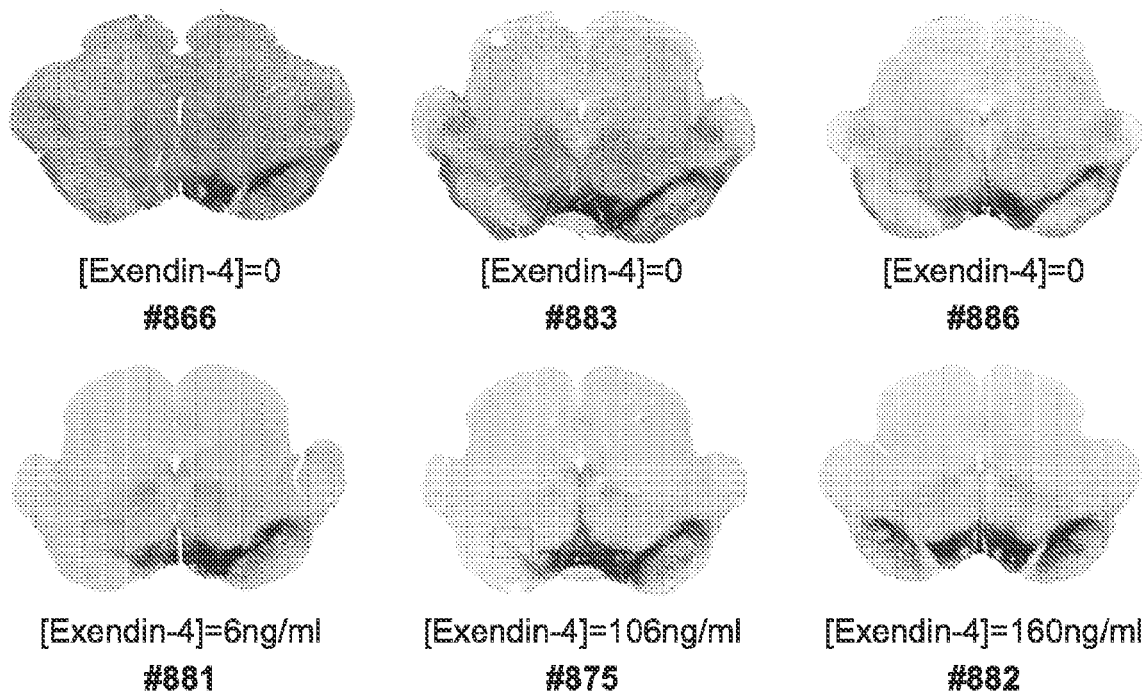
FIG. 5E. Representative microscopic images of TH immunohistochemistry of the substantia nigra performed on rats with a 6-OHDA unilateral lesion of the medial forebrain bundle receiving vehicle (control; rats #866, #883, and #886) and PT302 (rats #881, #875, and #882). Exendin-4 plasma concentrations (ng/ml) are noted for each animal.
Figure 5F:
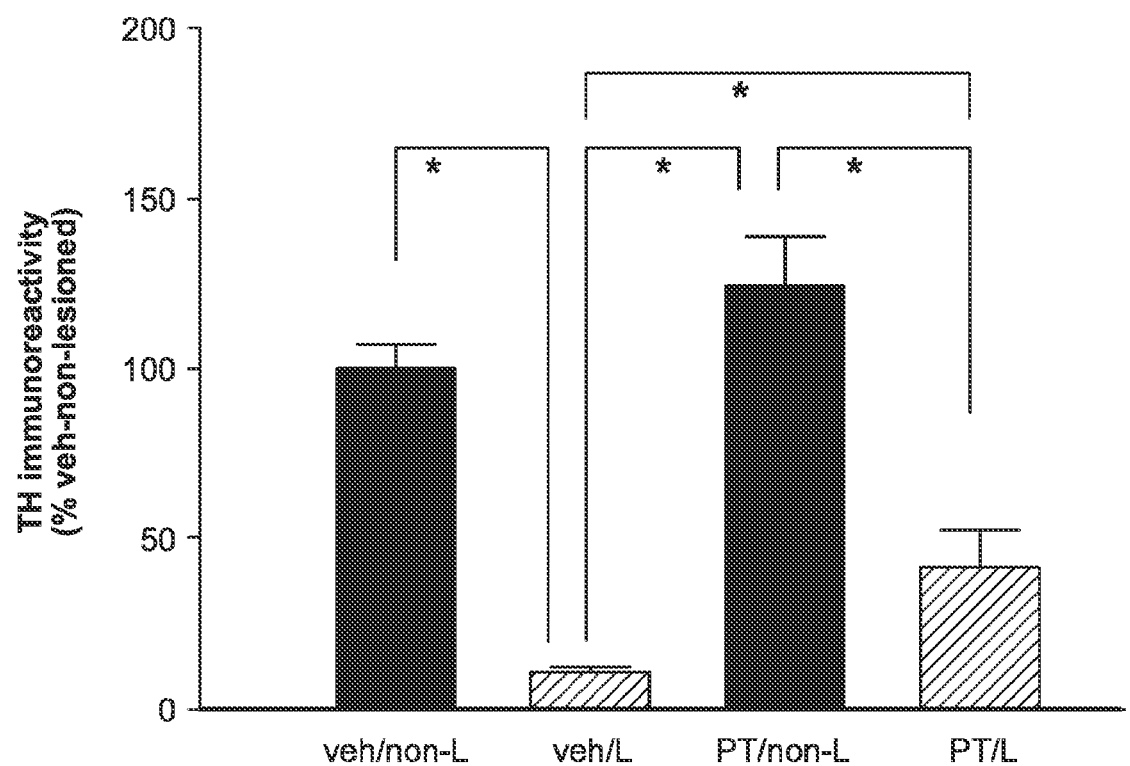
FIG. 5F. A graph illustrating the quantified TH immunoreactivity observed in the immunohistochemistry described in and associated with FIG. 5E.

TH immunoreactivity in the substantia nigra was measured by the ImageJ and was averaged from 3 brain sections chosen so that the anterior commissure was visible. Representative TH immunostaining from animals receiving vehicle (Rat #866, #883, #886) or PT302 (Rat #88 1, #875, #882) are shown in FIG. 5E (also shown are plasma levels of exendin-4 in the same animals). The TH immunoreactivity in substantia nigra was quantified every 360 um from bregma −4.2 mm to −6 mm, and is shown in FIG. 5F. The injection of 6-OHDA significantly reduced substantia nigra TH immunoreactivity in animals receiving vehicle, while PT302 significantly mitigated the loss of TH immunoreactivity in the lesioned substantia nigra (*p<0.001, 2-Way ANOVA). L=lesioned side; non-L-non-lesioned side; veh=animals receiving vehicle; PT=PT302

PT302 Post-Treatment Protects TH+ Neurons in the Lesioned Substantia Nigra.

Figure 5H:
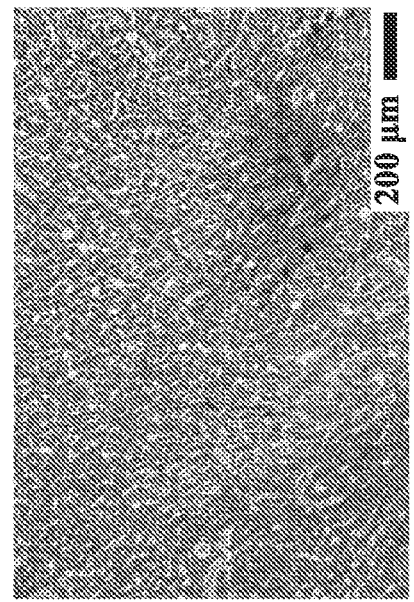
FIGS. 5G and 5H. Representative microscopic images of TH+ neurons observed on the non-lesioned side of the brain from a rat.
Figure 5G:
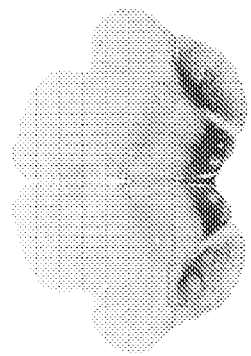
Figure 5I:
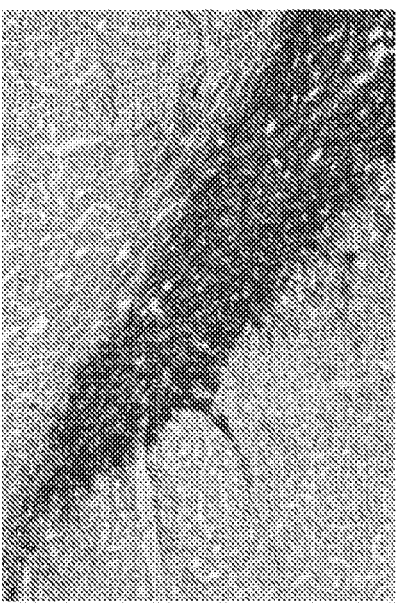
FIG. 5I. Representative microscopic image of no TH+ neurons present in substantia nigra on the lesioned side of the brain from a rat with a 6-OHDA unilateral lesion of the medial forebrain bundle.
Figure 5J:
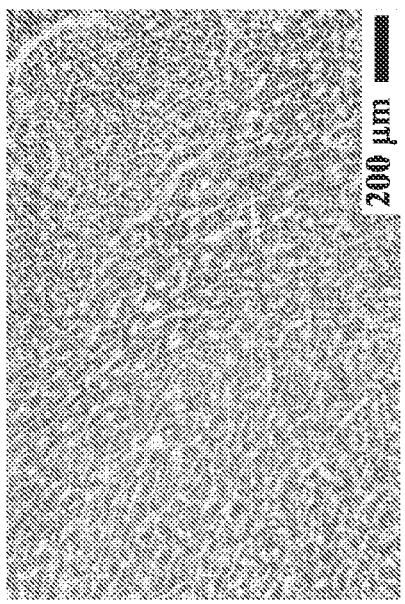
FIGS. 5J, 5K, and 5L. Representative images of brains of PT302 treated 6-OHDA rats.
Figure 5K:
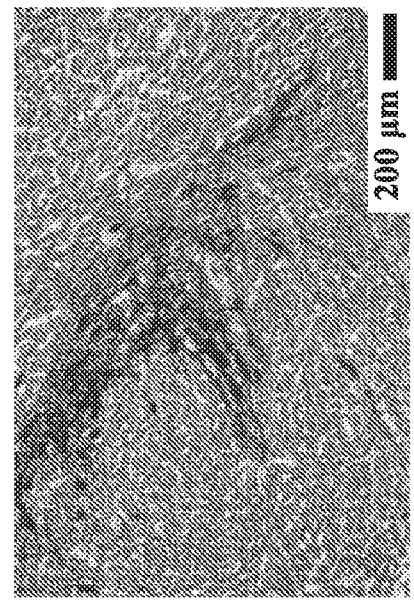
Figure 5L:
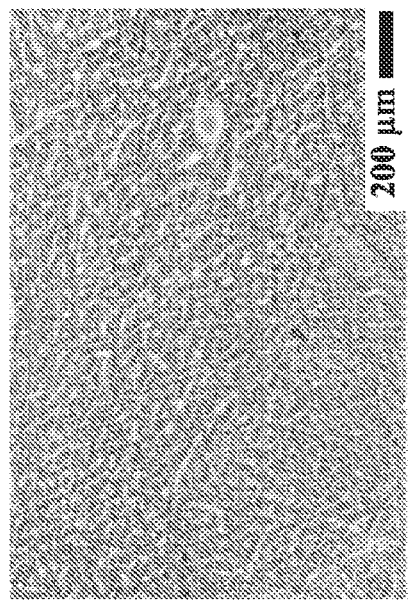

The brains were sectioned and immunohistochemistry performed as described above. TH+ neurons were found on the non-lesioned side of the brain (FIGS. 5G and 5H). Almost no TH+ neurons or fibers were found in the substantia nigra on the lesioned side of the brain (rat #886; FIG. 5I). Treatment with PT302 partially protected TH+ neurons (FIGS. 5J, 5K, and 5L).

Exendin-4 Mediated Protection in TH Neurons is Associated with the Plasma Exendin 4 Level.

Figure 5M:
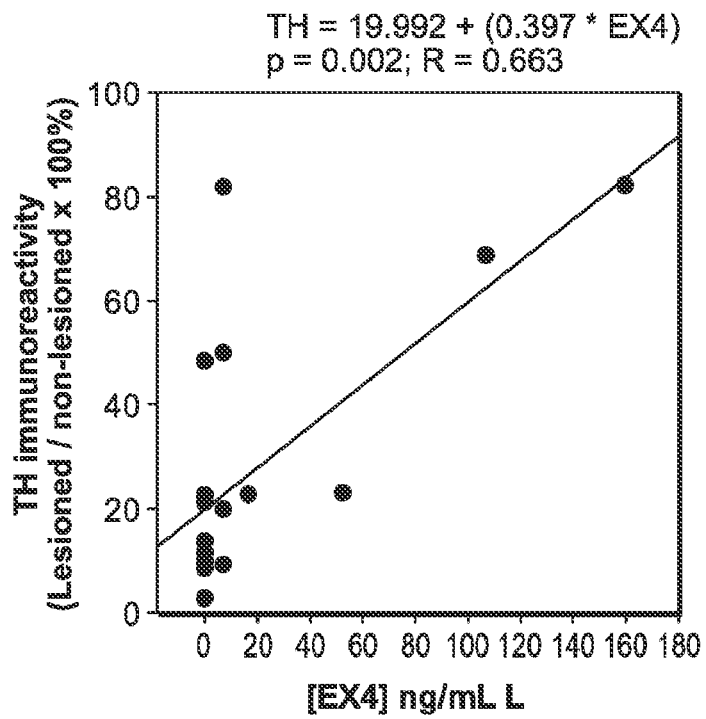
FIG. 5M. A graph illustrating the significant correlation observed between normalized TH immunoreactivity and Exendin-4 plasma levels in the striatia.
Figure 5N:
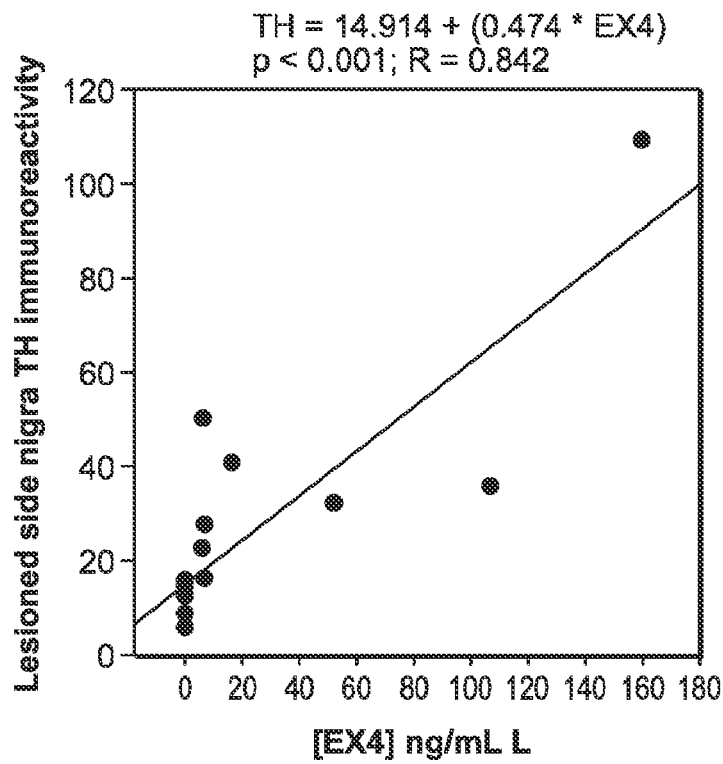
FIG. 5N. A graph illustrating the significant correlation observed between Exendin-4 plasma levels and TH immunoreactivity in the substantia nigra.

FIG. 5M shows the significant correlation found between normalized striatal TH (i.e. lesioned/non-lesioned side) immunoreactivity and plasma Exendin 4 levels within the same animals (p=0.002, R=0.663). FIG. 5L shows the significant correlation observed between plasma Exendin 4 levels and TH immunoreactivity in the substantia nigra on the lesioned side (p<0.001, R=0.842).

Figure 6A:
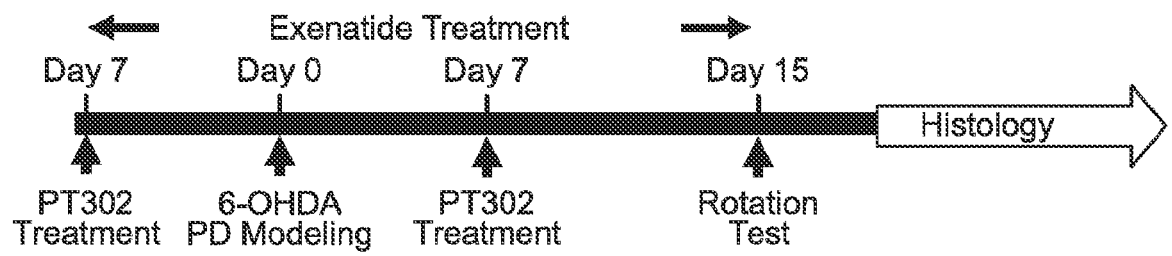
FIG. 6A. Outlines the study design of Example 4.
Figure 6B:
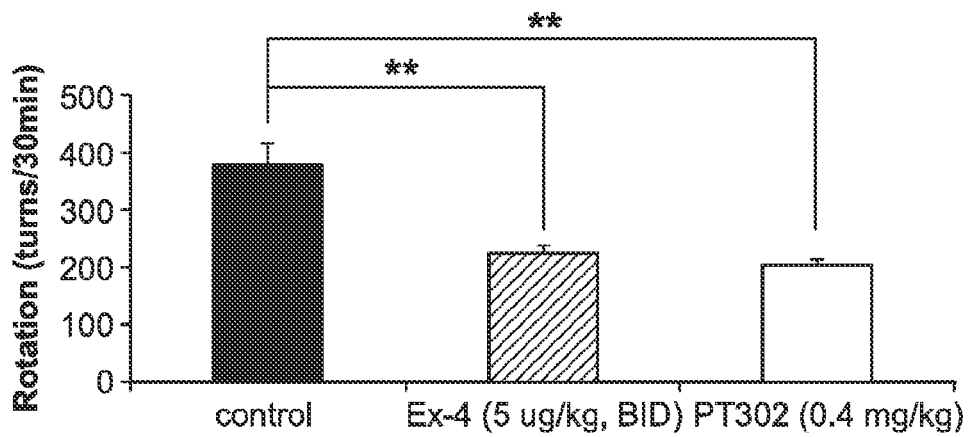
FIG. 6B. Exendin-4 and PT302 treatment reduces rotation in rats with a 6-OHDA unilateral lesion of the medial forebrain bundle.

Example 4. Pre-Treatment with PT302 Reduces Meth-Mediated Rotation in a 6-OHDA Rat Model of PD As shown in FIG. 6A, the animals were treated subcutaneously with Ex-4 (5 μg/kg, BID) or PT302 (0.4 mg/kg) 7 days before and 7 days after 6-OHDA lesioning, as described above. The 5 μg/kg BID dose of Exendin-4 used in this study is higher than can be achieved in humans (see Table 1 below), and a lower dose of approximately 1 μg/kg BID is equivalent to both the human dose and the PT302 dose used within the study. Both Ex-4 (5 μg/kg BID) and PT302 (0.4 mg/kg) treatment significantly reduced rotation (p=0.005 in Ex-4 and 0.002 in PT302 group) in the 6-OHDA lesioned rats (Figure. 6B).

Pre-Treatment with Either Exendin-4 or PT302 Protected Against 6-OHDA-Mediated Dopaminergic Neurodegeneration in the Substantia Nigra.

Figure 6C:
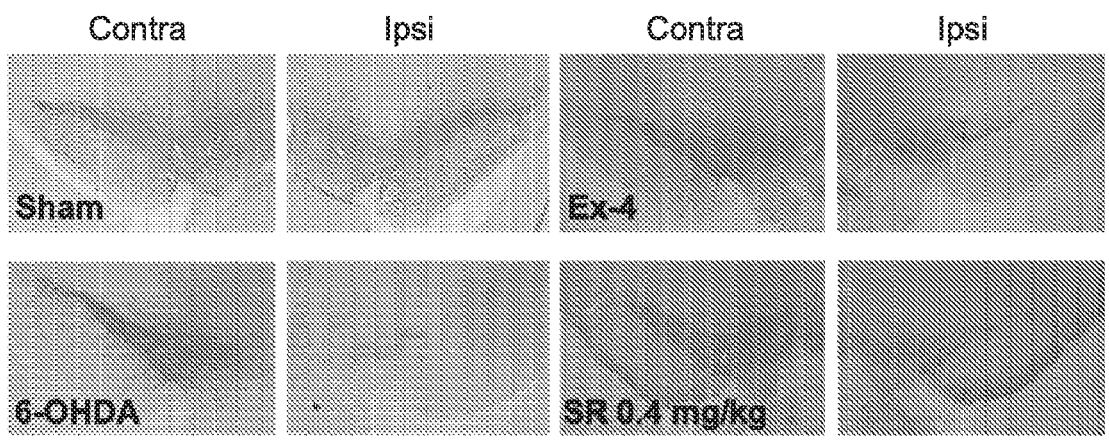
FIG. 6C. Representative microscopy images of substantia nigra from control (Sham) rats, 6-OHDA rats, Exendin-4 treated 6-OHDA rats, and PT302 treated 6-OHDA rats.
Figure 6D:
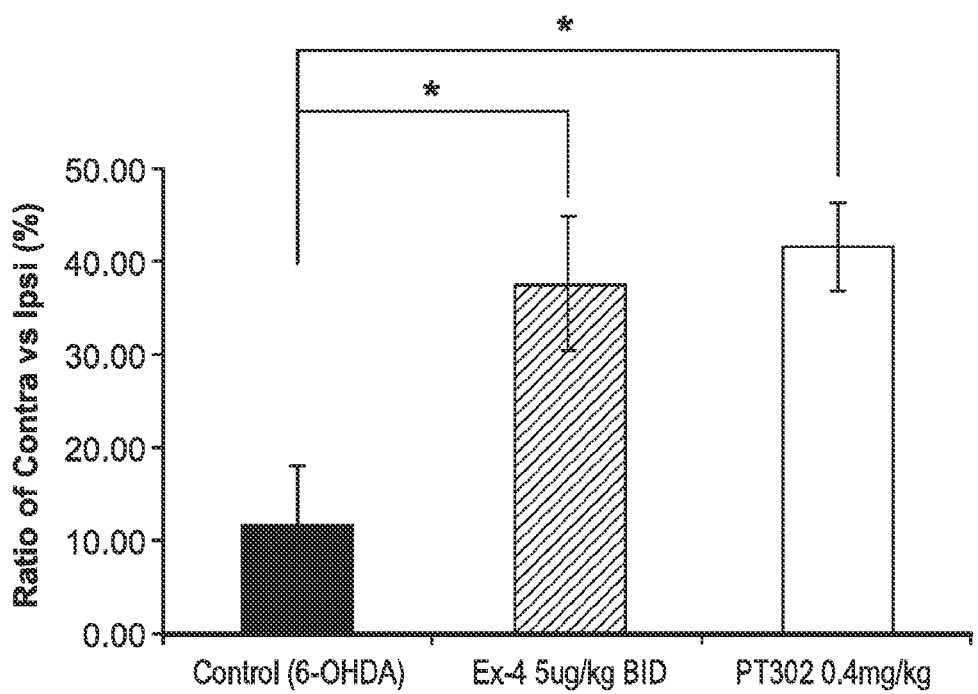
FIG. 6D. A graph illustrating the quantified data of FIG. 6C.

Representative TH immunoreactivity from sham animals and 6-OHDA-lesioned animals receiving vehicle, Ex-4 (5 μg/kg, BID) or PT302 (0.4 mg/kg) is shown in FIG. 6C. The injection of 6-OHDA significantly reduced TH immunoreactivity on the side of the lesion (noted as ipsi in FIG. 6C). Representative TH immunoreactivity in substantia nigra was quantified and shown in FIG. 6D. Treatment with PT302 and Ex-4 significantly reduced the loss of TH immunoreactivity on the 6-OHDA lesioned side (evaluated by expressing TH immunoreactivity as a ratio of immunoreactivity present on the side of the lesion (ipsi) as a percent of immunoreactivity present in the same animal on the control unlesioned side (contra)).

Figure 7A:
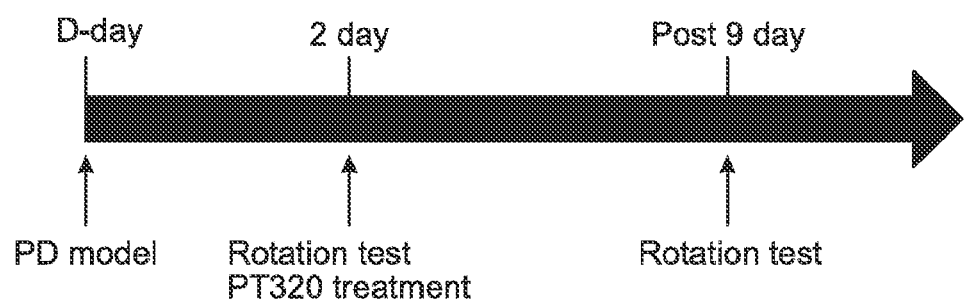
FIG. 7A. Outline of the study design of Example 5.
Figure 7B:
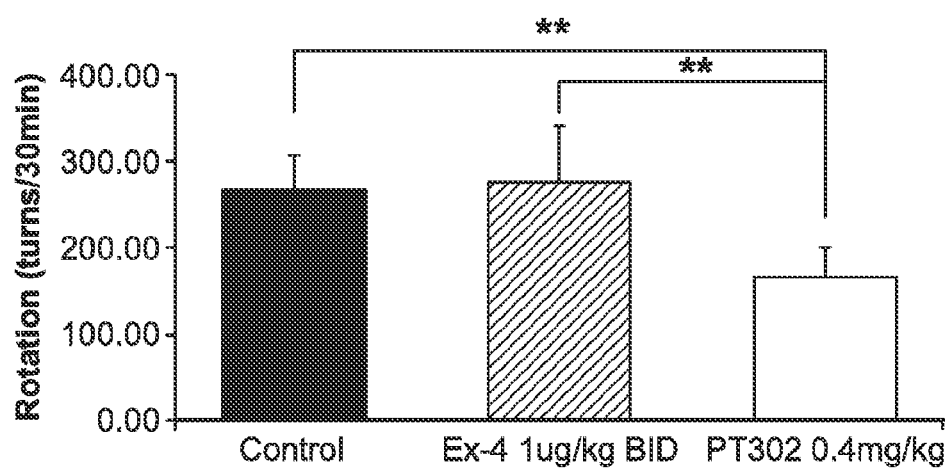
FIG. 7B. PT302 significantly reduced rotational behavior in unilaterally 6-OHDA-lesioned rats, while Exendin-4 did not reduce rotational behavior in unilaterally 6-OHDA-lesioned rats.

Example 5. Post-Treatment with PT302 Reduces Meth-Mediated Rotation in a 6-OHDA Rat Model of Parkinson's Disease Animals were treated with Ex-4 (1 μg/kg, BID from day 2) or PT302 (0.4 mg/kg, once on day 2) after 6-OHDA lesioning and meth-mediated rotational behavior was examined on day 9 after lesioning, as described above (FIG. 7A). As shown in FIG. 7B, PT302 significantly reduced rotation behavior in the unilaterally 6-OHDA-lesioned rats (p=0.0075). In contrast, Exendin-4 did not reduce rotational behavior in the unilaterally 6-OHDA-lesioned rats. Thus, the use of Exendin-4 at a human equivalent dose (1 μg/kg BID in rat) proved ineffective in mitigating meth-induced rotation, whereas PT302 at a human translatable dose proved effective in the 6-OHDA rat PD model. When the Exendin-4 dose was escalated to an equivalent that is higher than the human achievable dose (5 μg/kg BID, as in Example 4), Exendin-4 could provide mitigation of 6-OHDA induced impairments. By contrast, an equivalent clinically translatable dose of PT302 provides favorable actions in both Example 4 and 5.

Figure 8A:
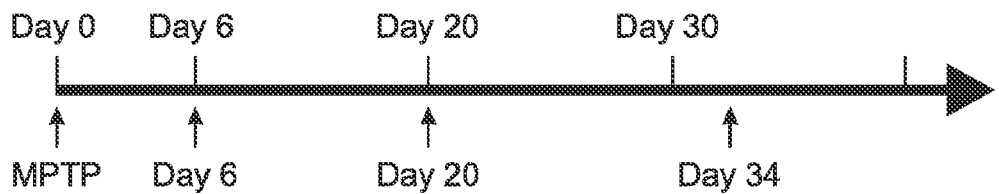
FIG. 8A. Outline of the study design of Example 6.

Example 6. Post-Treatment with PT302 Improved Toxin-Induced Behavior Deficit in a MPTP-Mouse Model of PD Animals were treated with Ex-4 (16.7 ug/kg, BID from day 6) or PT302 (0.6 mg/kg, on days 6, 20, and 34) after the induction of Parkinsonism by MPTP, as described above (FIG. 8A). Specifically, Parkinsonism was induced by the systemic administration of 30 mg/kg MPTP daily, for 5 days. See, e.g., Filichia E, Hoffer B, Qi X, Luo Y. Inhibition of Drp1 mitochondrial translocation provides neural protection in dopaminergic system in a Parkinson's disease model induced by MPTP. Sci Rep. 2016; 6:32656. Treatment with either Ex-4 or PT302 was initiated one day after the first MPTP dose, and continued for 18 days. The selected doses of Ex-4 (16.7 ug/kg BID subcutaneous) and PT302 (0.4 mg/kg single dose subcutaneous) were equivalent in relation to Ex-4 amount delivered, and provided 601.2 ug/kg and less than 600 ug/kg, respectively, over the 18 days of treatment. A wire grip test was utilized to evaluate locomotor coordination of all groups of animals on day 18. The wire grip test (also known as the paw grip endurance (PaGE) method and the grip force-recording test) are often used as measures of motor strength. PaGE is designed to assess the grip strength of mice, which may be indicative of a decrease in motor skills and was performed here as described by Jessica A L, et al. (Jessica A. L. Hutter-Saunders, Howard E. Gendelman, R. Lee Mosley. Murine Motor and Behavior Functional Evaluations for Acute 1-Methyl-4-Phenyl-1,2,3,6-Tetrahydropyridine (MPTP) Intoxication. J Neuroimmune Pharmacol. 2012; 7(1): 279-288). Briefly, each mouse was placed on a wire lid from a conventional rodent housing cage; the lid was gently shaken to induce gripping and turned upside down (180°). The latency until the mouse released both hind limbs was measured in seconds. Each mouse was tested three times with an arbitrary maximum of 240 s, and the longest latency to fall or release both hind limbs was recorded (Jessica, et al. 2012).

Figure 8B:
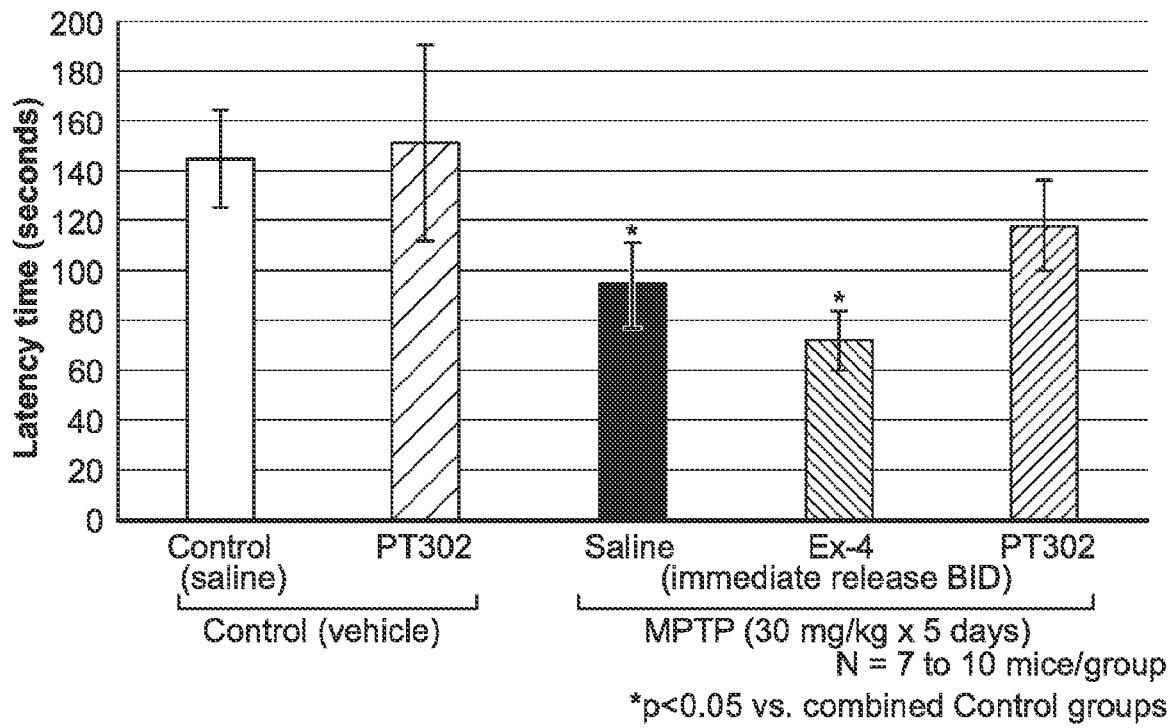
FIG. 8B. A graph illustrating that PT302 significantly increases the time to fall from a wire in MPTP-treated mice, while Exendin-4 did not increase the time to fall from a wire.

As shown in FIG. 8B, the administration of the dopaminergic cell toxin, MPTP, resulted in a significantly reduced latency time in the Grip test (MPTP: 94.5 sec vs. the combined Control group without MPTP: 148.3 sec; p=0.02). PT302 significantly increased the time to fall from the wire in the MPTP-treated mice (118.3 sec, not statistically different from the combined Control group value), while Exendin-4 (administered twice daily, in a manner similar to human use of Byetta (i.e., immediate release Ex-4)) did not mitigate the toxin-induced behavioral deficit in the MPTP-treated mice (72.9 s, p+0.01 vs. the combined Control group value) (FIG. 8B: across all groups, the number of mice was between 7 and 10).

Example 7. Delivering Ex-4 to the Central Nervous System by Sustained Release Exendin-4 is Effective at Achieving Therapeutic Amounts of Exendin-4 in the Cerebral Spinal Fluid Exendin-4 (injection and minipump) and sustained release formulation of Exendin-4 (PT302) were administered as described in Table 1 to adult male Sprague-Dawley rats (9 weeks old) were used for this study. Blood and cerebrospinal fluid (CSF) were collected on day 14 after first injection of Exendin-4 administration for measurement of Exendin-4 levels. Plasma and CSF levels of Exendin-4 were quantified as described above. As shown in Table 2, Exendin-4 was detected in the plasma and CSF of the sustained release formulation group and the minipump administered Exendin-4 group, while Exendin-4 was below the detectable limits in the CSF in the twice daily (BID, immediate release) Exendin-4 group. This is in contrast to the high levels of Exendin-4 detected in the plasma of this Exendin-4 group. CSF/plasma level ratios ranged from 0.0081 (or 0.81%) to about 0.0412 (or 4.12%) with an average of 0.018 (or 1.8%) was observed in pump administered Exendin-4 with doses ranging from 3.5-15 pM/kg/min. Likewise, CSF/plasma level ratios ranged from 0.0117 (or 1.17%) to about 0.016 (or 1.6%) in animals administered PT302 0.46-2.0 mg/kg/14 days. This data demonstrates that the sustained release of Exendin-4 provides greater levels of Exendin-4 into the CNS.

TABLE 1

| Experimental procedure | | | | |
|---|---|---|---|---|
| Ex-4 BID (immediate release) | Ex-4 in 14 day Mini-pump | PT302 | Rational | Animals |
| 2.3 ug/kg/day (1.15 BID) | 3.5 pM/kg/min | 0.46 mg/kg/14 days | Daily dose conversion | 5 rats/group |
| 4.6 ug/kg/day (2.3 BID) | 7.0 pM/kg/min | 0.92 mg/kg/14 days | Daily dose x2 | 5 rats/group |
| 10.0 ug/kg/day (5 BID) | 15 pM/kg/min | 2.0 mg/kg/14 days | Match plasma level | 5 rats/group |

TABLE 2

Plasma and Cerebral Spinal Fluid Levels in rats treated with Exendin-4 via a Minipump, PT302, and Exendin-4

| Formulation | Dose | Plasma | CSF | CSF/Plasma ratio |
|---|---|---|---|---|
| Pump (low) | 3.5 pM/kg/min | 394.8484 | 14.88721 | 0.041279 |
| Pump (medium) | 7.0 pM/kg/min | 4293.409 | 35.0529 | 0.008159 |
| Pump (high) | 15 pM/kg/min | 7899.634 | 137.688 | 0.0185 |
| PT302(low) | 0.46 mg/kg/14 days | 1853.329 | 18.28185 | 0.01612 |
| PT302(medium) | 0.92 mg/kg/14 days | 4438.496 | 54.37036 | 0.012756 |
| PT302(high) | 2.0 mg/kg/14 days | 2316.801 | 29.98072 | 0.011789 |
| Ex-4 low | 2.3 µg/kg/day (1.15 BID) | 93.479 | Under LLOQ | N/A |
| Ex-4 Medium | 4.6 µg/kg/day (2.3 BID) | 576.886 | Under LLOQ | N/A |
| Ex-4 High | 10 µg/kg/day (5 BID) | 5819.282 | Under LLOQ | N/A |

Example 8. Sustained Release Exenatide Treatment of Mild Traumatic Brain Injury (mTBI) Mice Improves Novel Object Recognition The head injury was performed using the weight drop trauma device as previously described (Tweedie et al. 2007). The device consists of a metal tube (90 cm long, 1.3 cm inner diameter) and a sponge under the tube to support the head of the mice. The mice were lightly anesthetized by inhalation of isoflurane and put under the device. A metal weight (30 grams) was dropped from the top of the tube to strike the head of the mouse at the temporal side between the corner of the eye and the ear. Immediately following the injury, the mice were put back in their original cage for recovery. This head injury procedure is well tolerated by mice and results in a diffuse neuronal loss in the hippocampus and cerebral cortex on the side of injury, and is accompanied by cognitive impairment in visual and spatial memory tests (Deselms H, Maggio N, Rubovitch V, Chapman J, Schreiber S, Tweedie D, Kim D S, Greig N H, Pick CG. Novel pharmaceutical treatments for minimal traumatic brain injury and evaluation of animal models and methodologies supporting their development. J Neurosci Methods. 2016; 272:69-76).

Figure 9A:
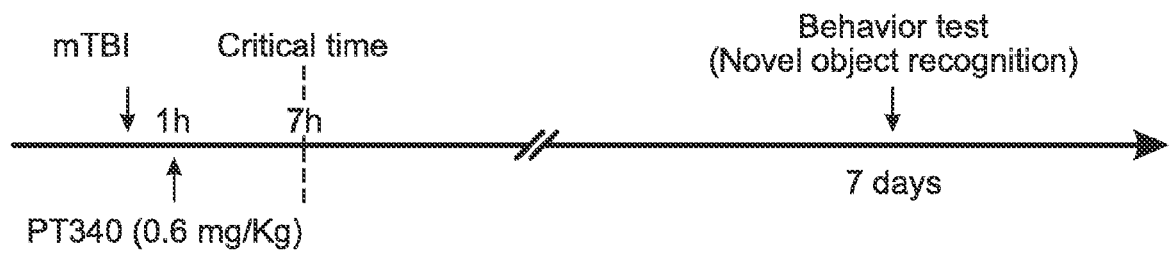
FIG. 9A. Outline of the study design of Example 8.
Figure 9B:
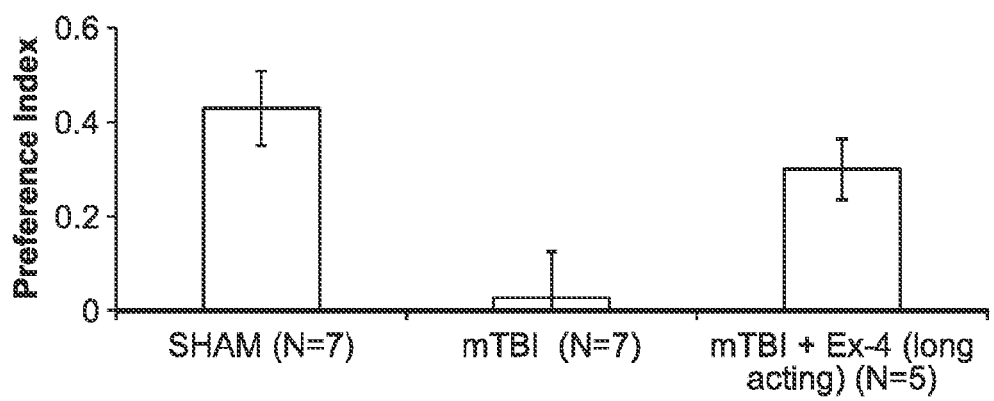
FIG. 9B. A graph illustrating that sustained release Exenatide significantly increased novel object recognition in mild traumatic brain injury (mTBI) challenged mice.

Sustained release PT302 was administered (0.6 mg/kg, s.c.) 1 hour post head injury, as described above (FIG. 9A). The mice were tested 7 days post injury for the novel object recognition paradigm, which is routinely used to evaluate recognition memory in rodents. Non-compromised rodents display an inherent tendency to explore novel objects in their immediate locations. This feature of mouse behavior allows for the assessment of visual recognition memory function. Perhaps more importantly, it also allows for the assessment of the effects of different stimuli on this inherent activity. The test utilizes two trials. In the first trial, animals are allowed to examine two objects for a defined amount of time-5 minutes. The second trial takes place 24 hours after the first, in which the animals are challenged with two objects where one is the same as in the first trial and the other is new to the animal. In the second trial mice are also allowed to explore the objects for 5 minutes. A discrimination preference index is calculated and used to evaluate the animal's recognition memory. The index is calculated by the following: the time the animal spends near the novel object minus the time spent near the familiar object, divided by the sum of the time near the novel and familiar objects (Dix S L, Aggleton J P. Extending the spontaneous preference test of recognition: evidence of object-location and object-context recognition. Behav. Brain Res. 1999; 99:191-200). As shown in FIG. 9B, administration of Exenatide significantly increased novel object recognition in mTBI mice (n=5), as compared to untreated mTBI mice (n=7), thereby demonstrating that the PT302 treated mice mitigated the visual recognition impairment induced by the mTBI.

Example 9. Examination of Plasma Exendin-4 Level in Normal ICR Mice

Figure 10A:
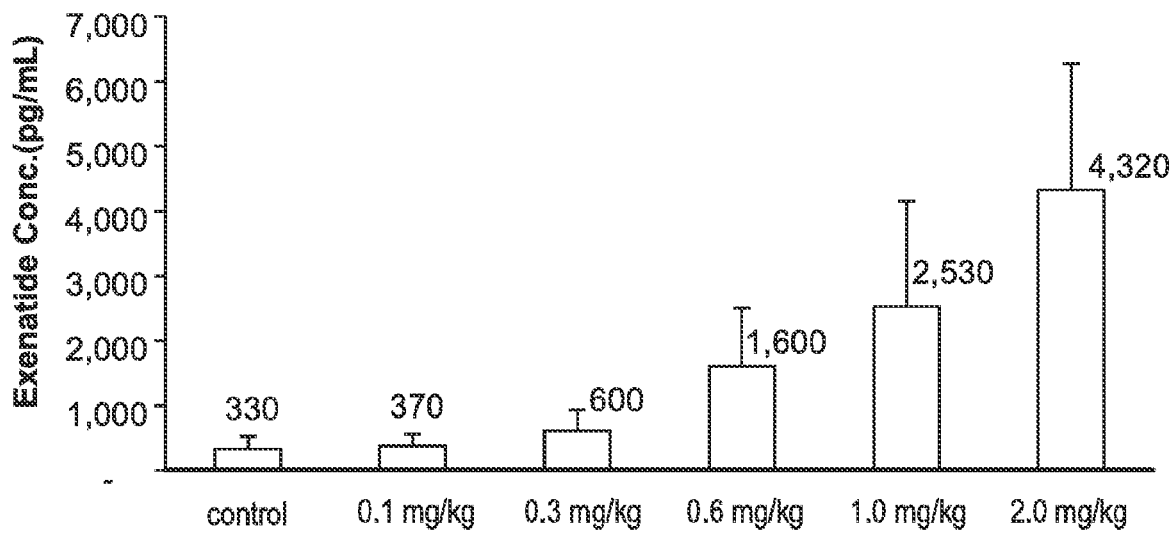
FIG. 10A. A graph illustrating that Exendin-4 plasma levels are sustained for seven days post PT302 administration and, additionally, are dose-dependent.

Exendin-4 plasma concentration was measured in normal ICR mice 7 days after subcutaneous administration of PT302 (0.1, 0.3, 0.6, 1.0, and 2.0 mg/kg). Plasma levels of Exendin-4 were quantified as described above. The plasma Exendin-4 level is sustained and dose-dependently accumulated up to about 4000 pg/ml until 7 days after injection (FIG. 10A).

Figure 10B:
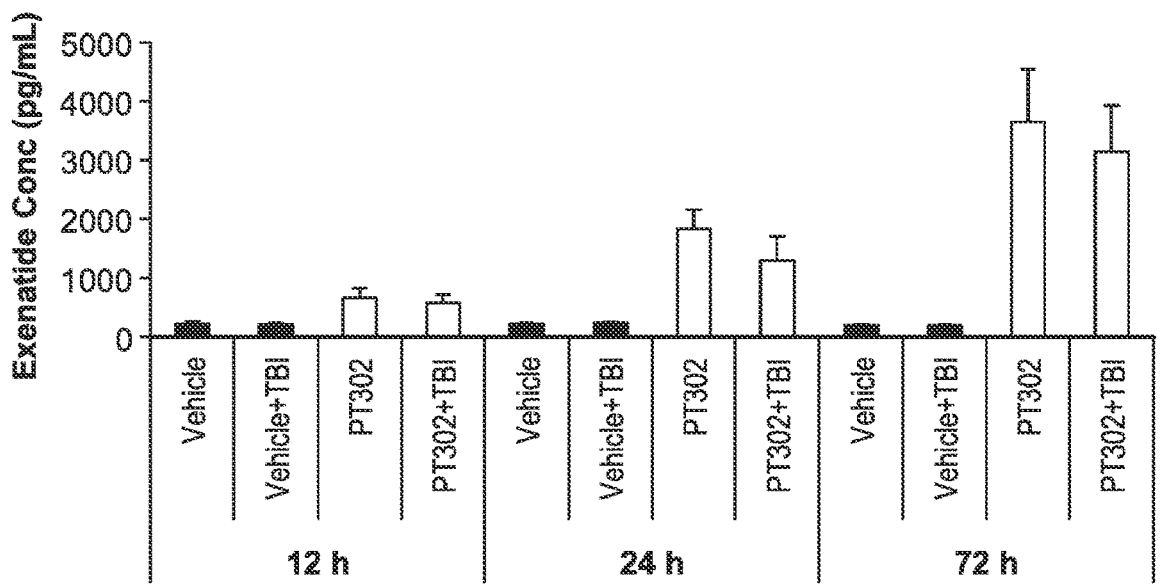
FIG. 10B. A graph illustrating a significant difference in Exendin-4 plasma levels deriving from PT302 administration was not observed between normal/control mice and mTBI-challenged mice.

Example 10. Examination of Plasma Exendin-4 Levels in Normal and Traumatic Brain Injury Mice Exendin-4 plasma levels were measured in normal mice and TBI model mice 7 days after subcutaneous administration of PT302 (0.6 mg/kg). Plasma levels of Exendin-4 were quantified as described above. No differences were observed in Exendin-4 plasma levels between normal mice and TBI-induced mice (FIG. 10B).

Figure 10C:
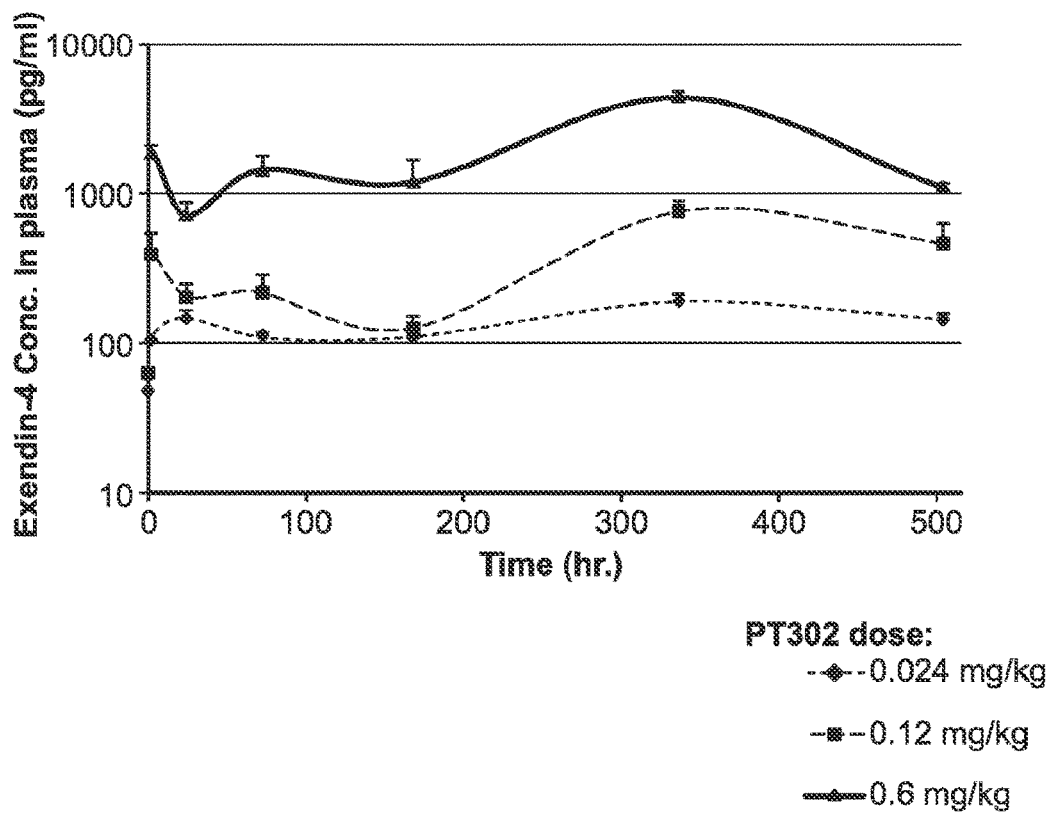
FIG. 10C. A graph illustrating that three different doses of sustained release Exenatide (PT302: 0.024, 0.12 and 0.6 mg/kg) were able to accumulate and be time-dependently maintained in the plasma.

Example 11. Sustained Release Exenatide Maintains Exendin-4 Plasma Levels for an Extended Period of Time Normal ICR mice received a single subcutaneous injection of PT302 at three different doses: 0.024 mg/kg, 0.12 mg/kg, and 0.6 mg/kg. Blood was collected at 0 hours, 0.5 hours, and 1 hour after the first injection, and on day 1, 3, 7, 14, and 21 days for plasma measurement. The plasma concentration of Exendin-4 was quantified as described above. As shown in FIG. 10C, a single dose of PT302 maintained Exendin-4 plasma levels for more than 20 days.

Example 12. Sustained Release Exenatide Significantly Increases Recognition of Novel Objects and New Arms of a Maze Seven Days after Traumatic Brain Injury The head injury was performed as described above and the mice immediately placed in their original cage for recovery. PT302 (0.024 mg/kg, 0.12 mg/kg, and 0.6 mg/kg) was administered subcutaneously to mice as a single injection 1 hour after the induction of TBI. Behavioral assessments (novel object recognition and Y-maze test) were conducted 7 days post mTBI. The Y-maze paradigm is commonly used to evaluate spontaneous exploration and responsiveness to novel environments and spatial working memory function (Deselms, et al., 2016). The test apparatus is constructed out of identical black Plexiglass arms (8×30× 15 cm) where the arms extend from a central point at a 120° angle from the center. Inside each arm is a different spatial cue designed to give the mouse a visual memory anchor. Typically, there are two trials undertaken a few minutes apart; here the trials were undertaken at 5 minute intervals. For each first trial, the start arm is selected randomly. Each animal is placed into the center point of the Y maze environment; during the first 5 minute trial, one of the two arms is randomly closed, during the second 2 minute trial all three arms are open for exploration. The total amount of time the mouse explored in each arm during the second trial is recorded. To avoid any possible confounds, between trials the T maze is thoroughly cleaned. The time spent in the novel previously unexplored arm over the familiar previously explored arm is used to assess for any behavioral differences between each animal treatment group i.e. (the time spent in new arm minus time spent in familiar arm)/ (time spent in new arm plus time spent in familiar arm).

Figure 11A:
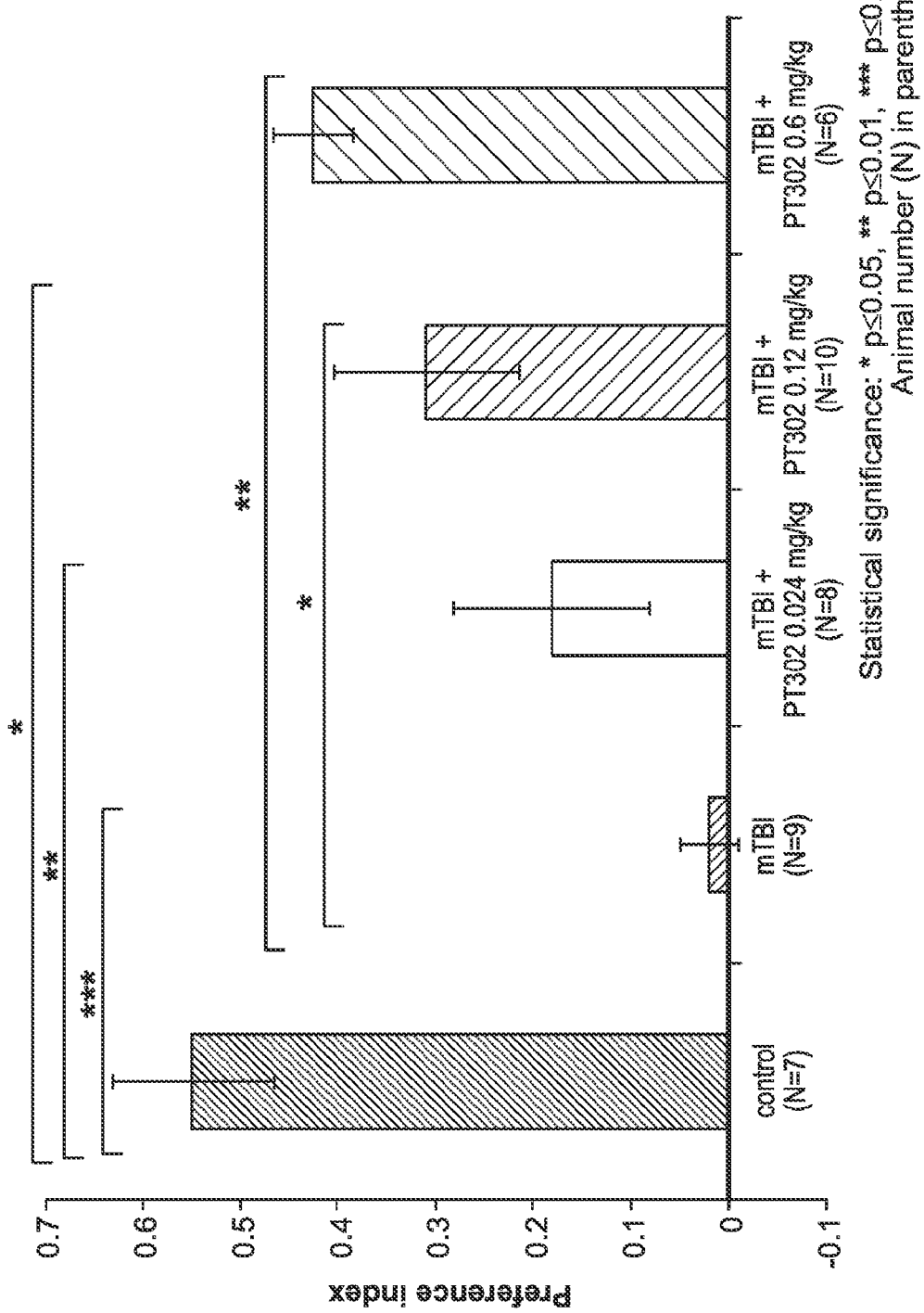
FIG. 11A. A graph illustrating that sustained-release Exenatide (PT302: 0.024, 0.12 and 0.6 mg/kg) resulted in a high preference for new objects in mTBI-challenged mice, as compared to untreated mTBI-challenged mice that suffered from visual memory deficits and spent less time near the novel objects; as evaluated at 7 days following mTBI by the Novel Object Recognition paradigm.
Figure 11B:
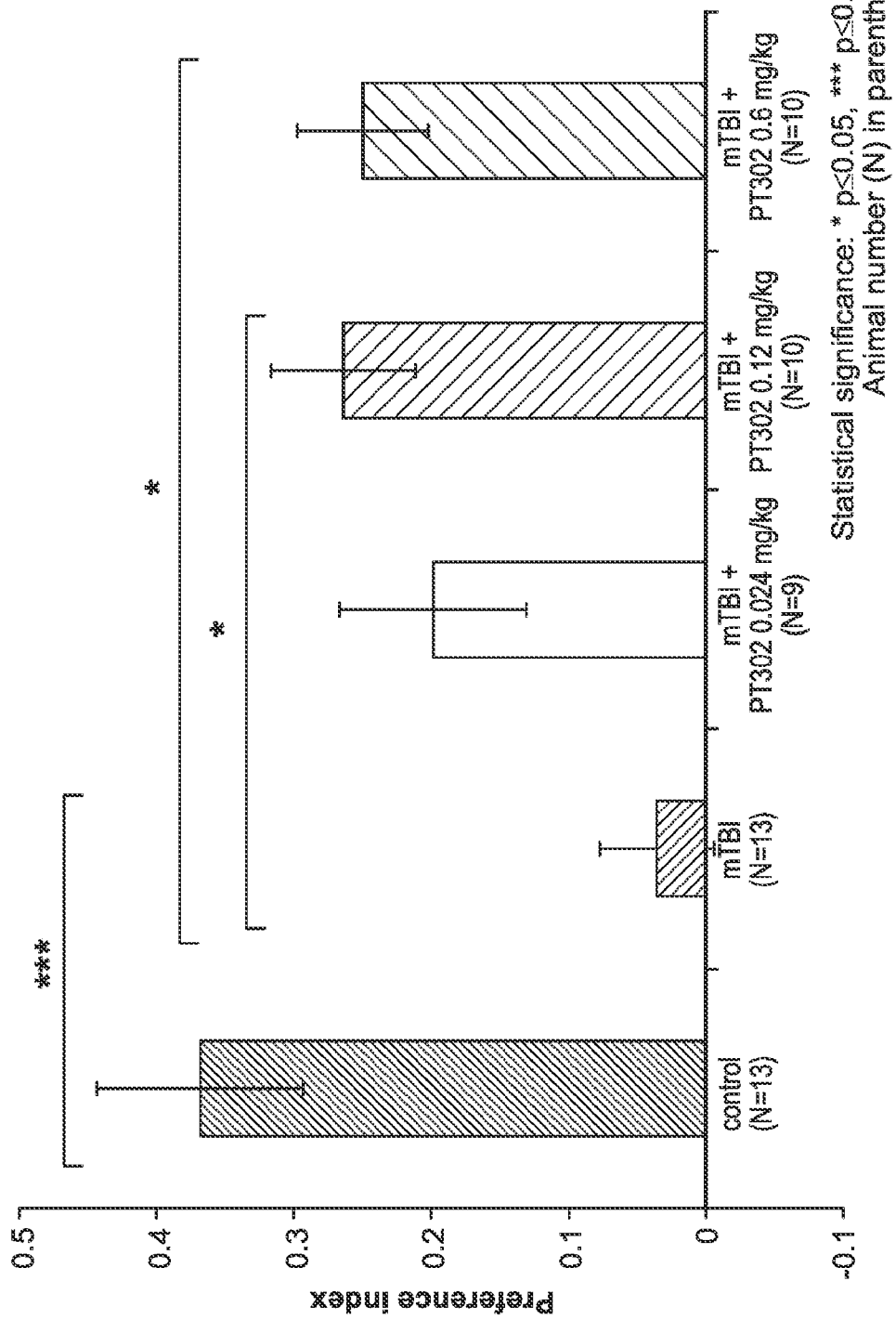
FIG. 11B. A graph illustrating that sustained-release Exenatide (PT302: 0.024, 0.12 and 0.6 mg/kg) ameliorated the mTBI-spatial memory deficit observed in untreated mTBI-challenged mice as evaluated by Y-maze at 7 days following mTBI.

Vehicle-treated mTBI mice suffered from visual memory deficits and spent less time near the novel object as compared to control mice ($p<0.001$) (FIG. 11A). A high preference for the new object as compared to untreated mTBI mice was observed in mice treated with a single subcutaneous injection of PT302 1 hour following mTBI induction at a dose of 0.12 mg/kg ($p<0.05$) and 0.6 mg/kg ($p<0.01$) (FIG. 11A).

mTBI-challenged mice demonstrated a significant impairment in spatial memory, and spent less time in the new arm of the Y maze as compared to sham (control) animals ($p<0.001$) (FIG. 11B). A single subcutaneous injection of PT302 1 hour following mTBI induction at a dose of 0.12 mg/kg and 0.6 mg/kg ameliorated the mTBI-spatial memory deficit as compared to untreated mTBI mice ($p<0.01$) (FIG. 11B). [$F(4,50)=4.83$, $p=0.002$, Fisher's LSD post hoc].

All groups spent approximately equal time in the open arm of the elevated plus maze and could not be differentiated from one another with regard to their anxiety-like behavior (FIG. 11C); importantly indicating that anxiety-like behavior was not a confounding factor in the prior novel object recognition and Y-maze paradigms ($p>0.05$). [$F(4,36)=0.28$, $p=0.89$].

Example 13. Sustained Release Exenatide Significantly Increases Recognition of Novel Objects and New Arms of a Maze Thirty Days after Traumatic Brain Injury The head injury was performed as described above and the mice immediately placed in their original cage for recovery. PT302 (0.6 mg/kg) was administered subcutaneously to mice as a single injection 1 hour after the induction of TBI. Behavioral assessments (novel object recognition and Y-maze test) were conducted 30 days post mTBI.

Vehicle-treated mTBI mice suffered from visual memory deficits and spent less time near the novel object as compared to control mice ($p<0.001$; FIG. 12A). A high preference for the new object as compared to mTBI mice was observed in mice that were treated with a single subcutaneous injection of PT302 1 hour following mTBI induction at a dose of 0.12 mg/kg or 0.6 mg/kg ($p<0.01$ and $p<0.001$, respectively; FIG. 12A).

mTBI-challenged mice demonstrated a significant impairment in spatial memory, and spent less time in the new arm of the maze as compared to sham/control animals ($p<0.001$; FIG. 12B). A single subcutaneous injection of PT302 1 hour following mTBI induction at a dose of 0.6 mg/kg ameliorated the mTBI-spatial memory deficit as compared to mTBI alone ($p<0.01$; FIG. 12B).

All groups spent approximately equal time in the open arm of the maze and could not be differentiated from one another in regards to their anxiety-like behavior (FIG. 12C), indicating that anxiety-like behavior was not a factor in the prior novel object recognition and Y-maze paradigms ($p>0.05$).

Example 14. PT302 Administration Prevented the Decline in NeuN Immunoreactivity Subsequent to Traumatic Brain Injury in Mouse Temporal Cortical and Hippocampal Regions NeuN is a mature neuron marker, which can be used to assess neuron loss due to traumatic brain injury. For evaluation of NeuN cells in defined brain regions, mice were anesthetized by excess ketamine+xylazine administration and were immediately perfused transcardially with physiological buffered saline followed by 4% paraformaldehyde ((PFA) in 0.1 M phosphate buffer, pH 7.4). Their brains were removed, fixed overnight (4% PFA in 0.1 M phosphate buffer, pH 7.4), and then placed in 30% sucrose for 48 hours. Coronal sections (30 µm) were cut on a cryostat, placed in cryoprotectant, and stored at −20° C. until use. Thereafter, 5 sections of cortex and 5 of hippocampus were blocked by incubation with 0.1% Triton X-100 in phosphate-buffered saline (PBST) and 10% normal horse serum for 1 hour at 25° C. The primary antibody, mouse anti-neuronal nuclei (NeuN; 1:50, Millipore, Danvers, Mass., USA, Cat # MAB3377) was then dissolved in PBST and 2% normal horse serum and incubated with the sections for 48 hours at 4° C. Following rinsing in PBST, the sections were incubated for 1 hour at 25° C. with DyLight™ 594-conjugated AffinityPure Donkey Anti-rabbit IgG and DyLight™ 488-conjugated AffinityPure Donkey Anti-mouse IgG (1:300; Jackson Laboratories, Bar Harbor, Me., USA). After rinses in PBST, the sections were mounted on dry gelatin-coated slides and evaluated for fluorescence with a Zeiss LSM 510 confocal microscope with ×20 and ×63 lens (Carl Zeiss, Jena, Germany). For each brain, three to five sections were taken and the average numbers of cells within the hippocampus and the temporal cortex were calculated within defined fields of either 140² or 440² μM. Evaluation of immunohistochemical slides for immunofluorescence was undertaken in a blinded manner, and the omission of the primary antibody was routinely undertaken in the generation of negative control sections. Analyses were performed by Imaris program for color quantification (Bitplane AG, Zurich, Switzerland).

Figure 13A:
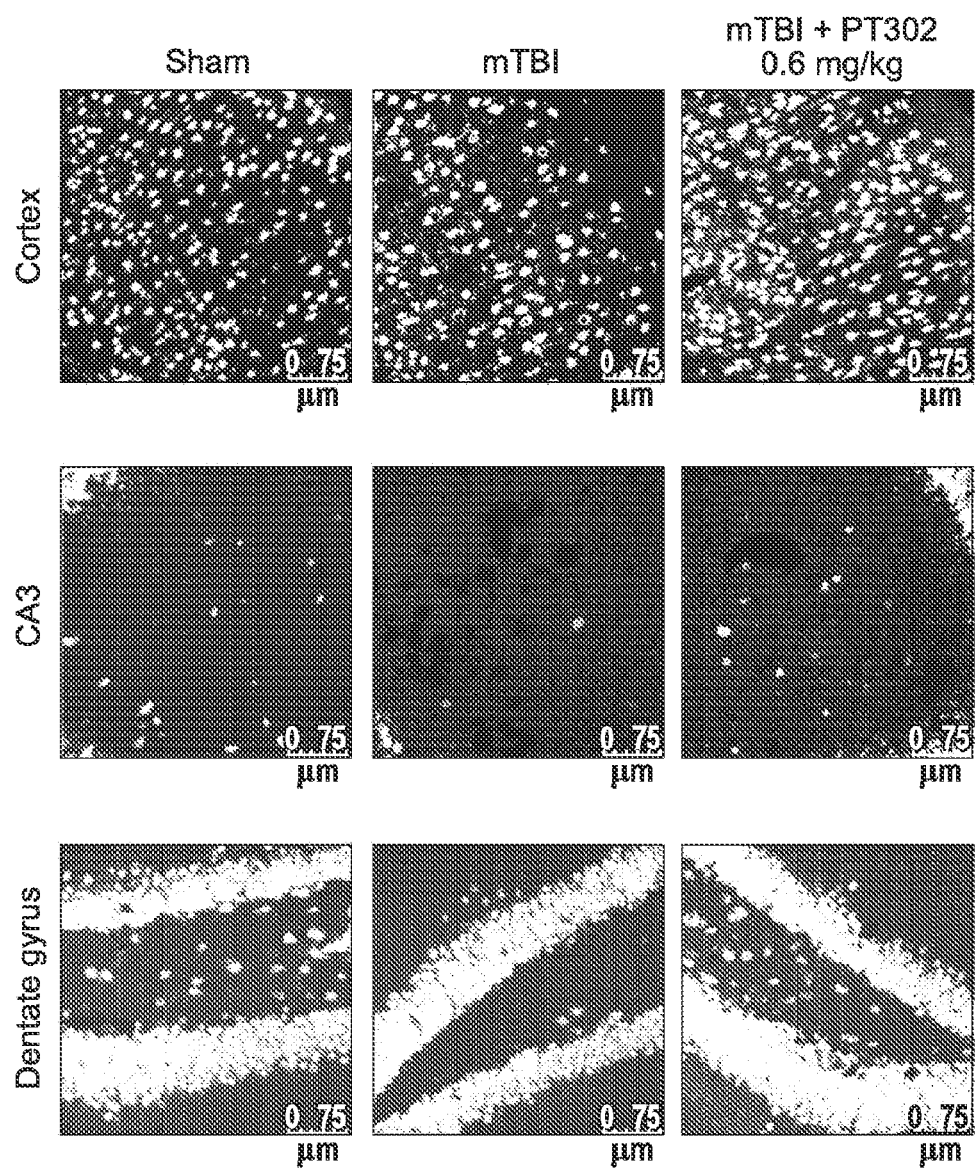
FIG. 13A. Representative images illustrating that sustained-release Exenatide (PT302 0.6 mg/kg) was able to prevent the decline in neurons observed in the cortex, CA3, and dentate gyrus of mTBI-induced mice.
Figure 13B:
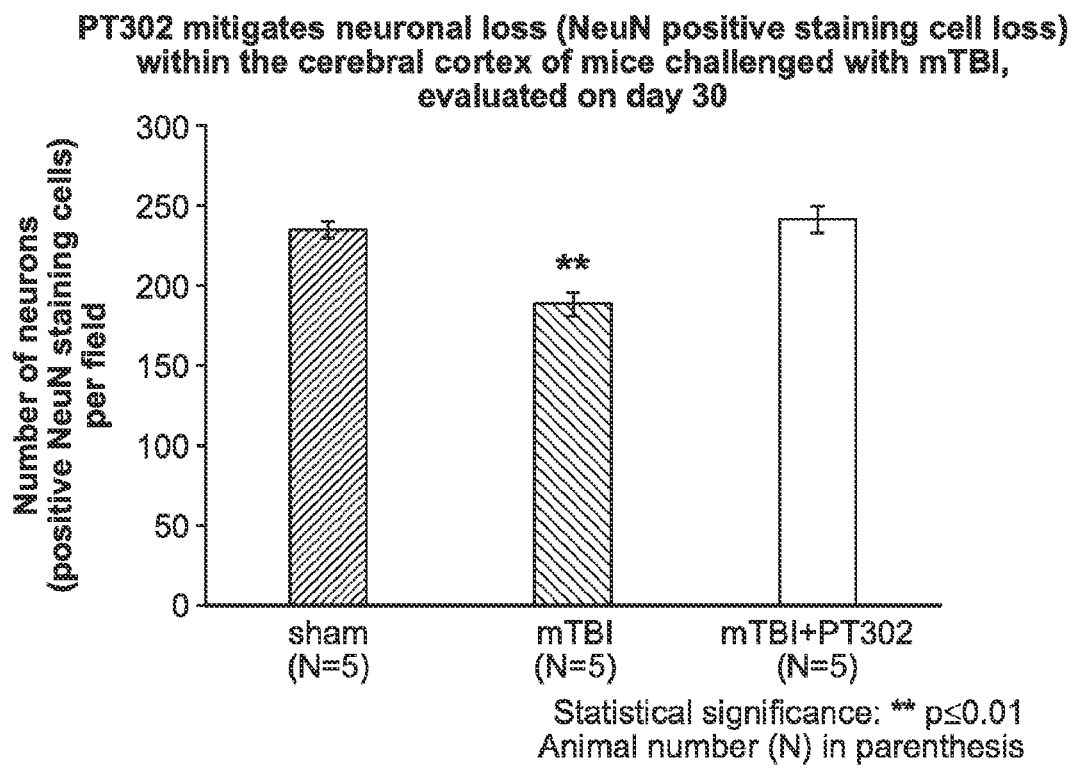
FIG. 13B. A graph illustrating the quantification of the cerebral cortex data associated with the representative images in FIG. 13A, which demonstrates that sustained-release Exenatide (PT302 0.6 mg/kg) was able to prevent the decline in neurons observed in the cerebral cortex of mTBI-induced mice.
Figure 13C:
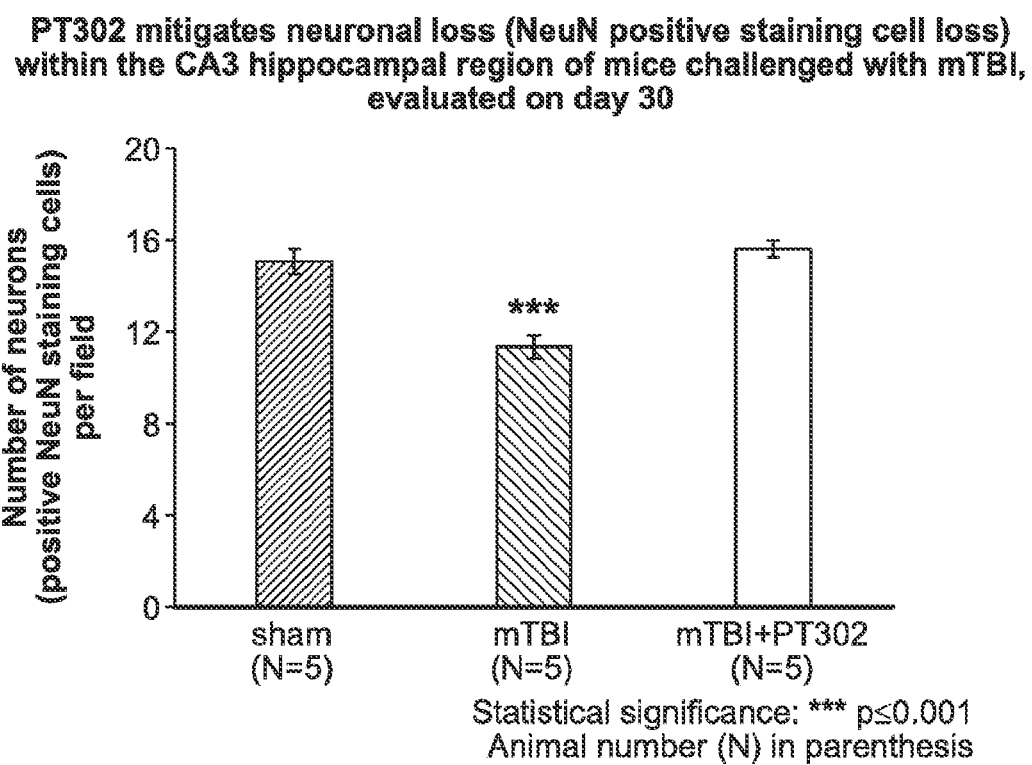
FIG. 13C. A graph illustrating the quantification of the CA3 data associated with the representative images in FIG. 13A, which demonstrates that sustained-release Exenatide (PT302 0.6 mg/kg) was able to prevent the decline in neurons observed in the CA3 region of the hippocampus of mTBI-induced mice.
Figure 13D:
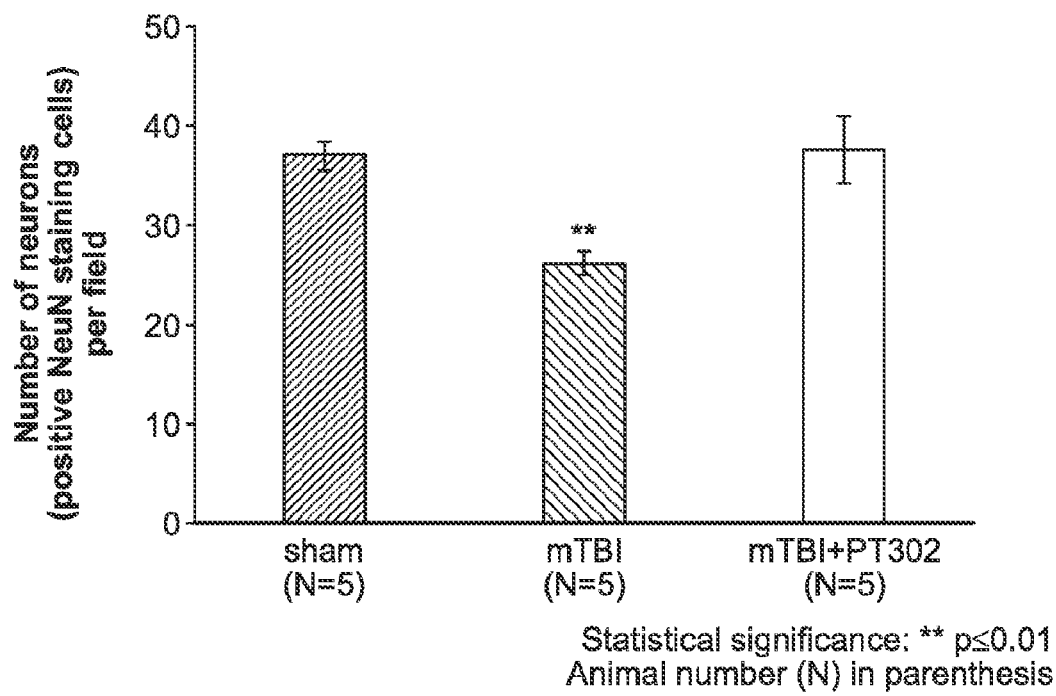
FIG. 13D. A graph illustrating the quantification of the dentate gyrus data associated with the representative images in FIG. 13A, which demonstrates that sustained-release Exenatide was able to prevent the decline in neurons observed in the dentate gyrus region of the hippocampus of mTBI-induced mice.

FIG. 13A shows representative images of NeuN (red (when evaluated in color)) positive neurons in the cortex, CA3 and dentate gyrus of control mice, untreated mTBI mice, and PT302 treated mTBI mice (0.6 mg/kg 1 hour post mTBI) 30 days post mTBI. Bar graphs of FIGS. 13B, 13C, and 13D show the quantification of neuronal survival in the cortex, CA3 and the dentate gyrus, respectively, as was measured by the number of neurons positively stained with anti-NeuN in sham control, mTBI and mTBI+PT302 0.6 mg/kg groups. ($p<0.01$, *$p<0.001$). Values are mean±SEM. Administration of sustained-release Exendin-4 in the form of PT302 prevented the neuron loss observed due to traumatic brain injury.

Example 15. PT302 Administration Decreased the Number of Degenerating Neurons in mTBI Mice Fluoro-Jade® C is a fluorescent stain that labels injured, degenerating brain neurons, which may be utilized to assess neuron loss due to traumatic brain injury. Ionized calcium-binding adaptor molecule 1 (IBA1) is specifically expressed in microglia and upregulated in activated microglia, which may be utilized as a marker of neuroinflammation. Mice were euthanized and their brains prepared for immunohistochemical analyses as described above. Coronal sections from hippocampus and parietal cortex (40 μm) were cut on a cryostat and collected in a cryoprotectant solution. CA1, CA3 and dentate gyrus from the hippocampus, in addition to the parietal cortex were analysed.

For FluoroJade C staining, brain sections were first immersed in a solution containing 1% NaOH in 80% ethanol for 5 minutes. They were rinsed for 2 minutes in 70% ethanol, washed in distilled water, then incubated in 0.06% potassium permanganate solution for 10 minutes. Following a water wash, slides were incubated in the FJC staining solution (obtained by adding 4 ml of a FJC 0.01% stock solution in distilled water to 96 ml of 0.1% acetic acid) and stained for 10 minutes. After 3 washes with distilled water, slides were fully air-dried on a slide warmer, cleared in xylene and coverslipped with DPX. Fluorojade C positive cells were counted for each region in both hemisphere, by a FV 1000MPE Olympus confocal microscope.

For IBA1/TNF-α double labelling, sections were incubated 48 hours with IBA1 antibody (polyclonal goat anti-IBA1 1:200, Abcam, USA) and TNF-α antibody (TNF-α polyclonal rabbit anti-TNF-α 1:800, Abbiotec, USA). After PBS washing, the sections were incubated with secondary antibody for IBA1 while three-step detection was used to increase the signal of TNF-α by biotin-conjugated IgG (IgG (H+L) Biotin-Goat anti rabbit 1:500, Invitrogen, USA) and streptavidin-fluorescein (1:200, Vector, UK).

Qualitative and quantitative analyses for IBA1 and TNFα were performed using a FV 1000MPE, Olympus confocal laser scanning microscope. Z-series images were processed by ImageJ 1.47v and volume of colocalized elements was measured by Imaris 7.4.2 as follows: for each dataset, a colocalization channel was automatically composed by the software. In the final stacks, a region of interest for each brain region (CA1, CA3, DG and Cortex) per hemisphere of each animal was chosen, and volume of the elements of interest was calculated, summed and expressed as volume/ μm3.

Figure 14A:
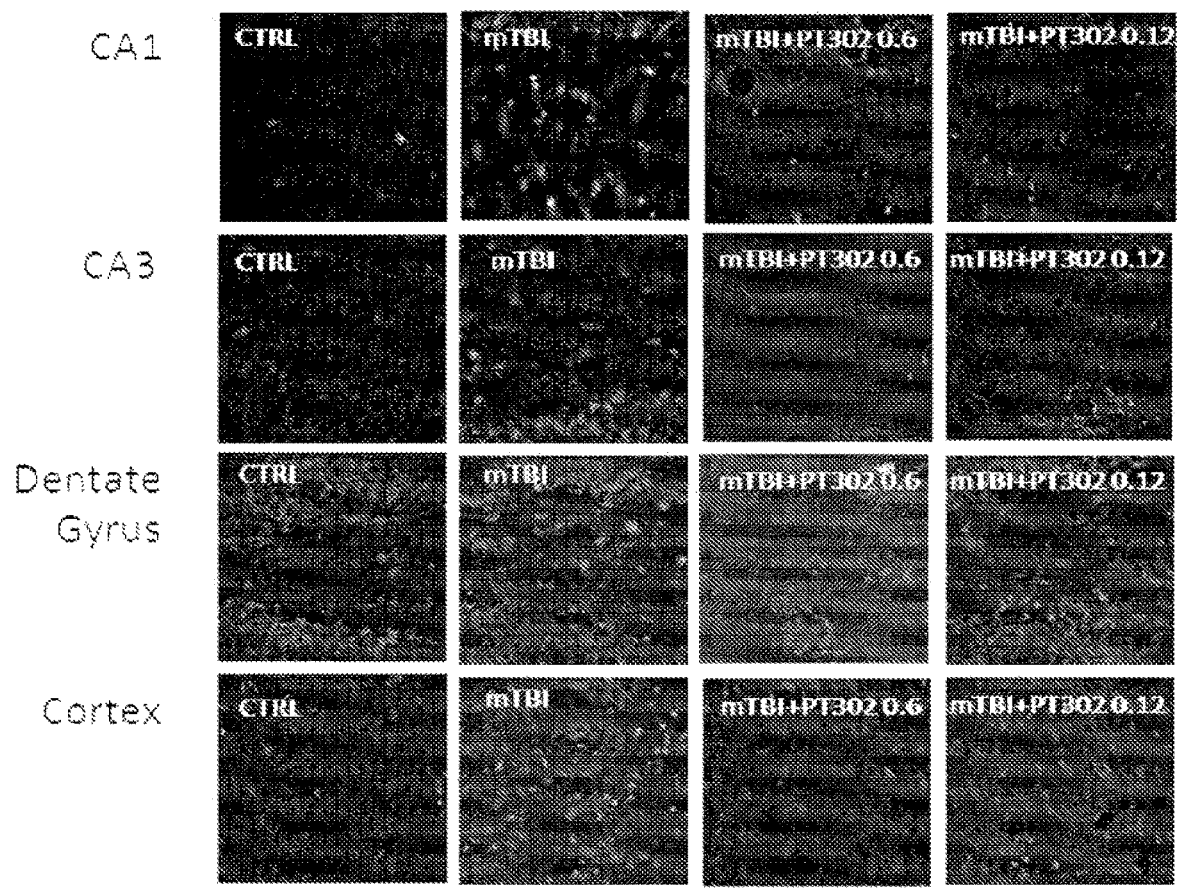
FIG. 14A. Representative images of Fluoro-Jade® C staining, as a marker of neuron loss due to brain injury, in control (CTRL) and mTBI-challenged mice provided vehicle or sustained-release Exenatide at 0.6 mg/kg or 0.12 mg/kg (PT302).
Figure 14B:
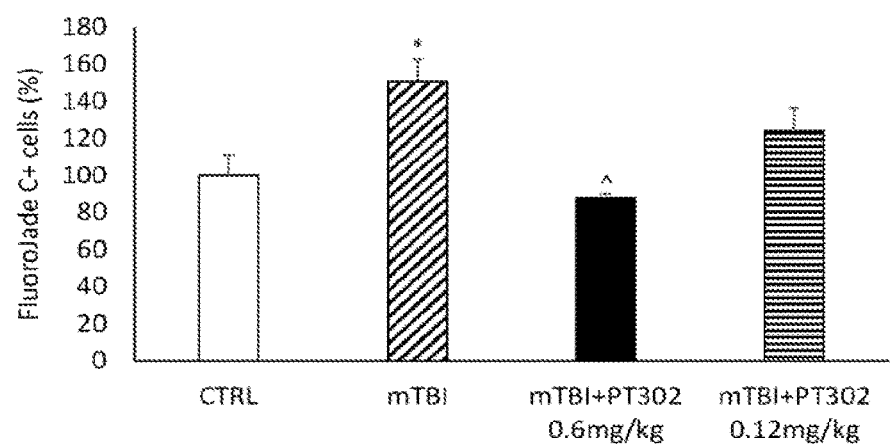
FIG. 14B. A graph illustrating the quantification of the hippocampal CA1 region data associated with the representative images of FIG. 14A and the strong increase in neuron loss due to traumatic brain injury in the CA1 of untreated mTBI-induced mice, which was significantly decreased with the administration of 0.6 mg/kg of sustained-release Exenatide (PT302).
Figure 14C:
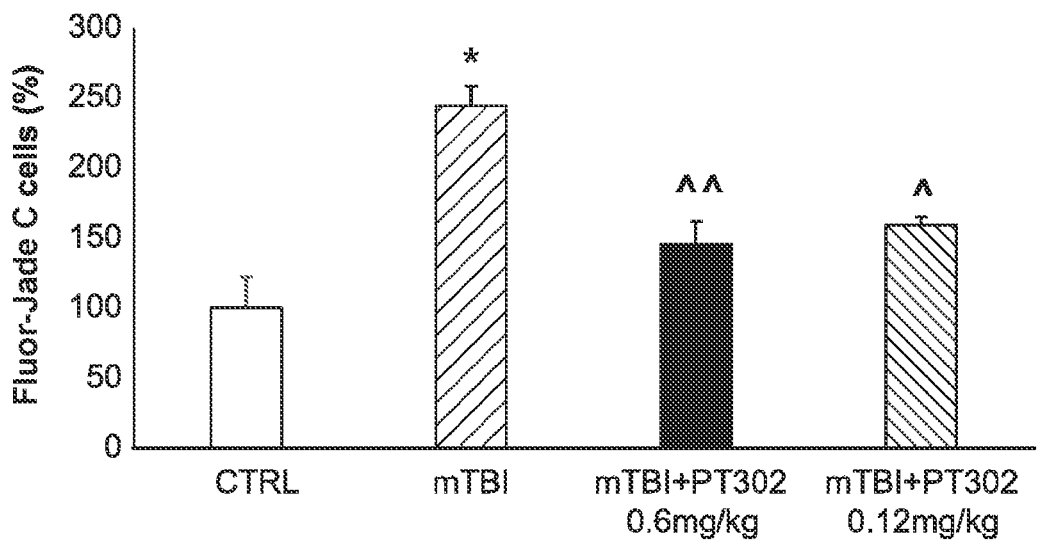
FIG. 14C. A graph illustrating the quantification of the hippocampal CA3 region data associated with the representative images of FIG. 14A and the strong increase in neuron loss due to traumatic brain injury in the CA3 of untreated mTBI-induced mice, which was significantly decreased with the administration of 0.6 mg/kg or 0.12 mg/kg of sustained-release Exenatide (PT302).
Figure 14D:
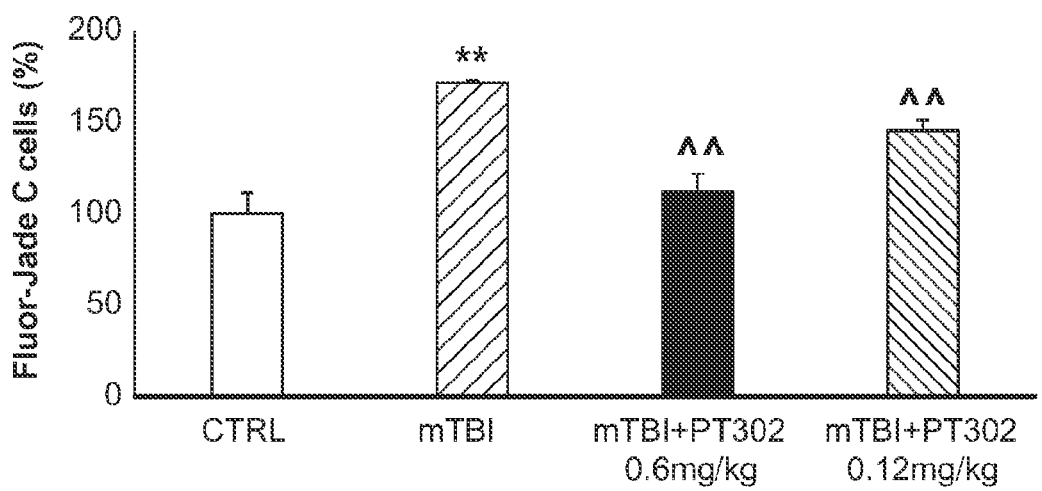
FIG. 14D. A graph illustrating the quantification of the dentate gyrus data associated with the representative images of FIG. 14A and the strong increase in neuron loss due to traumatic brain injury in the dentate gyrus of untreated mTBI-induced mice, which was significantly decreased with the administration of 0.6 mg/kg or 0.12 mg/kg of sustained-release Exenatide (PT302).
Figure 14E:
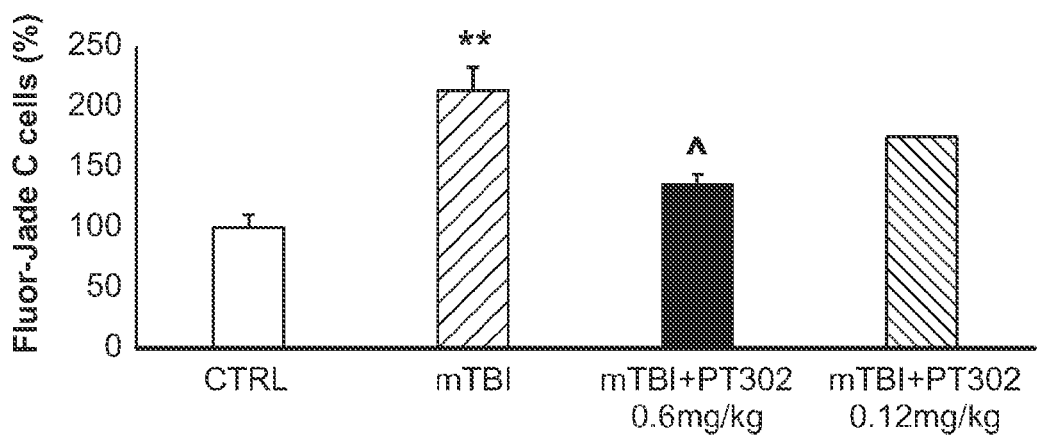
FIG. 14E. A graph illustrating the quantification of the cerebral cortex data associated with the representative images of FIG. 14A and the strong increase in neuron loss due to traumatic brain injury in the cortex of untreated mTBI-induced mice, which was significantly decreased with the administration of 0.6 mg/kg of sustained-release Exenatide (PT302).

As shown in FIG. 14A, after mTBI injury, a strong increase in the number of Fluoro-Jade C positive neurons was observed in all areas examined (CA1, CA3, DG for Hippocampus, and lateral cortex) as compared to controls ($p<0.05$ for CA1; $p<0.001$ for CA3, DG and CTX; FIG. 14A, and FIGS. 14B, 14C, and 14D, and 14E, respectively). Treatment with PT302 at the dose of 0.6 mg/kg counteracted mTBI-induced neurodegeneration in all the areas examined ($p<0.01$ in CA3 and DG, FIGS. 14C and 14D; $p<0.05$ in CTX and CA1, FIGS. 14E and 14B), while the PT302 dose of 0.12 mg/kg showed a significant effect in CA3 region ($p<0.05$).

Figure 15A:
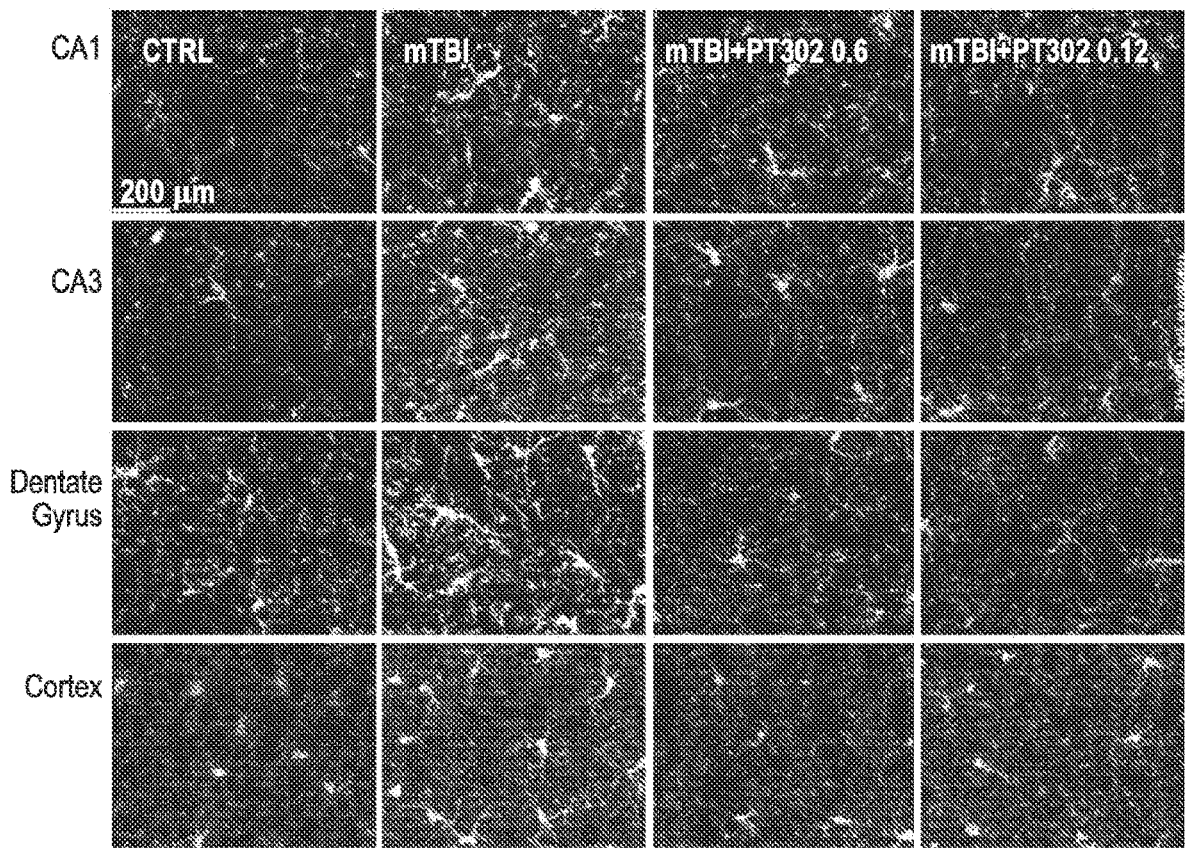
FIG. 15A. Representative images of Ionized calcium-binding adaptor molecule 1 (IBA1) staining, as a marker of microglia activation and neuroinflammation due to traumatic brain injury, in control and mTBI-induced mice provided vehicle or sustained-release Exenatide (PT302) at 0.6 mg/kg or 0.12 mg/kg.
Figure 15B:
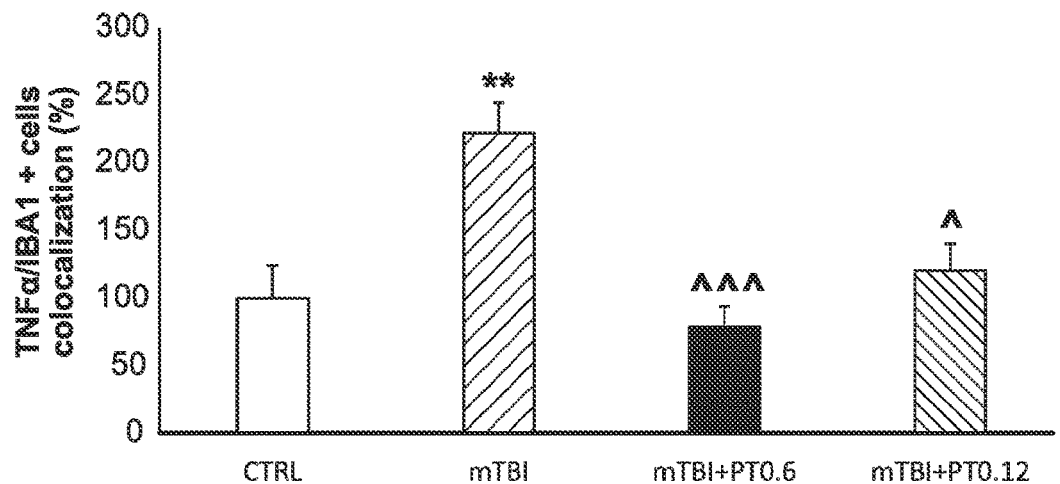
FIG. 15B. A graph illustrating the quantification of the CA1 data associated with the representative images of FIG. 15A and that pro-inflammatory cytokine TNF-α was significantly increased in IBA1+ cells in the CA1 of untreated mTBI-induced mice, which was significantly decreased with the administration of 0.6 mg/kg or 0.12 mg/kg of sustained-release Exenatide (PT302).
Figure 15C:
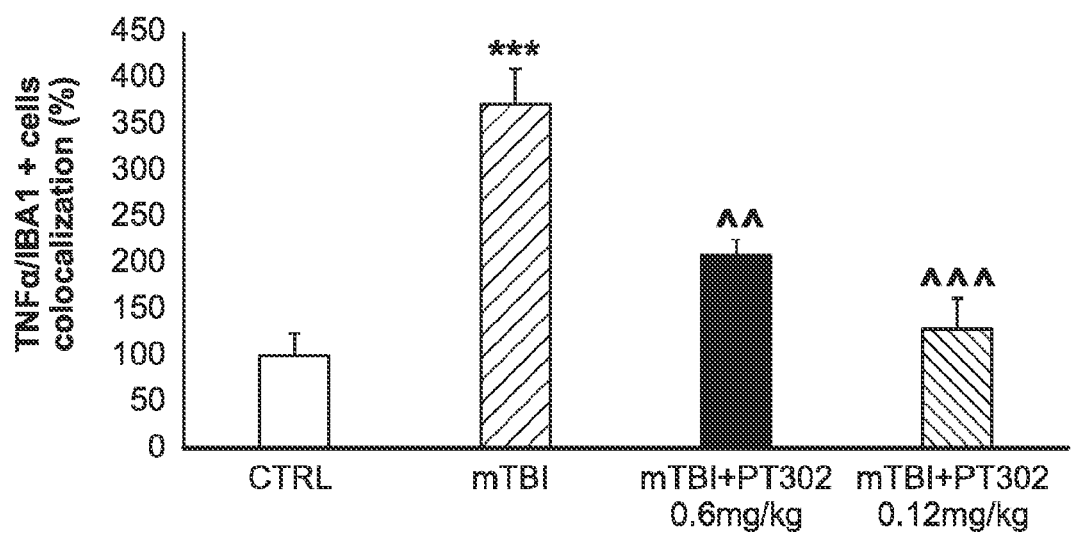
FIG. 15C. A graph illustrating the quantification of the CA3 data associated with the representative images of FIG. 15A and that pro-inflammatory cytokine TNF-α was significantly increased in IBA1+ cells in the CA3 of untreated mTBI-induced mice, which was significantly decreased with the administration of 0.6 mg/kg or 0.12 mg/kg of sustained-release Exenatide (PT302).
Figure 15D:
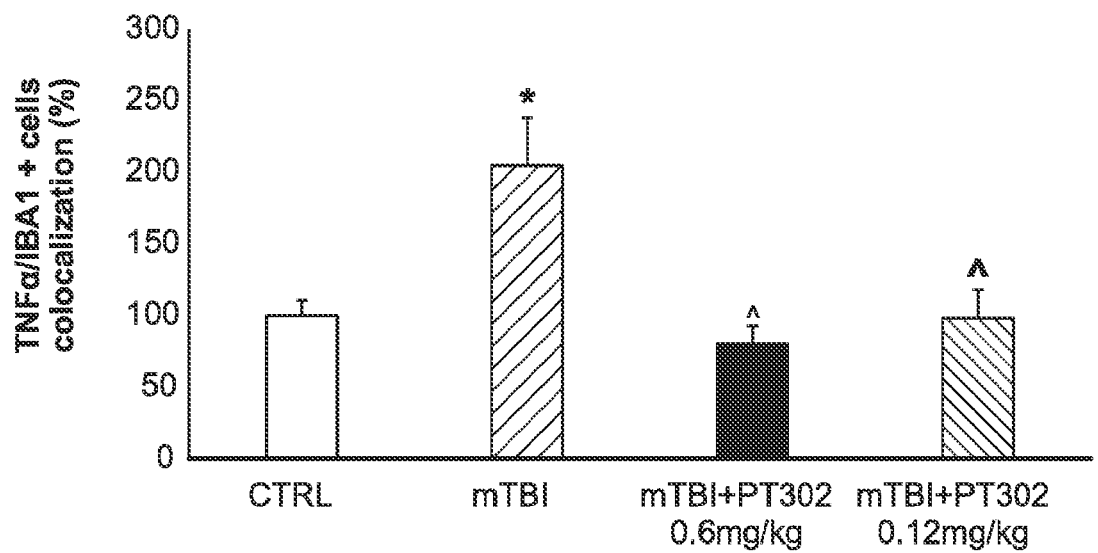
FIG. 15D. A graph illustrating the quantification of the dentate gyrus data associated with the representative images of FIG. 15A and that pro-inflammatory cytokine TNF-α was significantly increased in IBA1+ cells in the dentate gyrus of untreated mTBI-induced mice, which was significantly decreased with the administration of 0.6 mg/kg or 0.12 mg/kg of sustained-release Exenatide (PT302).
Figure 15E:
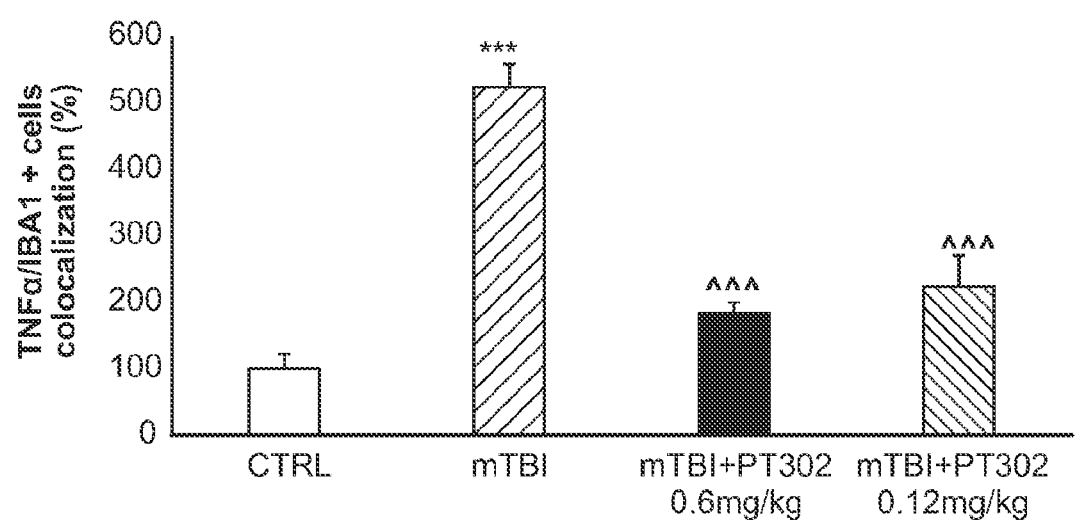
FIG. 15E. A graph illustrating the quantification of the cerebral cortex data associated with the representative images of FIG. 15A and that pro-inflammatory cytokine TNF-α was significantly increased in IBA1+ cells in the cortex of untreated mTBI-induced mice, which was significantly decreased with the administration of 0.6 mg/kg or 0.12 mg/kg of sustained-release Exenatide.

As shown in FIG. 15A, following mTBI injury, IBA1 immunoreactivity was increased as compared to vehicle control, in all the analyzed regions ($p<0.05$ for CA1; $p<0.001$ for CA3, DG and CTX). In the control group, microglial cells displayed a resting morphology with a small soma, long and thin processes (FIG. 15A). After mTBI injury microglia showed an activated morphology, characterized by a larger body with shorter and thicker processes (FIG. 15A). PT302 at both doses inhibited microglial activation: PT302 0.6 mg/kg resulted effective in all the brain regions ($p<0.001$ in CTX; $p<0.001$ in CA1 and CA3; $p<0.05$ in DG).

Immunoreactivity for the pro-inflammatory cytokine TNF-α increased in IBA1+ cells in mTBI-lesioned group in all the analyzed areas ($p<0.05$ in DG; $p<0.01$ in CA1; $p<0.001$ in CA3 and cortex; FIGS. 15D, 15B, 15C, and 15E, respectively). Administration of PT302 at the doses of 0.6 and 0.12 mg/kg reduced the levels of IBA1/TNF-α IR colocalization volume in both hippocampus and cortex.

Specific Embodiments

An aspect of the present disclosure provides a method for delivering a neuroprotective polypeptide to at least a portion of a central nervous system (CNS) of a subject. The method comprises: administering to the systemic blood circulation of the subject a therapeutically effective amount of neuroprotective polypeptide by a controlled-release formulation or a device providing a sustained release or delivery of the neuroprotective polypeptide, wherein the neuroprotective polypeptide includes at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof; and wherein the controlled-release neuroprotective formulation or sustained release of the neuroprotective polypeptide enhances the delivery and/or uptake of the neuroprotective polypeptide across a blood-brain barrier (BBB) of the subject to at least a portion of the central nervous system (CNS) relative to a rapid release formulation of the neuroprotective peptide.

Another aspect of the present disclosure provides a method of treating a subject with a central nervous system (CNS)-related disease or reducing at least one symptom of a CNS-related disease in a subject in need thereof. The method comprises: administering to the systemic blood circulation of the subject a therapeutically effective amount of a neuroprotective polypeptide by a controlled-release formulation or a device providing a sustained release or delivery of a neuroprotective polypeptide, wherein the neuroprotective polypeptide includes at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4 or a combination thereof; and wherein the controlled-release neuroprotective formulation or a device enhances the delivery of the neuroprotective polypeptide across a blood-brain barrier (BBB) of the subject to at least a portion of the central nervous system (CNS) relative to a rapid release formulation of the neuroprotective polypeptide.

An aspect of the present disclosure provides a method for delivering a neuroprotective polypeptide to at least a portion of a central nervous system (CNS) of a subject. The method comprising administering a controlled-release formulation to the systemic blood circulation of the subject including at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof, and the controlled-release neuroprotective formulation enhances the delivery and/or uptake of the neuroprotective polypeptide across a blood brain barrier (BBB) of the subject to at least a portion of the central nervous system (CNS) relative to a rapid release formulation of the neuroprotective polypeptide.

In any aspect or embodiment described herein, the controlled-release formulation is a long acting formulation of the neuroprotective polypeptide.

In any aspect or embodiment described herein, the controlled-release formulation further comprises a biodegradable polymer with a specific viscosity, and a coating material so that bioavailability and sustained release of an effective amount of the neuroprotective polypeptide is effectuated for a sufficient period (e.g., without an initial burst, such as a detrimental initial burst, of the active ingredient).

In any aspect or embodiment described herein, the controlled-release neuroprotective formulation comprises: a controlled-release microsphere that includes a core with the neuroprotective polypeptide and a biodegradable polymer; and a coating layer that coats the core.

In any aspect or embodiment described herein, the long acting formulation comprises a depot formulation for sustained release of the neuroprotective polypeptide.

In any aspect or embodiment described herein, the long acting formulation comprises a composition for sustained release of the neuroprotective polypeptide.

In any aspect or embodiment described herein, administering the controlled-release neuroprotective formulation alleviates at least one symptom of at least one CNS-related condition in the subject In any aspect or embodiment described herein, the CNS-related condition is selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy, motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

In any aspect or embodiment described herein, administering a controlled-release neuroprotective formulation comprises injecting the controlled-release neuroprotective formulation.

In any aspect or embodiment described herein, injecting the controlled-release neuroprotective formulation is a subcutaneous injection.

In any aspect or embodiment described herein, administering the controlled-release neuroprotective formulation results in a steady-state plasma concentration of the neuroprotective polypeptide that is in a range of about 50 to about 4500 pg/mL.

In any aspect or embodiment described herein, administering the controlled-release neuroprotective formulation results in a cumulative increase in the neuroprotective polypeptide concentration in the cerebrospinal fluid (CSF), the brain or a combination thereof in the subject.

In any aspect or embodiment described herein, the neuroprotective polypeptide concentration in the CSF is within the range of about 5 to about 400 pg/mL.

A further aspect of the present disclosure provides a method of treating a subject with a central nervous system (CNS)-related disease or reducing at least one symptom of a CNS-related disease in a subject in need thereof. The method comprising administering to the systemic blood circulation of the subject a therapeutically effective amount of a controlled-release neuroprotective formulation including at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4 or a combination thereof, and the controlled-release neuroprotective formulation enhances the delivery of the neuroprotective polypeptide across a blood brain barrier (BBB) of the subject to at least a portion of the central nervous system (CNS) relative to a rapid release formulation of the neuroprotective polypeptide.

In any aspect or embodiment described herein, the controlled-release formulation is a long acting formulation of the neuroprotective polypeptide.

In any aspect or embodiment described herein, the controlled-release formulation further comprises a biodegradable polymer with a specific viscosity and coating materials, having bioavailability and sustained release of the neuroprotective polypeptide in an effective concentration for a certain period (e.g., without an initial burst, such as a detrimental initial burst, of the active ingredient).

In any aspect or embodiment described herein, the controlled-release neuroprotective formulation comprises: a controlled-release microsphere that includes a core with the neuroprotective polypeptide and a biodegradable polymer; and a coating layer that coats the core.

In any aspect or embodiment described herein, the long acting formulation comprises a depot formulation for sustained release of the neuroprotective polypeptide.

In any aspect or embodiment described herein, the long acting formulation comprises a composition for sustained release of the neuroprotective polypeptide.

In any aspect or embodiment described herein, administering the controlled-release neuroprotective formulation alleviates at least one symptom of at least one CNS-related condition in the subject.

In any aspect or embodiment described herein, the CNS-related condition is selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy, motor neuron diseases (e.g., amyotrophic lateral sclerosis, spinal cord injury, spinocerebellar ataxia (SCA), spinal muscular atrophy (SMA)), vascular dementia, dementia with Lewy bodies (DLB), mixed dementia, frontotemporal dementia, Creutzfeldt-Jakob disease, normal pressure hydrocephalus, or a combination thereof.

In any aspect or embodiment described herein, administering the controlled-release neuroprotective formulation comprises injecting the controlled-release neuroprotective formulation to the subject.

In any aspect or embodiment described herein, injecting the controlled-release neuroprotective formulation to the subject is a subcutaneous injection.

In any aspect or embodiment described herein, administering the controlled-release formulation results in a steady-state plasma concentration of the neuroprotective polypeptide that is in a range of about 50 to about 4500 pg/mL.

In any aspect or embodiment described herein, administering the controlled-release formulation results in a cumulative increase in the neuroprotective polypeptide concentration in at least one of the cerebrospinal fluid (CSF), the brain, or a combination thereof.

In any aspect or embodiment described herein, the formulation is administered once every 7 to 21 days (e.g., once every 7, 8, 9, 10, 11, 12, 13, 14, 15, 16, 17, 18, 19, 20, or 21 days).

In any aspect or embodiment described herein, the formulation is administered a second time about 7 to about 21 days (e.g., once every about 7, about 8, about 9, about 10, about 11, about 12, about 13, about 14, about 15, about 16, about 17, about 18, about 19, about 20, or about 21 days) after the previous administration.

In any aspect or embodiment described herein, the percent change in the neuroprotective polypeptide concentration in the plasma is no greater than about 30% when the formulation is re-administered within about 28 days (e.g., within about 21 or about 14 days) of a previous formulation administration.

An additional aspect of the disclosure provides a method for delivering a neuroprotective polypeptide to at least a portion of a central nervous system (CNS) of a subject. The method comprises: providing a sustained delivery to the systemic blood circulation of the subject at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof; and wherein the controlled-release neuroprotective formulation enhances the delivery and/or uptake of the neuroprotective polypeptide across a blood brain barrier (BBB) of the subject to at least a portion of the central nervous system (CNS) relative to a rapid release formulation of the neuroprotective peptide.

An further aspect of the disclosure provides a method of treating a subject with a central nervous system (CNS)-related disease or reducing at least one symptom of a CNS-related disease in a subject in need thereof. The method comprises: providing a sustained delivery to the systemic blood circulation of the subject at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4 or a combination thereof; and wherein the controlled-release neuroprotective formulation enhances the delivery of the neuroprotective polypeptide across a blood brain barrier (BBB) of the subject to at least a portion of the central nervous system (CNS) relative to a rapid release formulation of the neuroprotective polypeptide.

In any aspect or embodiment described herein, providing the sustained release neuroprotective polypeptide or polypeptides administering the neuroprotective polypeptide or polypeptides via a device (e.g., a pump, a mini-pump, an osmotic pump, an osmotic delivery device, an infusion pump, an intravenous administration device, a peristaltic pump, a miniature infusion pump, or the like).

In any aspect or embodiment described herein, the percent change in the steady-state neuroprotective polypeptide concentration in the plasma after steady-state is achieved is no greater than about 80% (e.g., no greater than about 50% or no greater than about 40%) when the formulation is administered (e.g., when administered once every 7 to 28 days, or once every 7, 8, 9, 10, 11, 12, 13, 14, 15, 16, 17, 18, 19, 20, 21, 22, 23, 24, 25, 26, 27, or 28 days).

In any aspect or embodiment described herein, the neuroprotective polypeptide or polypeptides is administered via a device (e.g., a pump, a mini-pump, an osmotic pump, an osmotic delivery device, an infusion pump, an intravenous administration device, a peristaltic pump, a miniature infusion pump, or the like).

In any aspect or embodiment described herein, the neuroprotective polypeptide or polypeptides is administered at a rate of about 1 pM/kg/min to about 30 pM/kg/min (e.g., about 3 pM/kg/min to about 17.5 pM/kg/min).

In any aspect or embodiment described herein, administering the controlled-release neuroprotective formulation or providing a sustained delivery of the neuroprotective polypeptide alleviates at least one symptom of at least one CNS-related condition in the subject.

In any aspect or embodiment described herein, administering the controlled-release formulation or providing the sustained release of the neuroprotective polypeptide results in a steady-state plasma concentration of the neuroprotective polypeptide that is in a range of about 50 to about 4500 pg/mL.

In any aspect or embodiment described herein, administering the controlled-release formulation or providing the sustained release of the neuroprotective polypeptide results in a cumulative increase in the neuroprotective polypeptide concentration in at least one of the cerebrospinal fluid (CSF), the brain, or a combination thereof.

In any aspect or embodiment described herein, the neuroprotective polypeptide concentration in the CSF is within the range of about 10 to about 400 pg/mL.

In any aspect or embodiment described herein, the ratio of the steady-state polypeptide concentration in the CFS to the plasma is in the range of about 0.1% to about 5%.

In any aspect or embodiment described herein, the exendin-4 analogue is represented by Chemical Formula I or its pharmaceutically acceptable salt:

Xaa1 Xaa2 Xaa3 Xaa4 Xaa5 Xaa6 Xaa7 Xaa8 Xaa9
Xaa10 Xaa11 Xaa12 Xaa13 Xaa14 Xaa15
Xaa16 Xaa17 Ala Xaa19 Xaa20 Xaa21 Xaa22
Xaa23 Xaa24 Xaa25 Xaa26
Xaa27 Xaa28-$Z_1$, (Chemical Formula I)

wherein:
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;

Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala, or Arg;
Xaa21 is Ala, Leu, or Lys-NHε-R, wherein R is Lys, Arg, or a C1-C10 straight chain or branched alkanoyl;
Xaa22 is Ala, Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
Xaa27 is Ala or Lys;
Xaa28 is Ala or Asn; and $Z_1$ is —OH, —NH$_2$, Gly-$Z_2$, Gly Gly-$Z_2$, Gly Gly Xaa31-$Z_2$, Gly Gly Xaa31 Ser-$Z_2$, Gly Gly Xaa31 Ser Ser-$Z_2$, Gly Gly Xaa31 Ser Ser Gly-$Z_2$, Gly Gly Xaa31 Ser Ser Gly Ala-$Z_2$, Gly Gly Xaa31 Ser Ser Gly Ala Xaa36-$Z_2$, Gly Gly Xaa31 Ser Ser Gly Ala Xaa36 Xaa37-$Z_2$, Gly Gly Xaa31 Ser Ser Gly Ala Xaa36 Xaa37 Xaa38-$Z_2$, or Gly Gly Xaa31 Ser Ser Gly Ala Xaa36 Xaa37 Xaa38 Xaa39-$Z_2$, Xaa31, Xaa36, Xaa37, and Xaa38 are independently selected from the group consisting of Pro, homoproline, 3Hyp, 4Hyp, thioproline, N-alkylglycine, N-alkylpentylglycine, or N-alkylalanine, Xaa39 is Ser, or Tyr (e.g. Ser), and $Z_2$ is —OH, or —NH$_2$, provided that:
no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, Xaa26, Xaa27, and Xaa28 are Ala; and
when Xaa1 is His, Arg, or Tyr, at least one of Xaa3, Xaa4, and Xaa9 is Ala.

In any aspect or embodiment described herein, the exendin-4 analogue is represented by Chemical Formula II or their pharmaceutically acceptable salts:

Xaa1 Xaa2 Xaa3 Xaa4 Xaa5 Xaa6 Xaa7 Xaa8 Xaa9
Xaa10 Xaa11 Xaa12 Xaa13 Xaa14 Xaa15
Xaa16 Xaa17 Ala Xaa19 Xaa20 Xaa21 Xaa22
Xaa23 Xaa24 Xaa25 Xaa26 X$_1$-Z$_1$,     (Chemical Formula II)

wherein:
Xaa1 is His, Arg, Tyr, Ala, Norval, Val, Norleu, or 4-imidazopropionyl;
Xaa2 is Ser, Gly, Ala, or Thr;
Xaa3 is Ala, Asp, or Glu;
Xaa4 is Ala, Norval, Val, Norleu, or Gly;
Xaa5 is Ala or Thr;
Xaa6 is Ala, Phe, Tyr, or naphthylalanine;
Xaa7 is Thr or Ser;
Xaa8 is Ala, Ser, or Thr;
Xaa9 is Ala, Norval, Val, Norleu, Asp, or Glu;
Xaa10 is Ala, Leu, Ile, Val, pentylglycine, or Met;
Xaa11 is Ala or Ser;
Xaa12 is Ala or Lys;
Xaa13 is Ala or Gln;
Xaa14 is Ala, Leu, Ile, pentylglycine, Val, or Met;
Xaa15 is Ala or Glu;
Xaa16 is Ala or Glu;
Xaa17 is Ala or Glu;
Xaa19 is Ala or Val;
Xaa20 is Ala or Arg;
Xaa21 is Ala, Leu, or Lys-NHε-R, wherein R is Lys, Arg, C1-C10 straight chain or branched alkanoyl, or cycloalleylalkanoyl;
Xaa22 is Phe, Tyr, or naphthylalanine;
Xaa23 is Ile, Val, Leu, pentylglycine, tert-butylglycine, or Met;
Xaa24 is Ala, Glu, or Asp;
Xaa25 is Ala, Trp, Phe, Tyr, or naphthylalanine;
Xaa26 is Ala or Leu;
X1 is Lys Asn, Asn Lys, Lys-NHε-R Asn, Asn Lys-NHε-R, Lys-NHε-R Ala, Ala Lys-NHε-R, wherein R is Lys, Arg, a C1-C10 straight chain or branched alkanoyl, or cycloalkylalkanoyl;

$Z_1$ is —OH, —NH$_2$, Gly-$Z_2$, Gly Gly-$Z_2$, Gly Gly Xaa31-$Z_2$, Gly Gly Xaa31 Ser-$Z_2$, Gly Gly Xaa31 Ser Ser-$Z_2$, Gly Gly Xaa31 Ser Ser Gly-$Z_2$, Gly Gly Xaa31 Ser Ser Gly Ala-$Z_2$, Gly Gly Xaa31 Ser Ser Gly Ala Xaa36-$Z_2$, Gly Gly Xaa31 Ser Ser Gly Ala Xaa36 Xaa37-$Z_2$, Gly Gly Xaa31 Ser Ser Gly Ala Xaa36 Xaa37 Xaa38-$Z_2$, or Gly Gly Xaa31 Ser Ser Gly Ala Xaa36 Xaa37 Xaa38 Xaa39-$Z_2$;

Xaa31, Xaa36, Xaa37, and Xaa38 are independently selected from the group consisting of Pro, homoproline, 3Hyp, 4Hyp, thioproline, N-alkylglycine, N-alkylpentylglycine, and N-alkylalanine, Xaa39 is Ser or Tyr; and
$Z_2$ is —OH or —NH$_2$, provided that:
no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala; and
when Xaa1 is His, Arg, Tyr, or 4-imidazopropionyl, at least one of Xaa3, Xaa4, and Xaa9 is Ala.

In any aspect or embodiment described herein, the neuroprotective polypeptide is selected from the group consisting of SEQ ID NOS: 1-55.

Each documents referred to herein is incorporated herein by reference. Except in the Examples, or where otherwise explicitly indicated, all numerical quantities in this description specifying amounts of materials, and the like, are to be understood as modified by the word "about". It is to be understood that the upper and lower amount, range, and ratio limits set forth herein may be independently combined. Similarly, the ranges and amounts for each element of the disclosure can be used together with ranges or amounts for any of the other elements.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

REFERENCES

Abercrombie M (1946) Estimation of nuclear population from microtome sections. *Anat Rec* 94:239-247.

Bressler et al. "Pharmacological regulation of blood glucose levels in non-insulin dependent diabetes," *Arch. Int. Med.* 157:836-848 (1997).

Calvo et al. "Structural characterization by affinity cross-linking of glucagon-like peptide-1 (7-36) amide receptor in rat brain," *J. Neurochem.* 64(1):299-306 (1995)

Campos et al. "Divergent tissue-specific and developmental expression of receptors for glucagon and glucagon-like peptide-1 in the mouse," *Endocrinology* 134:2156-64 (1994)

Chen et al. "Tissue-specific expression of unique mRNAs that encode pro-glucagon-derived peptides or exendin-4 in the lizard," *J. Biol. Chem.* 272: 4108-4115 (1997)

De Ore et al. "The effect of GLP-1 on insulin release in young and old rats in the fasting state and during an intravenous glucose tolerance test," *J. Gerontol.* 52:B245-249 (1997)

Drucker et al. "Glucagon-like peptide I stimulates insulin gene expression and increases cyclic AMP levels in a rat islet cell line," *Proc. Natl. Acad. Sci.* 84:3434-3438 (1987)

During M J, et al. "Glucagon-like peptide-1 receptor is involved in learning and neuroprotection," *Nature Medicine* 9: 1173-1179 (2003).

Elahi et al. "The insulinotropic actions of glucose-dependent insulinotropic polypeptide (GIP) and glucagon-like peptide-1 (7-36) in normal and diabetic subjects," *Regul. Pep.* 51:63-74 (1994)

Fehmann et al. "Cell and Molecular Biology of the Incretin Hormones Glucagon-Like Peptide-I and Glucose-Dependent Insulin Releasing Polypeptide," *Endocrine Rev.* 16:390-410 (1995)

Fehmann et al. "Insulinotropic hormone glucagon-like peptide-1 (7-37) stimulation of proinsulin gene expression and proinsulin biosynthesis in insulinoma BTC-1 cells", *Endocrinology* 130: 159-166 (1992)

Geula and Mesulam "Cortical cholinergic fibers in aging and Alzheimer's disease: a morphometric study," *Neuroscience.* 33:469-81 (1989)

Ghazzi et al. "Cardiac and glycemic benefits of troglitazone treatment in NIDDM," *Diabetes* 46: 433-439. Care. 15: 270-276 (1997)

Goke et al. "Cardiac and Glycemic Benefits of Troglitazone Treatment in NIDDM," *Diabetes* 46:433-439 (1993)

Goke et al. "Distribution of GLP-1 binding sites in the rat brain: evidence that exendin-4 is a ligand of brain GLP-1 binding sites, *Eur. J. Neurosci* 7:2294-2300 (1995)

Goke et al. "Exendin-4 is a high potency agonist and truncated exendin-4 (9-39)-amide in an antagonist at the GLP-1 (7-36)-amide receptor of insulin-secreting-cells," *J. Biol. Chem.* 268:19650-19655 (1993)

Greig N et al. "Once daily injection of exendin-4 to diabetic mice achieves long-term beneficial effects on blood glucose concentrations." *Diabetologia* 42:45-50, (1999).

Gross and Meienhofer (eds.) "The Peptides: Analysis, Synthesis," Biology 3: Protection of Functional Groups in *Peptide Synthesis*, Academic Press, N.Y. (1981)

Gutniak et al. "Antidiabetogenic effect of glucagon-like peptide-1 (7-36) amide in normal subjects and patients with diabetes mellitus," *N. Engl. J. Med.* 326:1316-1322 (1992)

Jia Y et al. 2015 Peptidic exenatide and herbal catapol mediate neuroprotection via the hippocampal GLP-1 receptor/β-endorphin pathway," *Pharmacological Research* 102:276-85.

Jin et al. "Distribution of glucagonlike peptide I (GLP-I), glucagon, and glicentin in the rat brain: an immunocytochemical study," *J. Comp. Neurol.* 271:519-32. (1988)

Kastin A J and Akeerstrom V, International Journal of Obesity (2003) 27, 313-31

Kim B J, et al. "Transferrin fusion technology: a novel approach to prolonging biological half-life of insulinotropic peptides," *J Pharmacol Exp. Ther.* 2010 Sep. 1; 334(3):682-92.

Kim S, et al. "Exendin-4 protects dopaminergic neurons by inhibition of microglial activation and matrix metalloproteinase-3 expression in an animal model of Parkinson's disease," J Endocrinol 202(3):431-9 (2009)

Lahiri D K, Farlow M R, Hintz N, Utsuki T and Greig N H. 2000 Cholinesterase inhibitors, beta-amyloid precursor protein and amyloid beta-peptides in Alzheimer's disease *Acta Neurol Scand Suppl* 176:60-67.

Li Y, et al. "GLP-1 receptor stimulation preserves primary cortical and dopaminergic neurons in cellular and rodent models of stroke and Parkinsonism," *Proc Natl Acad Sci USA* 106(4): 1285-90 (2009)

Liu W, et al. "Neuroprotective effects of lixisenatide and liraglutide in the 1-methyl-4-phenyl-1,2,3,6-tetrahydropyridine mouse model of Parkinson's disease," *Neuroscience* 202:42-50 (2015)

Lu Z, et al., 2014 "Differential hypoglycaemic, anorectic, autonomic and emetic effects of the glucagon-like peptide receptor agonist, exendin-4, in the conscious telemetered ferret," *J. Transl Med.* 12: 327.

Mark R J, Pang Z, Geddes J W, Uchida K and Mattson M P. 1997 Amyloid beta-peptide impairs glucose transport in hippocampal and cortical neurons: involvement of membrane lipid peroxidation *J Neurosci* 17.1046-1054.

Martin B, et al. 2012 "Euglycemic agent-mediated hypothalamic transcriptomic manipulation in the N171-82Q model of Huntington disease is related to their physiological efficacy," *J Biol Chem* 287(38):31766-82.

Mattson M P, Lovell M A, Furukawa K et al., (1995) Neurotrophic factors attenuate glutamate-induced accumulation of peroxides, elevation of intracellular Ca2+ concentration, and neurotoxicity and increase antioxidant enzyme activities in hippocampal neurons. *J Neurochem* 65(4):1740-1751.

Moceri et al. "Early-life risk factors and the development of Alzheimer's disease," *Neurology* 54:415-420 (2000)

Montrose-Rafizadeh C, Wang Y, Janczewski A M et al., (1997a) Overexpression of glucagon-like peptide-1 receptor in an insulin-secreting cell line enhances glucose responsiveness. *Mol Cell Endocrinol* 130(1-2):109-117.

Montrose-Rafizadeh et al. "High potency antagonists of the pancreatic glucagon-like peptide-1 receptor," *J. Biol. Chem.* 272:21201-21206 (1997b)

Montrose-Rafizadeh et al. "Incretin hormones regulate glucose dependent insulin secretion in RIN 1046-38 cells: mechanisms of action," *Endocrinology* 135:589-594 (1994)

Nathan et al. "Insulinotropic action of glucagonlike peptide-I-(7-37) in diabetic and nondiabetic subjects," *Diabetes Care* 15:270-276 (1992)

Nauck et al. "Preserved incretin activity of Glucagon-like peptide 1 (7-36) amide but not of synthetic human gastric inhibitory polypeptide in patients with Type-2 diabetes mellitus," *J. Clin. Invest.* 91: 301-307 (1993)

Nauck et al. "Normalization of fasting hyperglycemia by exogenous glucagon-like peptide-1 (7-36) amide in type II (non-insulin dependent) diabetic patients," *Diabetologia* 36:741-744 (1993)

Naya et al. "Diabetes, defective pancreatic morphogenesis, and abnormal enteroendocrine differentiation in BETA2/neuroD-deficient mice," *Genes Dev.* 11:2323-2334 (1997)

Orskov "Glucagon-like peptide-1, a new hormone of the entero-insular axis," *Diabetologia* 35: 701-711 (1992)

Ott et al. "Diabetes mellitus and the risk of dementia: The Rotterdam Study," *Neurology* 53:1937-42 (1999)

Paxinos and Watson. "The rat brain in stereotaxic coordinates", Academic Press, NSW Australia (1998).

Perry et al. "Behavioural, histological and immunocytochemical consequences following 192 IgG-saporin immunolesions of the basal forebrain cholinergic system," *Brain Res. Bull.* 54:29-48 (2001)

*Remington's Pharmaceutical Sciences* (Martin, E. W. (ed.) latest edition Mack Publishing Co., Easton, Pa.)

Ritzel et al. "Pharmacokinetic, insulinotropic, and glucagonostatic properties of GLP-1 [7-36 amide] after subcutaneous injection in healthy volunteers. Dose-response-relationships," *Diabetologia*. 38:720-725 (1995)

Sambrook et al., *Molecular Cloning, a Laboratory Manual*, (2nd ed.) Vol. 1-3 Cold Spring Harbor Laboratory Press, NY (1989)

Satoh et al. "Characterization of human and rat glucagon-like peptide-1 receptors in the neurointermediate lobe: lack of coupling to either stimulation or inhibition of adenylyl cyclase," *Endocrinology* 141:1301-9 (2000)

Shughrue et al. "Glucagon-like peptide-1 receptor (GLP1-R) mRNA in the rat hypothalamus," *Endocrin.* 137(11): 5159-62 (1996)

Suzuki N, Cheung T T, Cai X D, Odaka A, Otvos L, Jr, Eckman C, Golde T E and Younkin S G. 1994 An increased percentage of long amyloid beta protein secreted by familial amyloid beta protein precursor (beta APP717) mutants *Science* 264:1336-1340.

Thorens et al. "Cloning and functional expression of the human islet GLP-1 receptor. Demonstration that exendin-4 is an agonist and exendin(9-39) an antagonist of the receptor," *Diabetes* 42:1678-1682 (1993)

Thorens et al. "Glucagon-like peptide-1 and the control of insulin secretion in the normal state and in NIDDM," *Diabetes* 42:1219-1225 (1993)

U.S. Pat. No. 3,710,795 "Drug-Delivery device with Stretched, Rate-Controlling Membrane," Higuchi et al. (Jan. 16, 1973)

Wang et al. "GIP regulates glucose transporters, hexokinases, and glucose-induced insulin secretion in RIN 1046-38 cells," *Moll. Cell. Endo.* 116:81-87 (1996)

Wang et al. "Glucagon-like peptide-1 affects gene transcription and messenger ribonucleic acid stability of components of the insulin secretory system in RIN 1046-38 cells," *Endocrinology* 136:4910-4917 (1995)

Wei et al. "Tissue-specific expression of the human receptor for glucagon-like peptide-I: brain, heart and pancreatic forms have the same deduced amino acid sequences," *FEBS Lett* 358(3):219-224 (Jan. 30, 1995)

Wilms et al. "Gastric emptying, glucose responses, and insulin secretion after a liquid test meal: effects of exogenous glucagon-like peptide-1 (7-36) amide in Type II (non-insulin-dependent) diabetic patients," *J. Clin. Edocrinol. Metab.* 81:327332 (1996)

What is claimed is:

1. A method for delivering a neuroprotective polypeptide to at least a portion of a central nervous system (CNS) of a subject, the method comprising:

administering to the systemic blood circulation of the subject a therapeutically effective amount of the neuroprotective polypeptide by a controlled-release formulation or by a device providing a sustained release of the neuroprotective polypeptide, wherein the neuroprotective polypeptide includes at least one neuroprotective polypeptide selected from the group consisting of GLP-1, exendin-4, or a therapeutically effective GLP-1 or exendin-4 analogue, wherein the neuroprotective polypeptide binds to and activates a receptor that binds at least one of GLP-1, exendin-4, or a combination thereof; and wherein the controlled-release neuroprotective formulation or sustained release of the neuroprotective polypeptide enhances the delivery and/or uptake of the neuroprotective polypeptide across a blood-brain barrier (BBB) of the subject to at least a portion of the central nervous system (CNS) relative to a rapid release formulation of the neuroprotective peptide.

2. The method according to claim 1, wherein the controlled-release formulation is a long acting formulation of the neuroprotective polypeptide.

3. The method according to claim 1, wherein the controlled-release formulation further comprises a biodegradable polymer with a specific viscosity, and a coating material.

4. The method of according to claim 1, wherein the controlled-release neuroprotective formulation comprises:
a controlled-release microsphere that includes a core with the neuroprotective polypeptide and a biodegradable polymer; and
a coating layer that coats the core.

5. The method according to claim 2, wherein the long acting formulation comprises a depot formulation for sustained release of the neuroprotective polypeptide.

6. The method according to claim 2, wherein the long acting formulation comprises a composition for sustained release of the neuroprotective polypeptide.

7. A method of treating a subject with a central nervous system (CNS)-related disease or reducing at least one symptom of a CNS-related disease in a subject in need thereof, the method comprising:
administering to the systemic blood circulation of the subject a therapeutically effective amount of a neuroprotective polypeptide by a controlled-release formulation or by a device providing a sustained release of the neuroprotective polypeptide, wherein the neuroprotective polypeptide includes at least one neuroprotective polypeptide selected from the group consisting of GLP-1, exendin-4, or a therapeutically effective GLP-1 or exendin-4 analogue,
wherein the neuroprotective polypeptide binds to and activates a receptor that binds at least one of GLP-1, exendin-4 or a combination thereof; and
wherein the controlled-release neuroprotective formulation or the sustained release of the neuroprotective polypeptide enhances the delivery of the neuroprotective polypeptide across a blood-brain barrier (BBB) of the subject to at least a portion of the central nervous system (CNS) relative to a rapid release formulation of the neuroprotective polypeptide.

8. The method according to claim 7, wherein the controlled-release formulation is a long acting formulation of the neuroprotective polypeptide.

9. The method according to claim 7, wherein the controlled-release formulation further comprises a biodegradable polymer with a specific viscosity and coating materials.

10. The method according to claim 7, wherein the controlled-release neuroprotective formulation comprises:
a controlled-release microsphere that includes a core with the neuroprotective polypeptide and a biodegradable polymer; and
a coating layer that coats the core.

11. The method according to claim 8, wherein the long acting formulation comprises a depot formulation for sustained release of the neuroprotective polypeptide.

12. The method according to claim 8, wherein the long acting formulation comprises a composition for sustained release of the neuroprotective polypeptide.

13. The method according to claim 3, wherein the biodegradable polymer is selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate, a copolymer or a simple mixture of two or more selected from the polymer group, a copolymer of a polymer selected from the polymer group and polyethyleneglycol (PEG), or a polymer-sugar complex where a sugar is coupled with a polymer selected from the polymer group or a copolymer comprising a polymer of the polymer group.

14. The method according to claim 1, wherein administering the controlled-release neuroprotective formulation comprises injecting the controlled-release neuroprotective formulation to the subject.

15. The method according to claim 14, wherein injecting the controlled-release formulation to the subject is a subcutaneous injection.

16. The method according to claim 1, wherein the controlled-release formulation is administered a subsequent time about 7 to about 21 days after the previous administration.

17. The method according to claim 1, wherein the device provides the sustained release of the controlled-release formulation.

18. The method of claim 1, wherein the device is a pump; wherein the pump is selected from the group consisting of a mini-pump, an osmotic pump, an infusion pump, a peristaltic pump, and a miniature infusion pump.

19. The method of claim 1, wherein the neuroprotective polypeptide is administered by the device at a rate of about 1 pM/kg/min to about 30 pM/kg/min.

20. The method according to claim 1, wherein administering the neuroprotective polypeptide to the systemic blood circulation alleviates at least one symptom of at least one CNS-related condition in the subject.

21. The method according to claim 20, wherein the CNS-related condition is selected from the group consisting of Parkinson's disease (PD), traumatic brain injury (TBI), multiple sclerosis, drug addiction, alcohol addiction, neurodegenerative conditions, inflammation of a brain, Alzheimer's disease (AD), multiple system atrophy, Huntington's disease, chronic traumatic encephalopathy (CTE), motor neuron diseases, amyotrophic lateral sclerosis, spinal cord injury, spinocerebellar ataxia (SCA), spinal muscular atrophy (SMA), vascular dementia, dementia with Lewy bodies (DLB), mixed dementia, frontotemporal dementia, Creutzfeldt-Jakob disease, normal pressure hydrocephalus, or a combination thereof.

22. The method according to claim 1, wherein administering the controlled-release formulation or providing the sustained release of the neuroprotective polypeptide by a device results in a steady-state plasma concentration of the neuroprotective polypeptide that is in a range of about 50 to about 4500 pg/mL.

23. The method according to claim 1, wherein administering the controlled-release formulation or providing the sustained release of the neuroprotective polypeptide by a device results in a cumulative increase of the neuroprotective polypeptide concentration in at least one of the cerebrospinal fluid (CSF), the brain, or a combination thereof.

24. The method according to claim 1, wherein the neuroprotective polypeptide concentration in the CSF is within the range of about 10 to about 400 pg/mL.

25. The method according to claim 1, wherein the ratio of the steady-state polypeptide concentration in the CSF to the plasma is in the range of about 0.1% to about 5%.

26. The method of according to claim 1, wherein the exendin-4 analogue is represented by Chemical Formula I or its pharmaceutically acceptable salt:

Xaa1 Xaa2 Xaa3 Xaa4 Xaa5 Xaa6 Xaa7 Xaa8 Xaa9
Xaa10 Xaa11 Xaa12 Xaa13 Xaa14 Xaa15
Xaa16 Xaa17 Ala Xaa19 Xaa20 Xaa21 Xaa22
Xaa23 Xaa24 Xaa25 Xaa26 Xaa27
Xaa28-$Z_1$,    (Chemical Formula I)

wherein:
  Xaa1 is His, Arg, Tyr, Ala, Norval, Val, Norleu, or 4-imidazopropionyl;
  Xaa2 is Ser, Gly, Ala, or Thr;
  Xaa3 is Ala, Asp, or Glu;
  Xaa4 is Ala, Norval, Val, Norleu, or Gly;
  Xaa5 is Ala or Thr;
  Xaa6 is Ala, Phe, Tyr, or naphthylalanine;
  Xaa7 is Thr or Ser;
  Xaa8 is Ala, Ser, or Thr;
  Xaa9 is Ala, Norval, Val, Norleu, Asp, or Glu;
  Xaa10 is Ala, Leu, Ile, Val, pentylglycine, or Met;
  Xaa11 is Ala or Ser;
  Xaa12 is Ala or Lys;
  Xaa13 is Ala or Gln;
  Xaa14 is Ala, Leu, Ile, pentylglycine, Val, or Met;
  Xaa15 is Ala or Glu;
  Xaa16 is Ala or Glu;
  Xaa17 is Ala or Glu;
  Xaa19 is Ala or Val;
  Xaa20 is Ala, or Arg;
  Xaa21 is Ala, Leu, or Lys-NHε-R, wherein R is Lys, Arg, or a C1-C10 straight chain or branched alkanoyl;
  Xaa22 is Ala, Phe, Tyr, or naphthylalanine;
  Xaa23 is Ile, Val, Leu, pentylglycine, tert-butylglycine, or Met;
  Xaa24 is Ala, Glu, or Asp;
  Xaa25 is Ala, Trp, Phe, Tyr, or naphthylalanine;
  Xaa26 is Ala or Leu;
  Xaa27 is Ala or Lys;
  Xaa28 is Ala or Asn; and
  $Z_1$ is —OH, —$NH_2$, Gly-Z2, Gly Gly-Z2, Gly Gly Xaa31-$Z_2$, Gly Gly Xaa31 Ser-Z2,
  Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2,
  Xaa31, Xaa36, Xaa37, and Xaa38 are independently selected from the group consisting of Pro, homoproline, 3Hyp, 4Hyp, thioproline, N-alkylglycine, N-alkylpentylglycine, or
  N-alkylalanine, Xaa39 is Ser, or Tyr, and
  $Z_2$ is —OH, or —$NH_2$,
provided that:
  no more than three of Xaa3, Xaa4, Xaa5, Xaa6, Xaa8, Xaa9, Xaa10, Xaa11,
  Xaa12, Xaa13, Xaa14, Xaa15, Xaa16, Xaa17, Xaa19, Xaa20, Xaa21, Xaa24, Xaa25, Xaa26, Xaa27, and Xaa28 are Ala; and
  when Xaa1 is His, Arg, or Tyr, at least one of Xaa3, Xaa4, and Xaa9 is Ala.

27. The method according to claim 1, wherein the exendin-4 analogue is represented by Chemical Formula II or their pharmaceutically acceptable salts:

Xaa1 Xaa2 Xaa3 Xaa4 Xaa5 Xaa6 Xaa7 Xaa8 Xaa9
Xaa10 Xaa11 Xaa12 Xaa13 Xaa14 Xaa15
Xaa16 Xaa17 Ala Xaa19 Xaa20 Xaa21 Xaa22
Xaa23 Xaa24 Xaa25 Xaa26 $X_1$-$Z_1$,    (Chemical Formula II)

wherein:
  Xaa1 is His, Arg, Tyr, Ala, Norval, Val, Norleu, or 4-imidazopropionyl;
  Xaa2 is Ser, Gly, Ala, or Thr;
  Xaa3 is Ala, Asp, or Glu;
  Xaa4 is Ala, Norval, Val, Norleu, or Gly;
  Xaa5 is Ala or Thr;
  Xaa6 is Ala, Phe, Tyr, or naphthylalanine;
  Xaa7 is Thr or Ser;
  Xaa8 is Ala, Ser, or Thr;
  Xaa9 is Ala, Norval, Val, Norleu, Asp, or Glu;
  Xaa10 is Ala, Leu, Ile, Val, pentylglycine, or Met;
  Xaa11 is Ala or Ser;
  Xaa12 is Ala or Lys;
  Xaa13 is Ala or Gln;
  Xaa14 is Ala, Leu, Ile, pentylglycine, Val, or Met;
  Xaa15 is Ala or Glu;
  Xaa16 is Ala or Glu;
  Xaa17 is Ala or Glu;
  Xaa19 is Ala or Val;
  Xaa20 is Ala or Arg;
  Xaa21 is Ala, Leu, or Lys-NHε-R, wherein R is Lys, Arg, C1-C10 straight chain or branched alkanoyl, or cycloalleyl-alkanoyl;
  Xaa22 is Phe, Tyr, or naphthylalanine;
  Xaa23 is Ile, Val, Leu, pentylglycine, tert-butylglycine, or Met;
  Xaa24 is Ala, Glu, or Asp;
  Xaa25 is Ala, Trp, Phe, Tyr, or naphthylalanine;
  Xaa26 is Ala or Leu;
  $X_1$ is Lys Asn, Asn Lys, Lys-NHε-R Asn, Asn Lys-NHε-R, Lys-NHε-R Ala, Ala Lys-NHε-R, wherein R is Lys, Arg, a C1-C10 straight chain or branched alkanoyl, or cycloalkylalkanoyl;
  $Z_1$ is —OH, —$NH_2$, Gly-Z2, Gly Gly-Z2, Gly Gly Xaa31-$Z_2$, Gly Gly Xaa31 Ser-Z2,
  Gly Gly Xaa31 Ser Ser-Z2, Gly Gly Xaa31 Ser Ser Gly-Z2, Gly Gly Xaa31 Ser Ser Gly Ala-Z2, Gly Gly Xaa31 Ser Ser Gly Ala Xaa36-Z2, Gly Gly Xaa31 Ser Ser Gly Ala Xaa36 Xaa37-Z2, Gly
  Gly Xaa31 Ser Ser Gly Ala Xaa36 Xaa37 Xaa38-Z2, or Gly Gly Xaa31 Ser Ser Gly Ala Xaa36 Xaa37 Xaa38 Xaa39-Z2;
  Xaa31, Xaa36, Xaa37, and Xaa38 are independently selected from the group
  consisting of Pro, homoproline, 3Hyp, 4Hyp, thioproline, N-alkylglycine, N-alkylpentylglycine,
  and N-alkylalanine, Xaa39 is Ser or Tyr; and
  $Z_2$ is —OH or —$NH_2$,
provided that:
  no more than three of Xaa3, Xaa4, Xaa5, Xaa6, Xaa8, Xaa9, Xaa10, Xaa11, Xaa12, Xaa13, Xaa14, Xaa15, Xaa16, Xaa17, Xaa19, Xaa20, Xaa21, Xaa24, Xaa25, and Xaa26 are Ala; and
  when Xaa1 is His, Arg, Tyr, or 4-imidazopropionyl, at least one of Xaa3, Xaa4, and Xaa9 is Ala.

28. The method according to claim 1, wherein the neuroprotective polypeptide is selected from the group consisting of SEQ ID NOS: 1-55.

29. The method according to claim 2, wherein the controlled-release formulation further comprises a biodegradable polymer with a specific viscosity, and a coating material.

30. The method according to claim 3, wherein the long acting formulation comprises a composition for sustained release of the neuroprotective polypeptide.

31. The method according to claim 8, wherein the controlled-release formulation further comprises a biodegradable polymer with a specific viscosity and coating materials.

32. The method according to claim 4, wherein the biodegradable polymer is selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate, a copolymer or a simple mixture of two or more selected from the polymer group, a copolymer of and polyethyleneglycol (PEG), or a polymer-sugar complex where a sugar is coupled with a polymer selected from the polymer group or a copolymer comprising a polymer of the polymer group.

33. The method according to claim 9, wherein the biodegradable polymer is selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate, a copolymer or a simple mixture of two or more selected from the polymer group, a copolymer of a polymer selected from the polymer group and polyethyleneglycol (PEG), or a polymer-sugar complex where a sugar is coupled with a polymer selected from the polymer group or a copolymer comprising a polymer of the polymer group.

34. The method according to claim 10, wherein the biodegradable polymer is selected from the group consisting of polylactide (PLA), polyglycolide (PGA), poly(lactide-co-glycolide) (PLGA), polyorthoester, polyanhydride, polyhydroxybutyric acid, polycaprolactone, and polyalkylcarbonate, a copolymer or a simple mixture of two or more selected from the polymer group, a copolymer of a polymer selected from the polymer group and polyethyleneglycol (PEG), or a polymer-sugar complex where a sugar is coupled with a polymer selected from the polymer group or a copolymer comprising a polymer of the polymer group.

35. The method of claim 8 wherein the device is a pump; wherein the pump is selected from the group consisting of a mini-pump, an osmotic pump, an infusion pump, a peristaltic pump, and a miniature infusion pump.

36. The method of claim 17, wherein the device is a pump; wherein the pump is selected from the group consisting of a mini-pump, an osmotic pump, an infusion pump, a peristaltic pump, and a miniature infusion pump.

37. The method of claim 8, wherein the neuroprotective polypeptide is administered by the device at a rate of about 1 pM/kg/min to about 30 pM/kg/min.

38. The method of any of claim 17, wherein the neuroprotective polypeptide is administered by the device at a rate of about 1 pM/kg/min to about 30 pM/kg/min.

39. The method of claim 18, wherein the neuroprotective polypeptide is administered by the device at a rate of about 1 pM/kg/min to about 30 pM/kg/min.

* * * * *